United States Patent [19]
Conneely et al.

[11] Patent Number: 5,955,316
[45] Date of Patent: *Sep. 21, 1999

[54] EXPRESSION OF PROCESSED RECOMBINANT LACTOFERRIN AND LACTOFERRIN POLYPEPTIDE FRAGMENTS FROM A FUSION PRODUCT IN ASPERGILLUS

[75] Inventors: Orla M. Conneely, Houston, Tex.; Denis R. Headon, Galway, Ireland; Bert W. O'Malley, Houston, Tex.

[73] Assignee: Agennix, Inc., Houston, Tex.

[ * ] Notice: This patent is subject to a terminal disclaimer.

[21] Appl. No.: 08/691,123

[22] Filed: Aug. 1, 1996

Related U.S. Application Data

[63] Continuation of application No. 08/303,009, Nov. 2, 1994, Pat. No. 5,571,697, which is a continuation-in-part of application No. 08/145,681, Oct. 28, 1993, Pat. No. 5,571,691, and a continuation of application No. 08/250,308, May 27, 1994, Pat. No. 5,571,896, which is a continuation-in-part of application No. 07/873,304, Apr. 24, 1992, abandoned, said application No. 08/145,681, is a continuation-in-part of application No. 07/967,947, Oct. 27, 1992, abandoned, which is a continuation of application No. 07/348,270, May 5, 1989, abandoned.

[51] Int. Cl.[6] .......................... C12N 15/62; C12N 15/64; C12N 15/80; C07K 14/79
[52] U.S. Cl. .................. 435/69.7; 435/254.3; 435/320.1; 530/350; 530/400; 536/23.4; 536/23.5
[58] Field of Search .............................. 424/439; 514/6; 435/69.7, 172.3, 252.3, 254.14, 254.21, 254.23, 254.3, 320.1; 530/350, 390, 400, 412; 536/23.4, 23.5

[56] References Cited

U.S. PATENT DOCUMENTS

| | | | |
|---|---|---|---|
| 5,304,633 | 4/1994 | Tomita et al. | 530/326 |
| 5,571,691 | 11/1996 | Conneely et al. | 435/69.1 |
| 5,571,697 | 11/1996 | Conneely et al. | 435/69.7 |
| 5,571,896 | 11/1996 | Conneely et al. | 530/400 |

FOREIGN PATENT DOCUMENTS

| | | |
|---|---|---|
| WO 91/05045 | 4/1991 | WIPO . |
| WO 91/13982 | 9/1991 | WIPO . |

OTHER PUBLICATIONS

LeGrand, D., et al., Biochimica et Biophysica Acta, vol. 787, "Characterization and localization of an iron–binding 18–kDa glycopeptide isolated from the N–terminal half of human lactotransferrin", pp. 75–84, 1984.

Valenti, P., et al., FEMS Microbiology Letters, vol. 33, "Interaction between lactoferrin and ovotransferrin and Candida cells", pp. 271–275, 1986.

Anderson, B. F., et al., Proceedings of the National Academy of Sciences, U.S.A., vol. 84, "Structure of human lactoferrin at 3.2A resolution", pp. 1769–1773, 1987.

Epstein, J. B., et al., Reviews of Infectious Diseases, vol. 6, "Oral Candidiasis: Pathogenesis and host defense", pp. 96–106, 1984.

Anderson, B. F., et al., Journal of Molecular Biology, vol. 209, "Structure of human lactoferrin: Crystallographic structure analysis and refinement at 1.8A resolution", pp. 711–734, 1989.

Soukka, T., et al., FEMS Microbiology Letters, vol. 90, "Fungicidal effect of human lactoferrin against Candida albicans", pp. 223–228, 1992.

Primary Examiner—Charles L. Patterson, Jr.
Assistant Examiner—William W. Moore
Attorney, Agent, or Firm—Albert P. Halluin; Howrey & Simon

[57] ABSTRACT

The subject invention provides for the production of lactoferrins and lactoferrin polypeptide fragments using the host cells Aspergillus in combination with novel plasmid constructs. More specifically, the subject invention provides novel vector constructs capable of producing lactoferrins and lactoferrin polypeptide fragments in Aspergillus host cells. More particularly, the subject invention provides for novel plasmid constructs suitable for use with Aspergillus and especially *Aspergillus awamori, niger* and *oryzae* host cells, which enables them to produce large amounts of recombinant lactoferrins and lactoferrin polypeptide fragments.

55 Claims, 59 Drawing Sheets

FIG. 4

- natural human lactoferrin gene construct:

mature natural human lactoferrin

LF signal seq. --- Cys Leu Ala | Gly Arg Arg Arg Arg Ser Val Gln Trp Cys →

- recombinant human lactoferrin gene construct in *A. awamori*:

mature recombinant human lactoferrin glucoamy. gn. --- Ser Lys Arg* | Gly Arg Arg Arg Arg Ser Val Gln Trp Cys →

*KEX-2 cleavage site

- rhLF N-terminal amino acid sequence:

Gly Arg Arg Arg Arg Ser Val Gln Trp Cys →

FIG. 10B
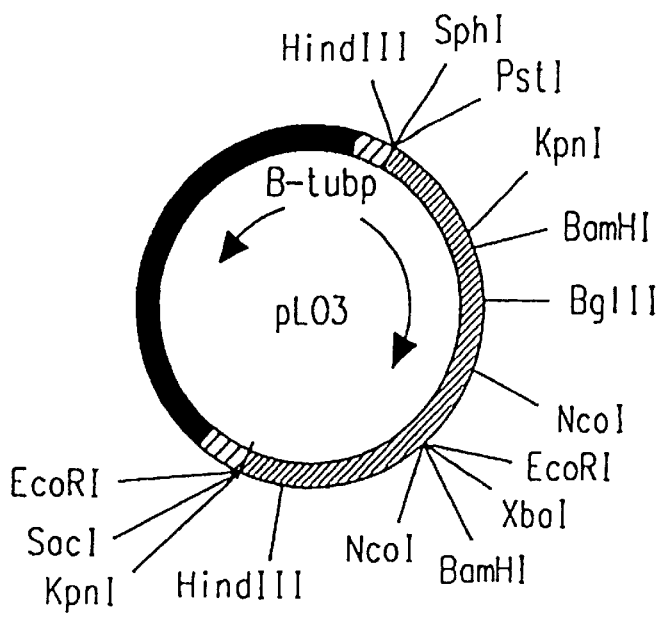
EcoRI SITES FILLED AND BLUNT LIGATED
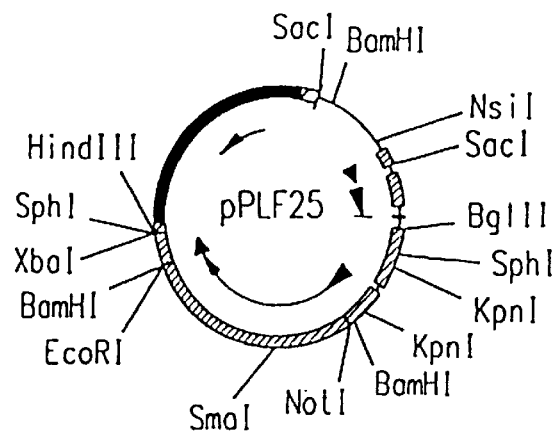
pPLF25 DIGESTED WITH HindIII
CONT. ON FIG.10C

FIG. 10C
FROM FIG.10B
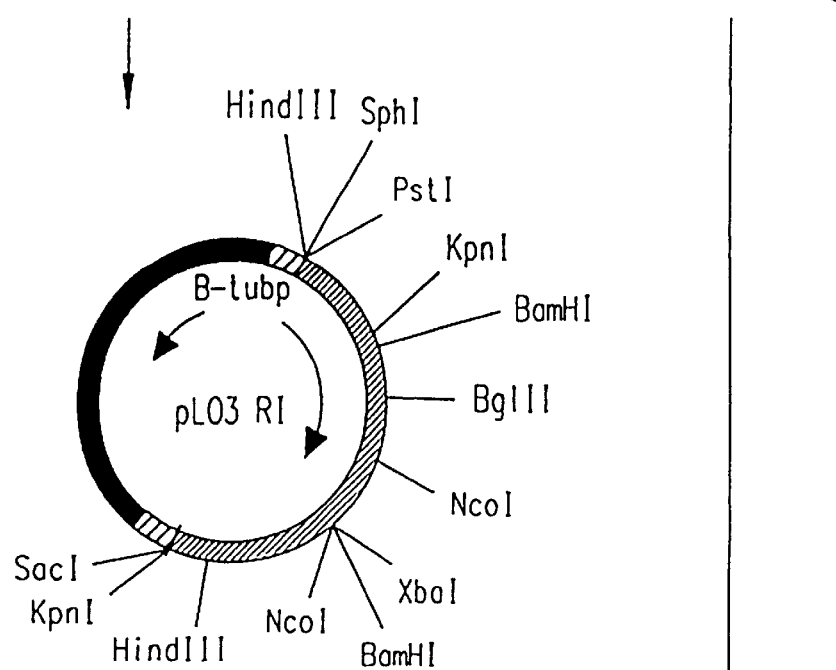
2.1 HindIII FRAGMENT ISOLATED; LIGATED TO pPLF25
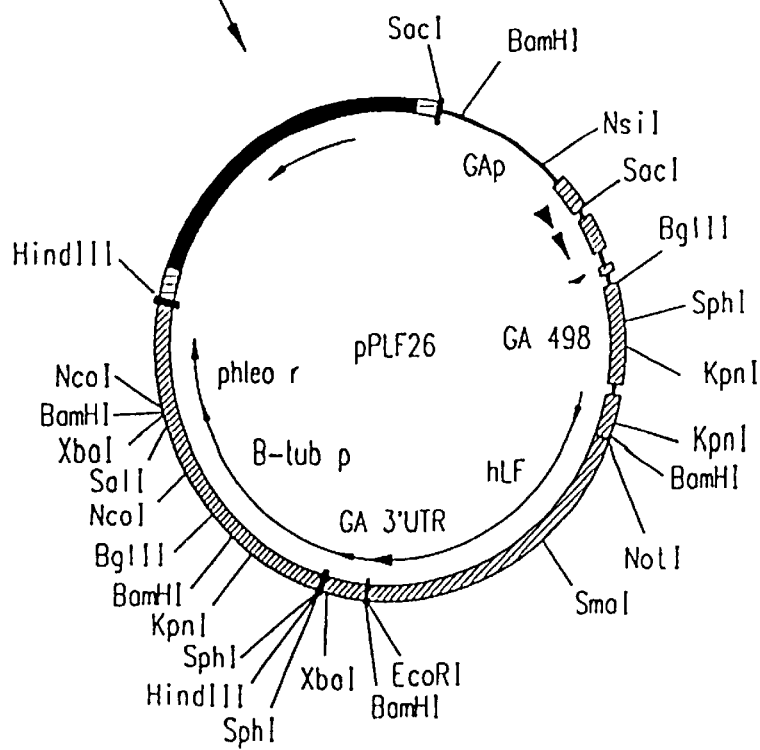

FIG. 13A (Linear) MAPSORT of: hlf2 check: 7473 from: 1 to: 2360
Mismatch: 0 MinCuts = 1 MaxCuts: 10

AccI GT'mk_AC
Cuts at:    0    319   2360
  Size:    319   2041
AceIII CAGCTCnnnnnnn'nnnn
Cuts at:    0    948   1125   2183   2219   2360
  Size:    948    177   1058     36    141
    Fragments arranged by size:
           1058    948    177    141     36
AhdI GACnn_n'nnGTC
Cuts at:    0    472   2360
  Size:    472   1888
AlwI GGATCnnnn'n_
Cuts at:    0   1341   1955   2360
  Size:   1341    614    405
    Fragments arranged by size:
           1341    614    405
AlwNI CAG_nnn'CTG
Cuts at:    0   1139   1913   2360
  Size:   1139    774    447
    Fragments arranged by size:
           1139    774    447
ApaI G_GGCC'C
Cuts at:    0     56   2360
  Size:     56   2304
ApaBI GCA_nnnnn'TGC
Cuts at:    0   1140   1789   2360
  Size:   1140    649    571
    Fragments arranged by size:
           1140    649    571
ApaLI G'TGCA_C
Cuts at:    0    101   2360
  Size:    101   2259
ApoI r'AATT_y
Cuts at:    0      1    930   1527   1932   2136   2318   2360
  Size:     1    929    597    405    204    182     42
    Fragments arranged by size:
            929    597    405    204    182     42      1

FIG. 13B

AvaI C'yCGr_G
Cuts at:    0    48    117    820    1010    1571    2360
  Size:        48    69    703    190    561    789
  Fragments arranged by size:
              789    703    561    190    69    48
AvaII G'GwC_C
Cuts at:    0    325    439    495    725    824    2067    2360
  Size:        325    114    56    230    99    1243    293
  Fragments arranged by size:
              1243    325    293    230    114    99    56
BanI G'GyrC_C
Cuts at:    0    657    1004    1298    1675    2360
  Size:        657    347    294    377    685
  Fragments arranged by size:
              685    657    377    347    294
BanII G_rGCy'C
Cuts at:    0    56    508    1521    2360
  Size:        56    452    1013    839
  Fragments arranged by size:
              1013    839    452    56
BbsI GAAGACnn'nnnn_
Cuts at:    0    20    2360
  Size:        20    2340
BbvI GCAGCnnnnnnnn'nnnn_
Cuts at:    0    168    394    528    1079    1126    1189    1780    1827
  Size:        168    226    134    551    47    63    591    47
Cuts at:    1827    1900    2360
  Size:        73    460
  Fragments arranged by size:
              591    551    460    226    168    134    73    63    47    47
Bce83I CTTGAGnnnnnnnnnnnnnn_nn'
Cuts at:    0    1088    1187    2360
  Size:        1088    99    1173
  Fragments arranged by size:
              1173    1088    99
BcefI ACGGCnnnnnnnnnnnn'n_
Cuts at:    0    62    343    823    1447    1670    1855    2360
  Size:        62    281    480    624    223    185    505
  Fragments arranged by size:
              624    505    480    281    223    185    62

FIG. 13C

BfaI C'TA_G
Cuts at:   0   952   1414   1834   2360
  Size:   952   462   420   526
  Fragments arranged by size:
          952   526   462   420
BfiI ACTGGG
Cuts at:   0   1664   2360
  Size:   1664   696
BglI GCCn_nnn'nGGC
Cuts at:   0   427   843   1807   2360
  Size:   427   416   964   553
  Fragments arranged by size:
          964   553   427   416
BglII A'GATC_T
Cuts at:   0   965   1575   2360
  Size:   965   610   785
  Fragments arranged by size:
          965   785   610
BmgI GkGCCC
Cuts at:   0   54   1007   1557   1631   2360
  Size:   54   953   550   74   729
  Fragments arranged by size:
          953   729   550   74   54
BpmI CTGGAGnnnnnnnnnnnnnnn_nn'
Cuts at:   0   706   1714   2360
  Size:   706   1008   646
  Fragments arranged by size:
          1008   706   646
Bpu10I CC'TnA_GC
Cuts at:   0   502   1765   2188   2360
  Size:   502   1263   423   172
  Fragments arranged by size:
          1263   502   423   172
BsaWI w'CCGG_w
Cuts at:   0   1672   2360
  Size:   1672   688
BsaXI ACnnnnnCTCC
Cuts at:   0   87   1037   1268   2360
  Size:   87   950   231   1092
  Fragments arranged by size:
          1092   950   231   87

FIG. 13D

BsbI CAACAC
Cuts at:   0   778   2014   2227   2360
  Size:      778   1236   213   133
  Fragments arranged by size:
             1236   778   213   133
BscGI CCCGT
Cuts at:   0   324   494   681   1517   2360
  Size:      324   170   187   836   843
  Fragments arranged by size:
             843   836   324   187   170
BseRI GAGGAGnnnnnnnnn_nn'
Cuts at:   0   617   1095   1181   2360
  Size:      617   478   86   1179
  Fragments arranged by size:
             1179   617   478   86
BsgI GTGCAGnnnnnnnnnnnnnnnn_nn'
Cuts at:   0   577   2360
  Size:      577   1783
BsiEI CG_ry'CG
Cuts at:   0   10   2360
  Size:      10   2350
BsiHKAI G_wGCw'C
Cuts at:   0   105   714   1592   2109   2360
  Size:      105   609   878   517   251
  Fragments arranged by size:
             878   609   517   251   105
BsmI GAATG_Cn'
Cuts at:   0   1694   2360
  Size:      1694   666
BsmAI GTCTCn'nnnn_
Cuts at:   0   187   670   682   1690   1882   2360
  Size:      187   483   12   1008   192   478
  Fragments arranged by size:
             1008   483   478   192   187   12
BsmBI CGTCTCn'nnnn_
Cuts at:   0   670   682   1690   2360
  Size:      670   12   1008   670
  Fragments arranged by size:
             1008   670   670   12
BsmFI GGGACnnnnnnnnnn'nnnn_
Cuts at:   0   338   479   614   762   810   2080   2360
  Size:      338   141   135   148   48   1270   280
  Fragments arranged by size:
             1270   338   280   148   141   135   48

FIG. 13E

```
Bsp24I GACnnnnnnTGGnnnnnnn_nnnnn'
  Cuts at:    0    52    84   239   271   569   601    62  2094
     Size:       52    32   155    32   298    32  1461    32
  Cuts at: 2094  2360
     Size:     266
  Fragments arranged by size:
            1461   298   266   155    52    32     3    32    32
Bsp1286I G_dGCh'C
  Cuts at:    0    56   105   508   714  1009  1521   559  1592
     Size:       56    49   403   206   295   512    38    33
  Cuts at: 1592  1633  2109  2360
     Size:      41   476   251
  Fragments arranged by size:
             512   476   403   295   251   206    56    49    41    38    33
BspMI ACCTGCnnnn'nnnn_
  Cuts at:    0  1194  2360
     Size:     1194  1166
BsrI ACTG_Gn'
  Cuts at:    0   206   789  1154  1667  1979  2360
     Size:      206   583   365   513   312   381
  Fragments arranged by size:
             583   513   381   365   312   206
BsrDI GCAATG_nn'
  Cuts at:    0   220  1646  2360
     Size:      220  1426   714
  Fragments arranged by size:
            1426   714   220
BsrGI T'GTAC_A
  Cuts at:    0  1273  2360
     Size:     1273  1087
BstXI CCAn_nnnn'nTGG
  Cuts at:    0   942  1161  1256  2360
     Size:      942   219    95  1104
  Fragments arranged by size:
            1104   942   219    95
BstYI r'GATC_y
  Cuts at:    0   965  1575  1947  2360
     Size:      965   610   372   413
  Fragments arranged by size:
             965   610   413   372
```

FIG. 13F

```
Bsu36I CC'TnA_GG
Cuts at:    0   2142   2360
  Size:       2142    218
CjeI ACnnnnnnTGGnnnnnnn'nnnnnn_
Cuts at:    0    79   188   266   563   618  2056 2360
  Size:         79   109    78   297    55  1438  304
  Fragments arranged by size:
             1438   304   297   109    79    78    55
CviRI TG'CA
Cuts at:    0   103   184   404   558  1216  1281  1476  1525
  Size:        103    81   220   154   658    65   195    49
Cuts at: 1525  1704  1730  2360
  Size:        179    26   630
  Fragments arranged by size:
              658   630   220   195   179   154   103    81
               65    49    26
DdeI C'TnA_G
Cuts at:    0   502   536   672  1684  1765  1828  2017  2142
  Size:        502    34   136  1012    81    63   189   125
Cuts at: 2142  2188  2297  2360
  Size:         46   109    63
  Fragments arranged by size:
             1012   502   189   136   125   109    81    63    63    46    34
DpnI GA'TC
Cuts at:    0   967  1348  1406  1577  1949  2360
  Size:        967   381    58   171   372   411
  Fragments arranged by size:
              967   411   381   372   171    58
DraIII CAC_nnn'GTG
Cuts at:    0   852  2020  2360
  Size:        852  1168   340
  Fragments arranged by size:
             1168   852   340
DsaI C'CryG_G
Cuts at:    0   358  1462  1492  1852  1870  2036  2360
  Size:        358  1104    30   360    18   166   324
  Fragments arranged by size:
             1104   360   358   324   166    30    18
EaeI y'GGCC_r
Cuts at:    0    74   523  2026  2360
  Size:         74   449  1503   334
  Fragments arranged by size:
             1503   449   334    74
```

FIG. 13G

EarI CTCTTCn'nnn_
Cuts at:      0     152    1509   2216   2360
   Size:        152    1357    707    144
   Fragments arranged by size:
              1357    707    152    144
EciI TCCGCC
Cuts at:      0     313    891    2360
   Size:        313    578   1469
   Fragments arranged by size:
              1469    578    313
Eco57I CTGAAGnnnnnnnnnnnnnnnn_nn'
Cuts at:      0     432    629    2269   2360
   Size:        432    197   1640    91
   Fragments arranged by size:
              1640    432    197    91
EcoNI CCTnn'n_nnAGG
Cuts at:      0    1372   1905   2248   2360
   Size:       1372    533    343    112
   Fragments arranged by size:
              1372    533    343    112
EcoO109I rG'GnC_Cy
Cuts at:      0     52    53    725    824    2231   2360
   Size:        52     1    672    99   1407    129
   Fragments arranged by size:
              1407    672    129    99    52    1
EcoRI G'AATT_C
Cuts at:      0     1    2136   2360
   Size:         1   2135    224
   Fragments arranged by size:
              2135    224     1
EcoRV GAT'ATC
Cuts at:      0    1380   2360
   Size:       1380    980
FauI CCCGCnnnn'nn_
Cuts at:      0    590    1099   2360
   Size:       590    509   1261
   Fragments arranged by size:
              1261    590    509
FokI GGATGnnnnnnnnn'nnnn_
Cuts at:      0    189    460    882   1044   1272   1895   2252   2360
   Size:       189    271    422    162    228    623    357    108
   Fragments arranged by size:
               623    422    357    271    228    189    162    108

FIG. 13H

FspI TGC'GCA
Cuts at:   0   1143   2360
   Size:   1143   1217
GdiII y'GGCC_G
Cuts at:   0   74   2360
   Size:   74   2286
HaeI wGG'CCw
Cuts at:   0   123   219   280   430   525   2028   2360
   Size:   123   96   61   150   95   1503   332
   Fragments arranged by size:
           1503   332   150   123   96   95   61
HgiEII ACCnnnnnnGGT
Cuts at:   0   254   2360
   Size:   254   2106
HhaI G_CG'C
Cuts at:   0   1106   1144   1793   2360
   Size:   1106   38   649   567
   Fragments arranged by size:
           1106   649   567   38
Hin4I GAbnnnnnvTC
Cuts at:   0   471   727   1573   1578   1580   2263   2360
   Size:   471   256   846   5   2   683   97
   Fragments arranged by size:
           846   683   471   256   97   5   2
HinfI G'AnT_C
Cuts at:   0   195   881   981   1020   1862   2032   2360
   Size:   195   686   100   39   842   170   328
   Fragments arranged by size:
           842   686   328   195   170   100   39
HphI GGTGAnnnnnnn_n'
Cuts at:   0   380   916   1626   2360
   Size:   380   536   710   734
   Fragments arranged by size:
           734   710   536   380
MaeII A'CG_T
Cuts at:   0   691   1699   2360
   Size:   691   1008   661
   Fragments arranged by size:
           1008   691   661

FIG. 131

```
MaeIII 'GTnAC_
Cuts at:     0    245    760    922   1149   1181   1338   1718   1823
  Size:        245    515    162    227     32    157    380    105
Cuts at:  1823   2360
  Size:        537
  Fragments arranged by size:
           537    515    380    245    227    162    157    105     32
MboII GAAGAnnnnnnnn_n'
Cuts at:     0     20    169    383    524    876   1496   2170   2173
  Size:         20    149    214    141    352    620    674      3
Cuts at:  2173   2203   2360
  Size:         30    157
  Fragments arranged by size:
           674    620    352    214    157    149    141     30     20     3
MmeI TCCrACnnnnnnnnnnnnnnnnnn_nn'
Cuts at:     0     30   2360
  Size:         30   2330
MscI TGG'CCA
Cuts at:     0    525   2028   2360
  Size:        525   1503    332
  Fragments arranged by size:
          1503    525    332
MslI CAynn'nnrTG
Cuts at:     0    352   1461   2360
  Size:        352   1109    899
  Fragments arranged by size:
          1109    899    352
MspI C'CG_G
Cuts at:     0    553    821   1042   1097   1673   1959   2360
  Size:        553    268    221     55    576    286    401
  Fragments arranged by size:
           576    553    401    286    268    221     55
MspA1I CmG'CkG
Cuts at:     0    181    392    444    519    544   2360
  Size:        181    211     52     75     25   1816
  Fragments arranged by size:
          1816    211    181     75     52     25
NciI CC's_GG
Cuts at:     0    553    821    822   1097   1959   2360
  Size:        553    268      1    275    862    401
  Fragments arranged by size:
           862    553    401    275    268      1
```

FIG. 13J

```
NcoI C'CATG_G
Cuts at:    0   1492  1852  2036  2360
  Size:     1492  360   184   324
  Fragments arranged by size:
            1492  360   324   184
NdeI CA'TA_TG
Cuts at:    0   2051  2360
  Size:     2051  309
NlaIII _CATG'
Cuts at:    0   20   837   1253  1496  1762  1856  1869  2040
  Size:     20   817  416   243   266   94    13    171
Cuts at:    2040  2360
  Size:     320
  Fragments arranged by size:
            817  416  320  266  243  171  94  20       13
PleI GAGTCnnnn'n_
Cuts at:    0   189  975   2026  2360
  Size:     189  786  1051  334
  Fragments arranged by size:
            1051  786  334  189
Psp5II rG'GwC_Cy
Cuts at:    0   725  824   2360
  Size:     725  99   1536
  Fragments arranged by size:
            1536  725  99
PstI C_TGCA'G
Cuts at:    0   1283  1478  2360
  Size:     1283  195   882
  Fragments arranged by size:
            1283  882   195
PvuII CAG'CTG
Cuts at:    0   181  392  519  544  2360
  Size:     181  211  127  25   1816
  Fragments arranged by size:
            1816  211  181  127  25
RsaI GT'AC
Cuts at:    0   642  1032  1275  2360
  Size:     642  390  243   1085
  Fragments arranged by size:
            1085  642  390  . 243
```

FIG. 13K

```
SanDI GG'GwC_CC
  Cuts at:    0    824   2360
    Size:       824   1536
SapI GCTCTTCn'nnn_
  Cuts at:    0   1509   2216   2360
    Size:      1509    707    144
    Fragments arranged by size:
               1509    707    144
Sau3AI 'GATC_
  Cuts at:    0    965   1346   1404   1575   1947   2360
    Size:       965    381     58    171    372    413
    Fragments arranged by size:
                965    413    381    372    171     58
SfaNI GCATCnnnnn'nnnn_
  Cuts at:    0    230    860   1225   1235   2360
    Size:       230    630    365     10   1125
    Fragments arranged by size:
               1125    630    365    230     10
SfcI C'TryA_G
  Cuts at:    0    304    460   1279   1474   2360
    Size:       304    156    819    195    886
    Fragments arranged by size:
                886    819    304    195    156
SmaI CCC'GGG
  Cuts at:    0    822   2360
    Size:       822   1538
Sse8647I AG'GwC_CT
  Cuts at:    0    725   2360
    Size:       725   1635
SspI AAT'ATT
  Cuts at:    0   1539   2061   2360
    Size:      1539    522    299
    Fragments arranged by size:
               1539    522    299
StuI AGG'CCT
  Cuts at:    0    280    430   2360
    Size:       280    150   1930
    Fragments arranged by size:
               1930    280    150
StyI C'CwwG_G
  Cuts at:    0   1034   1492   1852   2036   2234   2360
    Size:      1034    458    360    184    198    126
    Fragments arranged by size:
               1034    458    360    198    184    126
```

FIG. 13L

```
TaqI T'CG_A
  Cuts at:      0    999   1804   2360
    Size:     999    805    556
  Fragments arranged by size:
             999    805    556
TaqII GACCGAnnnnnnnnnn_nn'
  Cuts at:      0    342   2360
    Size:     342   2018
TauI GCsGC
  Cuts at:      0    310    380   2360
    Size:     310     70   1980
  Fragments arranged by size:
            1980    310     70
TfiI G'AwT_C
  Cuts at:      0    881   1020   1862   2360
    Size:     881    139    842    498
  Fragments arranged by size:
             881    842    498    139
ThaI CG'CG
  Cuts at:      0   1106   2360
    Size:    1106   1254
TseI GCwGC
  Cuts at:      0    182    383    517   1093   1140   1178   1794   1841
    Size:     182    201    134    576     47     38    616     47
  Cuts at:   1841   1914   2360
    Size:      73    446
  Fragments arranged by size:
             616    576    446    201    182    134     73     47     38
Tsp45I 'GTsAC_
  Cuts at:      0    245    922   1181   1338   1718   1823   2360
    Size:     245    677    259    157    380    105    537
  Fragments arranged by size:
             677    537    380    259    245    157    105
Tsp509I 'AATT_
  Cuts at:      0      1    485    930   1527   1932   2136   2280   2318
    Size:       1    484    445    597    405    204    144     38
  Cuts at:   2318   2360
    Size:      42
  Fragments arranged by size:
             597    484    445    405    204    144     42     38
```

FIG. 13M

Tth111I GACn'n_nGTC
Cuts at:    0    64    2360
   Size:       64    2296
Tth111II CAArCAnnnnnnnnn_nn'
Cuts at:    0    708    2360
   Size:       708    1652
UbaCI wGTACw
Cuts at:    0    1275    2360
   Size:      1275    1085
XcmI CCAnnnnn_n'nnnnTGG
Cuts at:    0    484    2360
   Size:       484    1876

Enzymes that do cut and were not excluded:

| | | | | |
|---|---|---|---|---|
| AccI | AceIII | AhdI | AlwI | AlwNI |
| ApaI | ApaBI | ApaLI | ApoI | AvaI |
| AvaII | BanI | BanII | BbsI | BbvI |
| Bce83I | BcefI | BfaI | BfiI | BglI |
| BglII | BmgI | BpmI | Bpu10I | BsaWI |
| BsaXI | BsbI | BscGI | BseRI | BsgI |
| BsiEI | BsiHKAI | BsmI | BsmAI | BsmBI |
| BsmFI | Bsp24I | Bsp1286I | BspMI | BsrI |
| BsrDI | BsrGI | BstXI | BstYI | Bsu36I |
| CjeI | CviRI | DdeI | DpnI | DraIII |
| DsaI | EaeI | EarI | EciI | Eco57I |
| EcoNI | EcoO109I | EcoRI | EcoRV | FauI |
| FokI | FspI | GdiII | HaeI | HgiEII |
| HhaI | Hin4I | HinfI | HphI | MaeII |
| MaeIII | MboII | MmeI | MscI | MsII |
| MspI | MspA1I | NciI | NcoI | NdeI |
| NlaIII | PleI | Psp5II | PstI | PvuII |
| RsaI | SanDI | SapI | Sau3AI | SfaNI |
| SfcI | SmaI | Sse8647I | SspI | StuI |
| StyI | TaqI | TaqII | TauI | TfiI |
| ThaI | TseI | Tsp45I | Tsp509I | Tth111I |
| Tth111II | UbaCIXcmI | | | |

Enzymes that do not cut:

| | | | | |
|---|---|---|---|---|
| AatII | AflII | AflIII | AscI | AvrII |
| BaeI | BamHI | BcgI | BcgI | BclI |
| BplI | Bpu1102I | BsaI | BsaAI | BsaBI |
| BsaHI | BspEI | BspGI | BspLU11I | BsrBI |
| BsrFI | BssHII | BssSI | Bst1107I | BstEII |
| ClaI | DraI | DrdI | DrdII | EagI |
| Eco47III | FseI | HaeII | HgaI | HincII |

FIG. 13N

| | | | | |
|---|---|---|---|---|
| HindIII | HpaI | KpnI | MluI | MseI |
| MunI | NarI | NgoAIV | NheI | NotI |
| NruI | NsiI | NspI | NspV | PacI |
| Pfl1108I | PflMI | PinAI | PmeI | PmlI |
| PshAI | Psp1406I | PvuI | RcaI | RleAI |
| RsrII | SacI | SacII | SalI | ScaI |
| SexAI | SfiI | SgfI | SgrAI | SnaBI |
| SpeI | SphI | SrfI | Sse8387I | SunI |
| SwaI | VspI | XbaI | XhoI | XmnI |

Enzymes excluded; MinCuts: 1  MaxCuts: 10

| | | | | |
|---|---|---|---|---|
| AciI | AluI | BccI | BsaJI | BslI |
| BsoFI | Cac8I | CjeI | CjePI | CjePI |
| CviJI | EcoRII | HaeIII | MnlI | MwoI |
| NlaIV | Sau96I | ScrFI | TspRI | |

FIG. 14A (Linear)MAPSORT of: piglac.gb_om  check: 9514  from:1 to :2259
LOCUS      PIGLAC      2259 bp ss-mRNA           MAM
DEFINITION  Sus scrofa lactoferrin mRNA, complete cds.
ACCESSION   M81327 M61828
KEYWORDS    lactoferrin.
SOURCE      Sus scrofa lactational mammary gland cDNA to mRNA.
  ORGANISM  Sus scrofa . . .
Mismatch: 0  MinCuts = 1  MaxCuts: 10
With 209 enzymes: *

AceIII CAGCTCnnnnnnn'nnnn_
Cuts at:    0    497   915   1092   1740   2239   2259
  Size:       497   418   177    648    499    20
  Fragments arranged by size:
             648   499   497   418   177   20
AlwI GGATCnnnn'n_
Cuts at:    0    965   1531   1544   2036   2259
  Size:       965   566   13     492    223
  Fragments arranged by size:
             965   566   492   223   13
AlwNI CAG_nnn'CTG
Cuts at:    0    219   1034   1148   1196   2259
  Size:       219   815   114    48     1063
  Fragments arranged by size:
             1063   815   219   114   48
ApaLI G'TGCA_C
Cuts at:    0    1549   2259
  Size:       1549   710
ApoI r'AATT_y
Cuts at:    0    495   1488   1497   2259
  Size:       495   993   9      762
  Fragments arranged by size:
             993   762   495   9
AvaI C'yCGr_G
Cuts at:    0    33    787   2259
  Size:       33    754   1472
  Fragments arranged by size:
             1472   754   33
AvaII G'GwC_C
Cuts at:    0    791   932   1095   2259
  Size:       791   141   163    1164
  Fragments arranged by size:
             1164   791   163   141

FIG. 14B

BaeI ACnnnnGTAyC
Cuts at:    0    1614    2259
  Size:    1614    645

BamHI G'GATC_C
Cuts at:    0    1536    2259
  Size:    1536    723

BanI G'GyrC_C
Cuts at:    0    624    1265    1636    1770    2259
  Size:    624    641    371    134    489
  Fragments arranged by size:
           641    624    489    371    134

BanII G_rGCy'C
Cuts at:    0    475    2259
  Size:    475    1784

BccI CCATC
Cuts at:    0    81    197    233    530    842    956    1025    1229
  Size:    81    116    36    297    312    114    69    204
Cuts at:    1229    1769    2048    2259
  Size:    540    279    211
  Fragments arranged by size:
           540    312    297    279    211    204    116    114    81    69    36

BcefI ACGGCnnnnnnnnnnnn'n_
Cuts at:    0    1060    1075    1333    2259
  Size:    1060    15    258    926
  Fragments arranged by size:
           1060    926    258    15

BcgI CGAnnnnnnTGCnnnnnnnnnn_nn'
Cuts at:    0    367    401    2259
  Size:    367    34    1858
  Fragments arranged by size:
           1858    367    34

BfiI ACTGGG
Cuts at:    0    456    1823    2259
  Size:    456    1367    436
  Fragments arranged by size:
           1367    456    436

BglI GCCn_nnn'nGGC
Cuts at:    0    201    394    1768    2259
  Size:    201    193    1374    491
  Fragments arranged by size:
           1374    491    201    193

FIG. 14C

BglII A'GATC_T
Cuts at:   0   286   2259
  Size:   286   1973
BmgI GkGCCC
Cuts at:   0   518   1592   2259
  Size:   518   1074   667
  Fragments arranged by size:
          1074   667   518

BpII GAGnnnnnCTC
Cuts at:   0   171   2259
  Size:   171   2088
BpmI CTGGAGnnnnnnnnnnnnnnn_nn'
Cuts at:   0   462   2259
  Size:   462   1797
Bpu10I CC'TnA_GC
Cuts at:   0   469   2149   2259
  Size:   469   1680   110
  Fragments arranged by size:
          1680   469   110
BsaI GGTCTCn'nnnn_
Cuts at:   0   1531   1841   1941   2259
  Size:   1531   310   100   318
  Fragments arranged by size:
          1531   318   310   100
BsaWI w'CCGG_w
Cuts at:   0   621   1939   2116   2259
  Size:   621   1318   177   143
  Fragments arranged by size:
          1318   621   177   143
BsbI CAACAC
Cuts at:   0   1332   1560   1696   1975   2259
  Size:   1332   228   136   279   284
  Fragments arranged by size:
          1332   284   279   228   136
BscGI CCCGT
Cuts at:   0   294   1011   2166   2259
  Size:   294   717   1155   93
  Fragments arranged by size:
          1155   717   294   93
BseRI GAGGAGnnnnnnnnn_nn'
Cuts at:   0   1116   2151   2259
  Size:   1116   1035   108
  Fragments arranged by size:
          1116   1035   108

FIG. 14D

```
BsgI GTGCAGnnnnnnnnnnnnnn_nn'
Cuts at:    0    624   2259
  Size:        624   1635
BsiEI CG_ry'CG
Cuts at:    0    273   2259
  Size:        273   1986
BsiHKAI G_wGCw'C
Cuts at:    0   1520   1553   2070   2259
  Size:       1520     33    517    189
  Fragments arranged by size:
              1520    517    189     33

BslI CCnn_nnn'nnGG
Cuts at:    0     69    449    612    788   1335   1577   1814   2084
  Size:         69    380    163    176    547    242    237    270
Cuts at: 2084   2142   2210   2259
  Size:          58     68     49
  Fragments arranged by size:
               547    380    270    242    237    176    163     69     68     58     49
BsmI GAATG_Cn'
Cuts at:    0    765   1655   2259
  Size:        765    890    604
  Fragments arranged by size:
               890    765    604
BsmAI GTCTCn'nnnn_
Cuts at:    0   1531   1841   1941   2078   2259
  Size:       1531    310    100    137    181
  Fragments arranged by size:
              1531    310    181    137    100
BsmFI GGGACnnnnnnnnnn'nnnn_
Cuts at:    0     50    308    729    777   2259
  Size:         50    258    421     48   1482
  Fragments arranged by size:
              1482    421    258     50     48
Bsp24I GACnnnnnnTGGnnnnnnn_nnnnn'
Cuts at:    0     37     69    215    247    536    568   2259
  Size:         37     32    146     32    289     32   1691
  Fragments arranged by size:
              1691    289    146     37     32     32     32
Bsp1286I G_dGCh'C
Cuts at:    0    475    520   1520   1553   1594   2070   2259
  Size:        475     45   1000     33     41    476    189
  Fragments arranged by size:
              1000    476    475    189     45     41     33
```

FIG. 14E

BspGI CTGGAC
Cuts at:   0   1098   1190   2259
  Size:    1098    92   1069
  Fragments arranged by size:
         1098   1069    92
BspMI ACCTGCnnnn'nnnn_
Cuts at:   0   394   703   2259
  Size:    394   309   1556
  Fragments arranged by size:
         1556   394   309
BsrI ACTG_Gn'
Cuts at:   0   119   257   459   756   860   1822   2259
  Size:    119   138   202   297   104   962   437
  Fragments arranged by size:
         962   437   297   202   138   119   104
BsrDI GCAATG_nn'
Cuts at:   0   1571   2259
  Size:    1571   688
BsrFI r'CCGG_y
Cuts at:   0   272   442   1117   2259
  Size:    272   170   675   1142
  Fragments arranged by size:
         1142   675   272   170
BssSI C'TCGT_G
Cuts at:   0   2251   2259
  Size:    2251    8
BstXI CCAn_nnnn'nTGG
Cuts at:   0   909   2259
  Size:    909   1350
BstYI r'GATC_y
Cuts at:   0   286   970   1536   2259
  Size:    286   684   566   723
  Fragments arranged by size:
         723   684   566   286
Bsu36I CC'TnA_GG
Cuts at:   0   1035   2209   2259
  Size:    1035   1174   50
  Fragments arranged by size:
         1174   1035   50
Cac8I-GCn'nGC
Cuts at:   0   1069   1119   1250   1439   1461   1888   2133   2193
  Size:   1069    50   131   189    22   427   245    60
Cuts at:  2193   2259
  Size:    66
  Fragments arranged by size:
         1069   427   245   189   131   66   60   50

FIG. 14F

```
CjeI ACnnnnnnTGGnnnnnnn'nnnnnn
Cuts at:     0    64    164   242   410   530   585   855   1526
   Size:        64   100    78   168   120    55   270   671
Cuts at:  1526  2259
   Size:        733
   Fragments arranged by size:
               733   671   270   168   120   100    78    64    55
CviRI TG'CA
Cuts at:     0   160   562   641  1156  1183  1322  1486  1551
   Size:       160   402    79   515    27   139   164    65
Cuts at:  1551  2259
   Size:        708
   Fragments arranged by size:
               708   515   402   164   160   139    79    65    27
DpnI GA'TC
Cuts at:     0   288   972  1538  2030  2259
   Size:       288   684   566   492   229
   Fragments arranged by size:
               684   566   492   288   229
DraIII CAC_nnn'GTG
Cuts at:     0  1557  2259
   Size:      1557   702
DrdI GACnn_nn'nnGTC
Cuts at:     0  1185  2259
   Size:      1185  1074
DrdII GAACCA
Cuts at:     0   364  1285  2259
   Size:       364   921   974
   Fragments arranged by size:
               974   921   364
DsaI C'CryG_G
Cuts at:     0  1090  1348  1453  2259
   Size:      1090   258   105   806
   Fragments arranged by size:
              1090   806   258   105
EaeI y'GGCC_r
Cuts at:     0   270   490  2259
   Size:       270   220  1769
   Fragments arranged by size:
              1769   270   220
```

FIG. 14G

```
EagI C'GGCC_G
Cuts at:    0    270   2259
   Size:       270   1989
EarI CTCTTCn'nnn_
Cuts at:    0    15    295   1711  2259
   Size:       15   280   1416   548
   Fragments arranged by size:
              1416   548   280    15
EcoNI CCTnn'n_nnAGG
Cuts at:    0    67   2208  2259
   Size:       67   2141    51
   Fragments arranged by size:
              2141    67    51
EcoO109I rG'GnC_Cy
Cuts at:    0   791   932   1031  2145  2259
   Size:      791   141    99   1114   114
   Fragments arranged by size:
              1114   791   141   114    99
EcoRI G'AATT_C
Cuts at:    0   1497  2259
   Size:      1497   762
FauI CCCGCnnnn'nn_
Cuts at:    0    26   1241  2086  2140  2259
   Size:       26  1215   845    54   119
   Fragments arranged by size:
              1215   845   119    54    26
FokI GGATGnnnnnnnnn'nnnn_
Cuts at:    0   1011  1239  1434  1671  2218  2259
   Size:     1011   228   195   237   547    41
   Fragments arranged by size:
              1011   547   237   228   195    41
FspI TGC'GCA
Cuts at:    0   524   1110  2259
   Size:      524   586   1149
   Fragments arranged by size:
              1149   586   524
GdiII y'GGCC_G
Cuts at:    0   270   2259
   Size:      270   1989
HaeI wGG'CCw
Cuts at:    0   397   492   1164  2259
   Size:      397    95   672   1095
   Fragments arranged by size:
              1095   672   397    95
```

FIG. 14H

```
HgiEII ACCnnnnnnGGT
Cuts at:    0    230    2259
   Size:       230   2029
HhaI G_CG'C
Cuts at:    0    525   1064   1089   1111   2259
   Size:       525    539     25     22    1148
   Fragments arranged by size:
              1148    539    525     25     22
Hin4I GAbnnnnnvTC
Cuts at:    0     83    171   1235   1541   1791   2259
   Size:        83     88   1064    306    250    468
   Fragments arranged by size:
              1064    468    306    250     88     83
HincII GTy'rAC
Cuts at:    0   1469   2259
   Size:      1469    790
HinfI G'AnT_C
Cuts at:    0    305    987   2173   2259
   Size:       305    682   1186     86
   Fragments arranged by size:
              1186    682    305     86
HphI GGTGAnnnnnnn_n'
Cuts at:    0   1373   1797   2259
   Size:      1373    424    462
   Fragments arranged by size:
              1373    462    424
MaeIII 'GTnAC_
Cuts at:    0    221    433    862   1617   1679   1784   1803   2039
   Size:       221    212    429    755     62    105     19    236
Cuts at: 2039   2259
   Size:       220
   Fragments arranged by size:
               755    429    236    221    220    212    105     62     19
MboII GAAGAnnnnnnn_n'
Cuts at:    0      2    151    312    353    491    980   1728   1912
   Size:         2    149    161     41    138    489    748    184
Cuts at: 1912   2259
   Size:       347
   Fragments arranged by size:
               748    489    347    184    161    149    138     41
                 2
```

FIG. 14I

MscI TGG'CCA
Cuts at:   0    492   2259
  Size:      492   1767
MslI CAynn'nnrTG
Cuts at:   0    1422  1452  2259
  Size:      1422  30    807
  Fragments arranged by size:
             1422  807   30
MspA1I CmG'CkG
Cuts at:   0    282   557   1050  2181  2259
  Size:      282   275   493   1131  78
  Fragments arranged by size:
             1131  493   282   275   78
MwoI GCnn_nnn'nnGC
Cuts at:   0    201   210   394   470   810   1068  1135  1138
  Size:      201   9     184   76    340   258   67    3
Cuts at:   1138  1650  1768  2259
  Size:      512   118   491
  Fragments arranged by size:
             512   491   340   258   201   184   118   76   67   9   3
NciI CC's_GG
Cuts at:   0    192   413   714   788   789   1534  1625  1920
  Size:      192   221   301   74    1     745   91    295
Cuts at:   1920  2259
  Size:      339
  Fragments arranged by size:
             745   339   301   295   221   192   91    74    1
NcoI C'CATG_G
Cuts at:   0    1453  2259
  Size:      1453  806
NgoAIV G'CCGG_C
Cuts at:   0    1117  2259
  Size:      1117  1142
NlaIII _CATG'
Cuts at:   0    5    155   804   1457  1830  2105  2259
  Size:      5    150   649   653   373   275   154
  Fragments arranged by size:
             653   649   373   275   154   150   5

FIG. 14J

PflMI CCAn_nnn'nTGG
Cuts at:   0   1577   2259
   Size:   1577   682
Psp5II rG'GwC_Cy
Cuts at:   0   791   932   2259
   Size:   791   141   1327
   Fragments arranged by size:
      1327   791   141
PstI C_TGCA'G
Cuts at:   0   1158   2259
   Size:   1158   1101
PvuII CAG'CTG
Cuts at:   0   557   2181   2259
   Size:   557   1624   78
   Fragments arranged by size:
      1624   557   78
RcaI T'CATG_A
Cuts at:   0   2101   2259
   Size:   2101   158
RsaI GT'AC
Cuts at:   0   261   680   999   1014   2259
   Size:   261   419   319   15   1245
   Fragments arranged by size:
      1245   419   319   261   15
SanDI GG'GwC_CC
Cuts at:   0   791   2259
   Size:   791   1468
SapI GCTCTTCn'nnn_
Cuts at:   0   15   2259
   Size:   15   2244
Sau3AI 'GATC_
Cuts at:   0   286   970   1536   2028   2259
   Size:   286   684   566   492   231
   Fragments arranged by size:
      684   566   492   286   231
SfaNI GCATCnnnnn'nnnn_
Cuts at:   0   206   938   1192   1202   2259
   Size:   206   732   254   10   1057
   Fragments arranged by size:
      1057   732   254   206   10
SfcI C'TryA_G
Cuts at:   0   334   427   1154   2259
   Size:   334   93   727   1105
   Fragments arranged by size:
      1105   727   334   93

FIG. 14K

```
SmaI CCC'GGG
Cuts at:      0    789   2259
   Size:       789   1470
Sse8647I AG'GwC_CT
Cuts at:      0    932   2259
   Size:       932   1327
SspI AAT'ATT
Cuts at:      0    2022  2259
   Size:       2022  237
StuI AGG'CCT
Cuts at:      0    397   2259
   Size:       397   1862
StyI C'CwwG_G
Cuts at:      0    398   1453  1997  2259
   Size:       398   1055  544   262
   Fragments arranged by size:
               1055  544   398   262
TaqI T'CG_A
Cuts at:      0    77    377   749   2259
   Size:       77    300   372   1510
   Fragments arranged by size:
               1510  372   300   77
TauI GCsGC
Cuts at:      0    116   202   270   1065  2259
   Size:       116   86    68    795   1194
   Fragments arranged by size:
               1194  795   116   86    68
TfiI G'AwT_C
Cuts at:      0    305   987   2173  2259
   Size:       305   682   1186  86
   Fragments arranged by size:
               1186  682   305   86
ThaI CG'CG
Cuts at:      0    201   1064  2259
   Size:       201   863   1195
   Fragments arranged by size:
               1195  863   201
Tsp45I 'GTsAC_
Cuts at:      0    221   862   1679  1784  1803  2039  2259
   Size:       221   641   817   105   19    236   220
   Fragments arranged by size:
               817   641   236   221   220   105   19
```

FIG. 14L

Tsp509I 'AATT_
Cuts at:   0    495   1488   1497   1731   2244   2259
  Size:   495   993    9     234    513    15
  Fragments arranged by size:
           993   513   495   234    15     9
Tth111I GACn'n_nGTC
Cuts at:   0    49    2259
  Size:   49    2210
Tth111II CAArCAnnnnnnnnn_nn'
Cuts at:   0    234   577   675   1452   1922   2259
  Size:   234   343   98    777    470    337
  Fragments arranged by size:
           777   470   343   337    234    98
UbaCI wGTACw
Cuts at:   0    261   680   2259
  Size:   261   419   1579
  Fragments arranged by size:
          1579   419   261
XcmI CCAnnnn_n'nnnnTGG
Cuts at:   0    396   1829   2259
  Size:   396   1433   430
  Fragments arranged by size:
          1433   430   396
XmnI GAAnn'nnTTC
Cuts at:   0    9    348   2259
  Size:    9    339   1911
  Fragments arranged by size:
          1911   339    9

Enzymes that do cut and were not excluded:

| | | | | | | | |
|---|---|---|---|---|---|---|---|
| AceIII | AlwI | AlwNI | ApaLI | ApoI | AvaI | AvaII | BaeI |
| BamHI | BanI | BanII | BccI | BcefI | BcgI | BfiI | BglI |
| BglII | BmgI | BpII | BpmI | Bpu10I | BsaI | BsaWI | BsbI |
| BscGI | BseRI | BsgI | BsiEI | BsiHKAI | BslI | BsmI | BsmAI |
| BsmFI | Bsp24I | Bsp1286I | BspGI | BspMI | BsrI | BsrDI | BsrFI |
| BssSI | BstXI | BstYI | Bsu36I | Cac8I | CjeI | CviRI | DpnI |
| DraIII | DrdI | DrdII | DsaI | EaeI | EagI | EarI | EcoNI |
| EcoO109I | EcoRI | FauI | FokI | FspI | GdiII | HaeI | HgiEII |
| HhaI | Hin4I | HincII | HinfI | HphI | MaeIII | MboII | MscI |
| MslI | MspAlI | MwoI | NciI | NcoI | NgoAIV | NlaIII | PflMI |
| Psp5II | PstI | PvuII | RcaI | RsaI | SanDI | SapI | Sau3AI |
| SfaNI | SfcI | SmaI | Sse8647I | SspI | StuI | StyI | TaqI |
| TauI | TfiI | ThaI | Tsp45I | Tsp509I | Tth111I | Tth111II | UbaCI |
| XcmI | XmnI | | | | | | |

FIG. 14M

Enzymes that do not cut:

| | | | | | | | |
|---|---|---|---|---|---|---|---|
| AatII | AccI | AflII | AflIII | AhdI | ApaI | ApaBI | AscI |
| AvrII | BbsI | Bce83I | BclI | BfaI | Bpu1102I | BsaAI | BsaBI |
| BsaHI | BsaXI | BsmBI | BspEI | BspLU11I | BsrBI | BsrGI | BssHII |
| Bst1107I | BstEII | ClaI | DraI | EciI | Eco47III | Eco57I | EcoRV |
| FseI | HaeII | HgaI | HindIII | HpaI | KpnI | MaeII | MluI |
| MmeI | MseI | MunI | NarI | NdeI | NheI | NotI | NruI |
| NsiI | NspI | NspV | PacI | Pfl1108I | PinAI | PleI | PmeI |
| PmlI | PshAI | Psp1406I | PvuI | RleAI | RsrII | SacI | SacII |
| SalI | ScaI | SexAI | SfiI | SgfI | SgrAI | SnaBI | SpeI |
| SphI | SrfI | Sse8387I | SunI | SwaI | TaqII | TaqII | VspI |
| XbaI | XhoI | | | | | | |

Enzymes excluded; MinCuts: 1 MaxCuts: 10

| | | | | | | | |
|---|---|---|---|---|---|---|---|
| AciI | AluI | BbvI | BsaJI | BsoFI | CjeI | CjePI | CjePI |
| CviJI | DdeI | EcoRII | HaeIII | MnlI | MspI | NlaIV | Sau96I |
| ScrFI | TseI | TspRI | | | | | |

FIG. 15A (Linear) MAPSORT of: bovlactof.gb_om  check: 2217  from: 1 to: 2351
LOCUS    BOVLACTOF    2351 bp ss-mRNA         MAM
DEFINITION  Bovine lactoferrin mRNA, complete cds.
ACCESSION  M63502
KEYWORDS   lactoferrin.
SOURCE    B.taurus, cDNA to mRNA.
  ORGANISM  Bos taurus . . .
Mismatch: 0  MinCuts = 1  MaxCuts: 10
With 209 enzymes: *

```
AceIII  CAGCTCnnnnnnn'nnnn_
Cuts at:    0    494    526    969    1553    1841    2216    2351
   Size:       494    32    443    584    288    375    135
   Fragments arranged by size:
              584    494    443    375    288    135    32
AflIII  A'CryG_T
Cuts at:    0    1913    2351
   Size:       1913    438
AhdI  GACnn_n'nnGTC
Cuts at:    0    1460    2351
   Size:       1460    891
AlwI  GGATCnnnn'n_
Cuts at:    0    480    1019    1032    2351
   Size:       480    539    13    1319
   Fragments arranged by size:
              1319    539    480    13
AlwNI  CAG_nnn'CTG
Cuts at:    0    1600    1631    1928    1946    2351
   Size:       1600    31    297    18    405
   Fragments arranged by size:
              1600    405    297    31    18
ApoI  r'AATT_y
Cuts at:    0    549    1442    1551    2351
   Size:       549    893    109    800
   Fragments arranged by size:
              893    800    549    109
AvaI  C'yCGr_G
Cuts at:    0    101    522    652    2351
   Size:       101    421    130    1699
   Fragments arranged by size:
              1699    421    130    101
```

FIG. 15B

AvaII G'GwC_C
Cuts at:   0    305    416    460    770    845    986    1149    2244
  Size:       305    111    44    310    75    141    163    1095
Cuts at: 2244  2351
  Size:       107
  Fragments arranged by size:
              1095   310   305   163   141   111   107   75   44
BamHI G'GATC_C
Cuts at:   0    1024   2351
  Size:      1024   1327
BanI G'GyrC_C
Cuts at:   0    678    806    1319    1393    1690    1824    2351
  Size:       678    128    513    74    297    134    527
  Fragments arranged by size:
              678   527   513   297   134   128   74
BanII G_rGCy'C
Cuts at:   0    80    529    1062    1435    2351
  Size:       80    449    533    373    916
  Fragments arranged by size:
              916   533   449   373   80
BbsI GAAGACnn'nnnn_
Cuts at:   0    895    2351
  Size:       895    1456
BbvI GCAGCnnnnnnnn'nnnn_
Cuts at:   0    83    342    409    412    1842    1915    1920    2351
  Size:       83    259    67    3    1430    73    5    431
  Fragments arranged by size:
              1430   431   259   83   73   67   5   3
BccI CCATC
Cuts at:   0    120    128    162    278    881    1283    1823    2351
  Size:       120    8    34    116    603    402    540    528
  Fragments arranged by size:
              603   540   528   402   120   116   34   8
Bce83I CTTGAGnnnnnnnnnnnnnn_nn'
Cuts at:   0    524    2351
  Size:       524    1827
BcefI ACGGCnnnnnnnnnnnn'n_
Cuts at:   0    370    1129    1231    1387    1462    2113    2351
  Size:       370    759    102    156    75    651    238
  Fragments arranged by size:
              759   651   370   238   156   102   75
BfaI C'TA_G
Cuts at:   0    1365    2183    2351
  Size:      1365    818    168
  Fragments arranged by size:
              1365   818   168

FIG. 15C

BfiI ACTGGG
Cuts at:    0   1776   2351
   Size:    1776   575

BglI GCCn_nnn'nGGC
Cuts at:    0   448   1578   1822   2351
   Size:    448   1130   244   529
   Fragments arranged by size:
          1130   529   448   244

BglII A'GATC_T
Cuts at:    0   337   2351
   Size:    337   2014

BmgI GkGCCC
Cuts at:    0   1572   1646   2351
   Size:    1572   74   705
   Fragments arranged by size:
          1572   705   74

BpmI CTGGAGnnnnnnnnnnnnnnnn_nn'
Cuts at:    0   516   727   2216   2351
   Size:    516   211   1489   135
   Fragments arranged by size:
          1489   516   211   135

Bpu10I CC'TnA_GC
Cuts at:    0   1699   2202   2351
   Size:    1699   503   149
   Fragments arranged by size:
          1699   503   149

BsaI GGTCTCn'nnnn_
Cuts at:    0   1373   2351
   Size:    1373   978

BsaAI yAC'GTr
Cuts at:    0   1916   2351
   Size:    1916   435

BsaHI Gr'CG_yC
Cuts at:    0   32   807   1218   2351
   Size:    32   775   411   1133
   Fragments arranged by size:
          1133   775   411   32

BsaWI w'CCGG_w
Cuts at:    0   15   1339   2351
   Size:    15   1324   1012
   Fragments arranged by size:
          1324   1012   15

BsaXI ACnnnnnCTCC
Cuts at:    0   634   1058   2351
   Size:    634   424   1293
   Fragments arranged by size:
          1293   634   424

FIG. 15D

BsbI CAACAC
Cuts at:    0    2029   2351
  Size:   2029    322
BscGI CCCGT
Cuts at:    0    449    498    702   2351
  Size:    449    49     204   1649
  Fragments arranged by size:
          1649   449    204    49
BseRI GAGGAGnnnnnnnn_nn'
Cuts at:    0    638   1119   1170   2198   2351
  Size:    638   481    51    1028    153
  Fragments arranged by size:
          1028   638   481    153     51
BsiHKAI G_wGCw'C
Cuts at:    0    191   1767   2351
  Size:    191   1576   584
  Fragments arranged by size:
          1576   584    191
BsmAI GTCTCn'nnnn_
Cuts at:    0    361    703    723    949   1373   1897   2351
  Size:    361   342    20    226    424    524    454
  Fragments arranged by size:
           524   454   424    361    342    226     20
BsmBI CGTCTCn'nnnn_
Cuts at:    0    703    723   2351
  Size:    703    20   1628
  Fragments arranged by size:
          1628   703    20
BsoFI GC'n_GC
Cuts at:    0    97    155    321    331    401    423   1193   1856
  Size:    97    58    166    10     70     22    770    663
Cuts at:  1856  1909   1929   2351
  Size:    53    20    422
  Fragments arranged by size:
           770   663   422    166    97     70     58     53     22     20     10
Bsp24I GACnnnnnnTGGnnnnnnn_nnnnn'
Cuts at:    0    76    108    260    292    590    622    882    914
  Size:    76    32    152    32    298    32    260    32
Cuts at:   914  1725   1757   2351
  Size:    811    32    594
  Fragments arranged by size:
           811   594   298    260    152    76     32     32     32     32     32

FIG. 15E

Bsp1286I G_dGCh'C
Cuts at:   0    80   191   529   1062   1435   1574   1648   1767
  Size:     80   111   338   533    373    139     74    119
Cuts at:  1767  2351
  Size:    584
  Fragments arranged by size:
           584   533   373   338   139   119   111    80    74

BspEI T'CCGG_A
Cuts at:   0    15   2351
  Size:    15   2336

BspGI CTGGAC
Cuts at:   0    416   511   1634   2351
  Size:    416    95   1123    717
  Fragments arranged by size:
          1123   717   416    95

BspMI ACCTGCnnnn'nnnn_
Cuts at:   0    448   997   2351
  Size:    448   549   1354
  Fragments arranged by size:
          1354   549   448

BsrI ACTG_Gn'
Cuts at:   0    324   635   773   810   1779   2351
  Size:    324   311   138    37   969    572
  Fragments arranged by size:
           969   572   324   311   138    37

BsrBI GAG'CGG
Cuts at:   0    1192   2351
  Size:   1192   1159

BsrDI GCAATG_nn'
Cuts at:   0    2101   2351
  Size:   2101    250

BstXI CCAn_nnnn'nTGG
Cuts at:   0    963   2351
  Size:    963   1388

BstYI r'GATC_y
Cuts at:   0    337   1024   2351
  Size:    337   687   1327
  Fragments arranged by size:
          1327   687   337

Bsu36I CC'TnA_GG
Cuts at:   0    1089   1153   2351
  Size:   1089    64   1198
  Fragments arranged by size:
          1198   1089    64

FIG. 15F

```
CviRI TG'CA
Cuts at:     0    425   577   616   695   1237  1491  1770  2174
   Size:       425   152   39    79    542   254   279   404
Cuts at:  2174  2351
   Size:       177
   Fragments arranged by size:
               542   425   404   279   254   177   152   79    39
DpnI GA'TC
Cuts at:     0    339   474   897   1026  1518  2351
   Size:       339   135   423   129   492   833
   Fragments arranged by size:
               833   492   423   339   135   129
DraIII CAC_nnn'GTG
Cuts at:     0    1886  2035  2351
   Size:       1886  149   316
   Fragments arranged by size:
               1886  316   149
DrdI GACnn_nn'nnGTC
Cuts at:     0    353   1239  2351
   Size:       353   886   1112
   Fragments arranged by size:
               1112  886   353
DrdII GAACCA
Cuts at:     0    146   634   659   2351
   Size:       146   488   25    1692
   Fragments arranged by size:
               1692  488   146   25
DsaI C'CryG_G
Cuts at:     0    1144  1213  1402  1477  1507  2351
   Size:       1144  69    189   75    30    844
   Fragments arranged by size:
               1144  844   189   75    69    30
EaeI y'GGCC_r
Cuts at:     0    321   382   977   1193  2041  2098  2351
   Size:       321   61    595   216   848   57    253
   Fragments arranged by size:
               848   595   321   253   216   61    57
```

FIG. 15G

EarI CTCTTCn'nnn_
Cuts at:     0     54    2351
   Size:         54    2297
EciI TCCGCC
Cuts at:     0    259    2351
   Size:        259    2092
Eco57I CTGAAGnnnnnnnnnnnnnnn_nn'
Cuts at:     0   1787   2283   2351
   Size:       1787    496     68
   Fragments arranged by size:
               1787    496     68
EcoNI CCTnn'n_nnAGG
Cuts at:     0    206    840   1698   2351
   Size:        206    634    858    653
   Fragments arranged by size:
                858    653    634    206
EcoO109I rG'GnC_Cy
Cuts at:     0    305    845    986   1149   1628   2244   2351
   Size:        305    540    141    163    479    616    107
   Fragments arranged by size:
                616    540    479    305    163    141    107
EcoRI G'AATT_C
Cuts at:     0   1442   1551   2351
   Size:       1442    109    800
   Fragments arranged by size:
               1442    800    109
FauI CCCGCnnnn'nn_
Cuts at:     0     65    205    290   1071   1295   2140   2351
   Size:         65    140     85    781    224    845    211
   Fragments arranged by size:
                845    781    224    211    140     85     65
FokI GGATGnnnnnnnnn'nnnn_
Cuts at:     0    185    273    288    462    828    891   1293   1488
   Size:        185     88     15    174    366     63    402    195
Cuts at:  1488   2351
   Size:        863
   Fragments arranged by size:
                863    402    366    195    185    174     88     63

FspI TGC'GCA
Cuts at:    0    1541   2351
  Size:   1541    810
GdiII y'GGCC_G
Cuts at:    0    321   382   977   1193   2098   2351
  Size:    321    61   595   216    905    253
  Fragments arranged by size:
           905   595   321   253   216    61
HaeI wGG'CCw
Cuts at:    0    1315   2043   2351
  Size:   1315    728    308
  Fragments arranged by size:
          1315    728    308
HaeII r_GCGC'y
Cuts at:    0    810   1050   2351
  Size:    810    240   1301
  Fragments arranged by size:
          1301    810    240
HgaI GACGCnnnnn'nnnnn_
Cuts at:    0    40    1207   2351
  Size:     40   1167   1144
  Fragments arranged by size:
          1167   1144    40
HgiEII ACCnnnnnnGGT
Cuts at:    0    275   2351
  Size:    275   2076
HhaI G_CG'C
Cuts at:    0    809   920   1049   1118   1542   2151   2239   2351
  Size:    809   111   129    69    424    609    88    112
  Fragments arranged by size:
           809   609   424   129   112   111    88    69
Hin4I GAbnnnnnnvTC
Cuts at:    0    1289   1459   1588   1845   2351
  Size:   1289    170    129    257    506
  Fragments arranged by size:
          1289    506    257    170    129
HincII GTy'rAC
Cuts at:    0    609   1523   2351
  Size:    609   914    828
  Fragments arranged by size:
           914   828    609

FIG. 15I

HindIII A'AGCT_T
Cuts at:    0    903   2351
  Size:       903   1448
HinfI G'AnT_C
Cuts at:    0    19    354   487   516   1002  1041  1597  1790
  Size:       19    335   133   29    486   39    556   193
Cuts at:  1790  1877  2351
  Size:       87    474
  Fragments arranged by size:
            556   486   474   335   193   133   87    39    29    19
HphI GGTGAnnnnnnnn_n'
Cuts at:    0    191   1121  2351
  Size:       191   930   1230
  Fragments arranged by size:
            1230  930   191
KpnI G_GTAC'C
Cuts at:    0    1397  2351
  Size:       1397  954
MaeII A'CG_T
Cuts at:    0    112   712   1201  1705  1714  1915  2064  2351
  Size:       112   600   489   504   9     201   149   287
  Fragments arranged by size:
            600   504   489   287   201   149   112   9
MaeIII 'GTnAC_
Cuts at:    0    266   517   1202  1838  2093  2351
  Size:       266   251   685   636   255   258
  Fragments arranged by size:
            685   636   266   258   255   251
MboII GAAGAnnnnnnn_n'
Cuts at:    0    41    188   404   545   900   1094  1175  2082
  Size:       41    147   216   141   355   194   81    907
Cuts at:  2082  2351
  Size:       269
  Fragments arranged by size:
            907   355   269   216   194   147   141   81    41

FIG. 15J

MmeI TCCrACnnnnnnnnnnnnnnnnnnnn_nn'
Cuts at:    0    2248    2351
  Size:    2248    103
MscI TGG'CCA
Cuts at:    0    2043    2351
  Size:    2043    308
MseI T'TA_A
Cuts at:    0    724    2351
  Size:    724    1627
MslI CAynn'nnrTG
Cuts at:    0    204    373    480    1476    1506    2351
  Size:    204    169    107    996    30    845
  Fragments arranged by size:
           996    845    204    169    107    30
MspI C'CG_G
Cuts at:    0    16    237    302    431    653    976    1340    1678
  Size:    16    221    65    129    222    323    364    338
Cuts at:    1678    1974    2351
  Size:    296    377
  Fragments arranged by size:
           377    364    338    323    296    222    221    129    65    16
MspAlI CmG'CkG
Cuts at:    0    413    422    465    565    2351
  Size:    413    9    43    100    1786
  Fragments arranged by size:
           1786    413    100    43    9
NarI GG'CG_CC
Cuts at:    0    807    2351
  Size:    807    1544
NciI CC's_GG
Cuts at:    0    238    303    653    654    976    1679    1974    2351
  Size:    238    65    350    1    322    703    295    377
  Fragments arranged by size:
           703    377    350    322    295    238    65    1
NcoI C'CATG_G
Cuts at:    0    1507    2351
  Size:    1507    844
NheI G'CTAG_C
Cuts at:    0    2182    2351
  Size:    2182    169
NlaIII _CATG'
Cuts at:    0    44    287    858    1441    1511    2351
  Size:    44    243    571    583    70    840
  Fragments arranged by size:
           840    583    571    243    70    44

FIG. 15K

PflMI CCAn_nnn'nTGG
Cuts at:    0    1631   2351
  Size:    1631   720
PleI GAGTCnnnn'n_
Cuts at:    0    27    362    524    996    1591   2351
  Size:    27    335    162    472    595    760
  Fragments arranged by size:
           760    595    472    335    162    27
PmlI CAC'GTG
Cuts at:    0    1916   2351
  Size:    1916   435
Psp5II rG'GwC_Cy
Cuts at:    0    305    845    986    1149   2244   2351
  Size:    305    540    141    163    1095   107
  Fragments arranged by size:
           1095   540    305    163    141    107
Psp1406I AA'CG_TT
Cuts at:    0    112    2351
  Size:    112    2239
PstI C_TGCA'G
Cuts at:    0    697    1493   1772   2351
  Size:    697    796    279    579
  Fragments arranged by size:
           796    697    579    279
PvuII CAG'CTG
Cuts at:    0    413    422    565    2351
  Size:    413    9    143    1786
  Fragments arranged by size:
           1786   413    143    9
RsaI GT'AC
Cuts at:    0    125    501    1053   1122   1395   1665   2351
  Size:    125    376    552    69    273    270    686
  Fragments arranged by size:
           686    552    376    273    270    125    69
SanDI GG'GwC_CC
Cuts at:    0    305    2351
  Size:    305    2046
SapI GCTCTTCn'nnn_
Cuts at:    0    54    2351
  Size:    54    2297
Sau3AI 'GATC_
Cuts at:    0    337    472    895    1024   1516   2351
  Size:    337    135    423    129    492    835
  Fragments arranged by size:
           835    492    423    337    135    129

FIG. 15L

ScaI AGT'ACT
Cuts at:  0   1665   2351
  Size:  1665   686

SfaNI GCATCnnnnn'nnnn_
Cuts at:  0   250   251   806   1246   1256   2351
  Size:  250   1   555   440   10   1095
  Fragments arranged by size:
    1095   555   440   250   10   1

SfcI C'TryA_G
Cuts at:  0   693   1489   1768   2351
  Size:  693   796   279   583
  Fragments arranged by size:
    796   693   583   279

SmaI CCC'GGG
Cuts at:  0   654   2351
  Size:  654   1697

SspI AAT'ATT
Cuts at:  0   2076   2351
  Size:  2076   275

StyI C'CwwG_G
Cuts at:  0   71   80   223   452   1507   2351
  Size:  71   9   143   229   1055   844
  Fragments arranged by size:
    1055   844   229   143   71   9

TaqI T'CG_A
Cuts at:  0   116   523   1032   1819   2351
  Size:  116   407   509   787   532
  Fragments arranged by size:
    787   532   509   407   116

TaqII GACCGAnnnnnnnnn_nn'
Cuts at:  0   174   457   2351
  Size:  174   283   1894
  Fragments arranged by size:
    1894   283   174

TauI GCsGC
Cuts at:  0   155   321   1193   2351
  Size:  155   166   872   1158
  Fragments arranged by size:
    1158   872   166   155

TfiI G'AwT_C
Cuts at:  0   487   1041   1790   1877   2351
  Size:  487   554   749   87   474
  Fragments arranged by size:
    749   554   487   474   87

FIG. 15M

ThaI CG'CG
Cuts at:   0    246    1118    2239    2351
  Size:    246    872    1121    112
  Fragments arranged by size:
           1121    872    246    112
TseI GCwGC
Cuts at:   0    97    331    401    423    1856    1909    1929    2351
  Size:    97    234    70    22    1433    53    20    422
  Fragments arranged by size:
           1433    422    234    97    70    53    22    20
Tsp45I 'GTsAC_
Cuts at:   0    266    517    1202    1838    2093    2351
  Size:    266    251    685    636    255    258
  Fragments arranged by size:
           685    636    266    258    255    251
Tsp509I 'AATT_
Cuts at:   0    549    1442    1551    2298    2329    2351
  Size:    549    893    109    747    31    22
  Fragments arranged by size:
           893    747    549    109    31    22
TspRI CAGTGnn'
Cuts at:   0    171    642    742    817    1182    1232    1304    1772
  Size:    171    471    100    75    365    50    72    468
Cuts at:   1772    2036    2351
  Size:    264    315
  Fragments arranged by size:
           471    468    365    315    264    171    100    75    72    50
Tth111I GACn'n_nGTC
Cuts at:   0    88    515    1737    2351
  Size:    88    427    1222    614
  Fragments arranged by size:
           1222    614    427    88
Tth111II CAArCAnnnnnnnnn_nn'
Cuts at:   0    279    604    729    1368    1938    1976    2351
  Size:    279    325    125    639    570    38    375
  Fragments arranged by size:
           639    570    375    325    279    125    38

FIG. 15N

UbaCI wGTACw
Cuts at:  0   1665   2351
   Size:  1665   686
XcmI CCAnnnn_n nnnnTGG
Cuts at:  0   450   2351
   Size:  450   1901
XhoI C'TCGA_G
Cuts at:  0   522   2351
   Size:  522   1829
XmnI GAAnn'nnTTC
Cuts at:  0   48   232   2351
   Size:  48   184   2119
   Fragments arranged by size:
          2119   184   48

Enzymes that do cut and were not excluded:

| AceIII | AflIII | AhdI | AlwI | AlwNI | ApoI | AvaI | AvaII |
|---|---|---|---|---|---|---|---|
| BamHI | BanI | BanII | BbsI | BbvI | BccI | Bce83I | BcefI |
| BfaI | BfiI | BgII | BglII | BmgI | BpmI | Bpu10I | BsaI |
| BsaAI | BsaHI | BsaWI | BsaXI | BsbI | BscGI | BseRI | BsiHKAI |
| BsmAI | BsmBI | BsoFI | Bsp24I | Bsp1286I | BspEI | BspGI | BspMI |
| BsrI | BsrBI | BsrDI | BstXI | BstYI | Bsu36I | CviRI | DpnI |
| DraIII | DrdI | DrdII | DsaI | EaeI | EarI | EciI | Eco57I |
| EcoNI | EcoO109I | EcoRI | FauI | FokI | FspI | GdiII | HaeI |
| HaeII | HgaI | Hgi | EII | HhaI | Hin4I | HincII | HindIII |
| HinfI | HphI | KpnI | MaeII | MaeIII | MboII | MmeI | MscI |
| MseI | MslI | MspI | MspA1I | NarI | NciI | NcoI | NheI |
| NlaIII | PflMI | PleI | PmlI | Psp5II | Psp1406I | PstI | PvuII |
| RsaI | SanDI | SapI | Sau3AI | ScaI | SfaNI | SfcI | SmaI |
| SspI | StyI | TaqI | TaqII | TauI | TfiI | ThaI | TseI |
| Tsp45I | Tsp509I | TspRI | Tth111I | Tth111II | UbaCI | XcmI | XhoI |
| XmnI | | | | | | | |

Enzymes that do not cut:

| AatII | AccI | AflII | ApaI | ApaBI | ApaLI | AscI | AvrII |
|---|---|---|---|---|---|---|---|
| BaeI | BcgI | BcgI | BclI | BplI | Bpu1102I | BsaBI | BsgI |
| BsiEI | BsmI | BspLU11I | BsrFI | BsrGI | BssHII | BssSI | Bst1107I |
| BstEII | ClaI | DraI | EagI | Eco47III | EcoRV | FseI | HpaI |
| MluI | MunI | NdeI | NgoAIV | NotI | NruI | NsiI | NspI |
| NspV | PacI | Pfl1108I | PinAI | PmeI | PshAI | PvuI | RcaI |
| RleAI | RsrII | SacI | SacII | SalI | SexAI | SfiI | SgfI |
| SgrAI | SnaBI | SpeI | SphI | SrfI | Sse8387I | Sse8647I | StuI |
| SunI | SwaI | VspI | XbaI | | | | |

Enzymes excluded; MinCuts: 1   MaxCuts: 10

| AciI | AluI | BsaJI | BslI | BsmFI | Cac8I | CjeI | CjeI |
|---|---|---|---|---|---|---|---|
| CjePI | CjePI | CviJI | DdeI | EcoRII | HaeIII | MnlI | MwoI |
| NlaIV | Sau96I | ScrFI | | | | | |

FIG. 16C

```
                                    Mature ∝-Amylase
       ∝-Amlase Signal Sequence   ┌─────────────────────────────
1) ─────────────────────────────── AlaLeuAlaAlaThrProAlaAspTrpArgSerGlnSer Mature Human Lactoferrin
       Lactoferrin Signal Sequence ┌─────────────────────────────
2) ─────────────────────────────── CysLeuAlaGlyArgArgArgArgSerValGlnTrpCys Mature Recombinant Lactoferrin
       ∝-Amylase Signal Sequence   ┌─────────────────────────────
3) ─────────────────────────────── AlaLeuAlaAlaGlyArgArgArgArgSerValGlnTrp
```

EXPRESSION OF PROCESSED RECOMBINANT LACTOFERRIN AND LACTOFERRIN POLYPEPTIDE FRAGMENTS FROM A FUSION PRODUCT IN ASPERGILLUS

RELATED APPLICATIONS

This application is a continuation of co-pending application U.S. Ser. No. 08/303,009, filed on Nov. 2, 1994, and issued as U.S. Pat. No. 5,571,697 on Nov. 5, 1996, is a continuation-in-part of co-pending application U.S. Ser. No. 08/145,681, filed on Oct. 28, 1993, and issued as U.S. Pat. No. 5,571,691 on Nov. 11, 1996, which is a continuation-in-part of application Ser. No. 07/967,947, filed Oct. 27, 1992, and now abandoned, which in turn is a continuation of application Ser. No. 07/348,270, filed May 5, 1989, now abandoned. U.S. Ser. No. 08/303,009 is also a continuing application of U.S. Ser. No. 08/250,308, filed May 27, 1994, and issued as U.S. Pat. No. 5,571,896 on Nov. 5, 1996, which is a continuation-in-part of application Ser. No. 07/873,304 filed Apr. 24, 1992, now abandoned. The disclosure in all of the above-mentioned patent applications are herein incorporated by reference, with particular reference to the Figures and Examples in these patent applications.

This invention was made with government support under Grant No. HD27965 awarded by the National Institute of Health. The government has certain rights in the invention.

FIELD OF THE INVENTION

The present invention relates generally to the field of iron-binding glycoproteins and related polypeptides, namely lactoferrins. More specifically, the present invention relates to the recombinant production of various lactoferrins and lactoferrin polypeptide fragments in Aspergillus, especially *Aspergillus awamori, niger* and *oryzae*.

BACKGROUND DISCLOSURES

In co-pending patent application U.S. Ser. No. 08/145,681, the cDNA sequences for human lactoferrin was disclosed. Additionally, in the same co-pending patent application U.S. Ser. No. 08/145,681, the cDNA sequences for human lactoferrin were used to produce human lactoferrin in a variety of different organisms, including various fungi, such as *Saccharomyces cerevisiae, Aspergillus nidulans*, and *Aspergillus oryzae*.

DESCRIPTION OF THE PRIOR ART

Lactoferrin (LF) is an iron-binding glycoprotein found in milk and other secretions and body fluids. LF is a member of the transferrin family and is involved in iron binding and delivery in mammals.

LF was originally discovered in milk where it can be secreted at levels up to 7 grams/liter in colostrum. Since that original discovery, LF has been detected in other secreted fluids of humans and other mammals. Those fluids include tears, saliva and mucosal secretions and also in the secondary granules of polymorphonuclear leukocytes.

LF is a 78 kilodalton (kDa) glycoprotein having a bilobal structure with a high degree of homology between the C and N terminal halves which is evident in both the amino acid sequence and the three dimensional structure levels. Each of these lobes can reversibly bind one ferric iron with high affinity and with the concomitant binding of bicarbonate. The biological functions of lactoferrin include static and cidal effects against microbial pathogens, transport of iron, promotion of cell growth, regulation of immune cell function and inflammatory response, and regulation of myelopoiesis. It has been found that the deglycosylated protein retains all biological functions of native LF.

The bactericidal domain from lactoferrin has a broad spectrum of antimicrobial action. Bellamy, W. M. et al., *J. App. Bact.* 73, 472–479 (1992). Although Bellamy et al. report that bovine lactoferrin isolated from milk can provide commercial quantities of the bovine polypeptide by pepsin digestion, the materials used in both studies had a maximum purity of 95%. Bellamy, et al. do not provide information for the large scale production of synthetic human or bovine lactoferrin or lactoferrin polypeptides. Neither does Bellamy et al. discuss methods which provide the ability to produce peptides that are not available by enzyme digestion.

Filamentous fungi have been employed as hosts in the industrial production of extracellular glycoproteins. Certain industrial strains are capable of secreting gram quantities of these proteins. In addition, filamentous fungi are able to correctly perform post-translational modifications of eukaryotic proteins and many proteins have U.S. Food and Drug Administration approval. Furthermore, large scale fermentation technology and downstream processing experience is available. However, there have been reports that lactoferrin is toxic to certain fungi (Valenti, et al, *FEMS Microbiology Letters*, 33:271–275 (1986); Epstein, et al, *Reviews of Infectious Diseases*, 6:96–106 (1984); Soukka, et al, *FEMS Microbiology Letters*, 90:223–228 (1992)) and consequently, workers have not employed fungi universally, particularly for production of lactoferrins.

Production of lactoferrins in filamentous fungi, particularly, Aspergillus, was first reported by the present inventors (Ward, et al, *Gene*, 122:219–223 (1992); Ward, et al., *Biotechnology*, 10:784–789 (1992); Conneely et al., *Production of Recombinant Human Lactoferrin*, PCT/U.S. 93/22348, International Application Number PCT/U.S. 93/03614, having a priority date of Apr. 24, 1992 and published on Nov. 11, 1993; and Conneely, et al., U.S. Ser. No. 08/250,308 filed May 27, 1994, which is a continuing application of U.S. Ser. No. 07/873,304, filed Apr. 24, 1992, now abandoned, all of which are incorporated herein by reference). However, while these processes were a significant breakthrough, they have been limited in their ability to effectively produce large commercial quantities of lactoferrin.

Currently, there is a need for a more efficient and economical way to produce LF, either human, bovine, or porcine, in addition to a way to produce lactoferrin polypeptides. Consequently, there is also a need for the development of an efficient and commercial method for the production of human lactoferrin for nutritional and therapeutic applications and for further investigation into its mechanism of action. The subject invention satisfies this need by providing the production of lactoferrins and lactoferrin polypeptide fragments using the host cells Aspergillus in connection with novel vector constructs and especially methods of producing lactoferrins in Aspergillus host cells, which enables them to produce commercial amounts of recombinant lactoferrins and lactoferrin polypeptide fragments.

SUMMARY OF THE INVENTION

The subject invention provides for the production of lactoferrins and lactoferrin polypeptide fragments using the host cells Aspergillus in combination with novel plasmid constructs. More specifically, the subject invention provides novel vector constructs capable of producing lactoferrins and lactoferrin polypeptide fragments in Aspergillus host cells. More particularly, the subject invention provides for novel plasmid constructs suitable for use with Aspergillus and especially *Aspergillus awamori, niger* and *oryzae* host cells, which enables them to produce large amounts of recombinant lactoferrins and lactoferrin polypeptide fragments.

The subject invention also provides for a novel expression plasmid vector construct which enables the production of lactoferrin and lactoferrin polypeptide fragments. The plasmid vector constructs contain two important components which provide such high levels of lactoferrin to be produced. In addition to a promoter, cDNA coding for protein of choice, a signal sequence, transcription termination sequence and a selectable marker, the plasmid vector construct additionally contains (a) 5' half of a highly expressed endogenous gene whose product is secreted from the *Aspergillus cell*, and (b) a linker sequence whereby there is an endogenous proteolytic enzyme for the linker sequence. The product of this novel plasmid vector construct is a fusion protein comprised of half of the highly expressed gene fused to lactoferrin or lactoferrin polypeptide fragment. The fusion protein thereafter is processed by an endogenous proteolytic enzyme which is preferably specific for the Kex2 peptidase cleavage site. For example, if the glucoamylase promoter from *A. awamori* is used, the vector would also contain the 5' half of the *A. awamori* glucoamylase gene. The lactoferrin produced would be fused to one-half of the glucoamylase gene and would then be processed by an endogenous *A. awamori* proteolytic enzyme which is specific for the Kex2 peptidase cleavage site. As another example, if the glucoamylase promoter from *A. niger* is used, the vector would also contain the 5' half of the *A. niger* glucoamylase gene. The fusion product produced by the vector construct (LF fused to one half of glucoamylase gene) would then be processed by an *A. niger* endogenous proteolytic enzyme specific for the Kex2 peptidase cleavage site releasing the desired lactoferrin protein or LF polypeptide fragment. Also, if *A. oryzae* cells were to be used, the vector construct would contain the *A. oryzae* promoter from the α-amylase gene and a portion of the *A. oryzae* α-amylase gene. The vector would be used to transform *A. oryzae* cells and the fused product (LF fused to half of the α-amylase gene) would be processed by an *A. oryzae* endogenous proteolytic enzyme specific for the Kex2 peptidase cleavage site yielding the desired LF or LF polypeptide fragment.

Thus, the subject invention provides a novel vector plasmid construct for producing LF or LF polypeptide fragments in commercial quantities in any strain of Aspergillus.

Another embodiment of the subject invention comprises the following components operably linked from 5' to 3' to form an expression plasmid vector:

(a) a promoter;
(b) a signal sequence;
(c) 5' portion of a highly expressed endogenous gene whose product is secreted from Aspergillus cells (i.e. glucoamylase gene);
(d) a linker sequence; and
(e) a nucleotide sequence corresponding to the desired lactoferrin or lactoferrin polypeptide fragment.

The above DNA sequences (a) through (e) are then cloned together to form a plasmid. The resulting expression plasmid is used to transform Aspergillus cells which will express the lactoferrin protein or lactoferrin polypeptide fragment (corresponding to the lactoferrin nucleotide sequence inserted into the expression plasmid) fused to one half of the highly expressed endogenous gene, for example, the glucoamylase gene. The LF or LF polypeptide fragment is processed by an endogenous proteolytic enzyme specific for the Kex2 peptidase cleavage site.

Another embodiment of the claimed invention is a process for producing lactoferrin which comprises culturing a transformed Aspergillus fungal cell containing a recombinant plasmid, wherein said plasmid comprises a nucleotide sequence which codes for lactoferrin proteins or lactoferrin polypeptide fragments, wherein said transformed Aspergillus fungal cells are cultured in a suitable nutrient medium until lactoferrin protein is formed as a fusion product and then processed via an endogenous proteolytic enzyme specific for Kex2 peptidase cleavage site, wherein said processed lactoferrin is secreted into the nutrient medium and wherein said lactoferrin is isolated or recovered from the nutrient medium.

The present invention is further defined in that the above mentioned plasmid vector further comprises a promoter, a signal sequence, a 5' portion of the glucoamylase gene, a linker sequence, a transcription termination sequence, and a selectable marker gene. For the purpose of this invention, "linker sequence" and "protease recognition sequence" are used interchangeably.

This expression vector is further defined wherein the promoter which is selected from the genes of the group consisting of alcohol dehydrogenase, α-amylase, glucoamylase, and bena and wherein the promoter is further defined to be from *A. awamori* glucoamylase gene.

The above described process is further defined wherein said promoter is from the glucoamylase gene, wherein said promoter is from the glucoamylase gene of *A. awamori* and wherein the signal sequence is from the *A. awamori* glucoamylase gene. This process is further defined wherein the above described signal sequence further comprises a 5' portion of the glucoamylase gene that is from *A. awamori*.

The above described process can be further defined wherein said promoter is derived from the glucoamylase gene, wherein said promoter is from the glucoamylase gene of *A. niger* and the signal sequence is from the *A. niger* glucoamylase gene. This process is further defined wherein the above described signal sequence further comprises a 5' portion of the glucoamylase gene that is from *A. niger*.

The above described process is still further defined wherein said promoter is from the α-amylase gene, wherein said promoter is from the α-amylase gene of *A. oryzae* and wherein the cDNA sequence corresponding to the signal sequence is from the *A. oryzae* α-amylase gene. This process is further defined wherein the above described signal sequence further comprises a 5' portion of the α-amylase gene that is from *A. oryzae*.

The above described process is further defined wherein the linker sequence is a peptidase recognition sequence. This invention is yet further defined wherein the linker sequence encodes the Kex2 peptidase recognition sequence. For the purpose of this invention, Kex2 peptidase recognition sequence and Kex2 peptidase cleavage site are the same.

The above described process is further defined wherein the transcription termination sequence is selected from the genes of the group consisting of alpha-amylase, glucoamylase, alcohol dehydrogenase and benA. This invention is yet further defined in that the transcription termination sequence is from the glucoamylase gene and wherein the transcription termination sequence is from the glucoamylase gene of *A. niger*.

The above described process is further defined wherein the selectable marker gene is selected from the genes of the group consisting of pyr4, pyrG, amdS, argB, trpC, and phleomycin resistance. This process is yet further defined in that the selectable marker is from the phleomycin resistance gene.

This invention is further defined wherein the lactoferrin protein or lactoferrin polypeptide fragment is human, porcine or bovine lactoferrin protein. The invention is further defined and wherein any lactoferrin product has been deglycosylated.

Another embodiment of the present invention is a plasmid which consists essentially of DNA encoding the amino acids of a human lactoferrin and a plasmid vector for the expression of the DNA in the cell wherein said plasmid is used for expressing the DNA of a human lactoferrin in *Aspergillus awamori* fungal cells. A particular preferred plasmid is defined as one having the characteristics of ATCC Accession Number 74290 and designated Awa LF 24-1 wherein Awa LF 24-1 is *Aspergillus awamori* transformed with expression plasmid pPLF-19 containing DNA encoding human lactoferrin, i.e., Seq. I.D. Listing No. 1 of U.S. Ser. No. 08/145,681, the latter of which is incorporated herein by reference. Another embodiment of this invention is *Aspergillus awamori* fungal cells containing the above described plasmid.

Yet a specific embodiment of the present invention is a process comprising culturing a transformed *Aspergillus awamori, niger* and *oryzae* fungal cell containing a recombinant plasmid, wherein said plasmid comprises a plasmid vector containing:

(a) a promoter from the *A. awamori* glucoamylase gene;

(b) a signal sequence from the *A. awamori* glucoamylase gene;

(c) a 5' portion of a highly expressed endogenous gene, for example, the *A. awamori* glucoamylase gene;

(d) a linker sequence encoding kex2 peptidase cleavage site;

(e) DNA encoding the amino acids for human lactoferrin;

(f) a transcription termination sequence from the *A. niger* glucoamylase gene; and (g) a phleomycin resistance selectable marker gene;

wherein said transformed *Aspergillus awamori, niger* and *oryzae* fungal cells are cultured in a suitable nutrient medium until lactoferrin protein is formed as a fusion product and then processed by an endogenous proteolytic enzyme specific for the Kex2 peptidase cleavage site, wherein said lactoferrin protein is the product of the cDNA encoding the amino acid sequence of human LF and, wherein lactoferrin is secreted into the nutrient medium and isolated therefrom. For the purpose of this invention, "Kex2 peptidase cleavage site" and "kex2 peptidase recognition sequence" are used interchangeably.

Another embodiment of this invention is a method of isolating lactoferrin from fungal nutrient medium comprising culturing a transformed Aspergillus fungal cell containing a recombinant plasmid vector, wherein said plasmid vector comprises a promoter, signal sequences, a 5' portion of the glucoamylase gene, linker sequences, DNA encoding the amino acids of human lactoferrin, transcription termination sequences, and a selectable marker gene and wherein said transformed Aspergillus fungal cells are cultured in a suitable nutrient medium until lactoferrin protein is formed as a fusion product and then processed by an endogenous proteolytic enzyme, and wherein lactoferrin is secreted into the nutrient medium and isolated therefrom.

The above described method of isolating lactoferrin from fungal nutrient medium is further defined wherein the plasmid vector contains a promoter from the *A. awamori* glucoamylase gene, a signal sequence from *A. awamori* glucoamylase gene, a 5' portion of the *A. awamori* glucoamylase gene, a linker sequence encoding kex2 peptidase cleavage site, a transcription termination sequence from the *A. niger* glucoamylase gene, and a phleomycin resistance selectable marker gene.

Another embodiment of this invention is a novel recombinant expression plasmid vector comprising the following components operably linked from 5' to 3':

1) promoter from the *A. awamori* glucoamylase gene;
2) signal sequence from the *A. awamori* glucoamylase gene;
3) 5' portion of the *A. awamori* glucoamylase gene;
4) linker sequence encoding kex2 peptidase cleavage site;
5) a nucleotide sequence encoding the amino acids for human lactoferrin or lactoferrin polypeptide fragments;
6) transcription termination sequence from the *A. niger* glucoamylase gene; and
7) phleomycin resistance selectable marker gene.

The invention also comprises production of the complete and partial sequences of the cDNA for human, bovine or porcine lactoferrins and substitution analogs or allelic variations thereof which code for biologically active polypeptides having homology with a portion of lactoferrin, especially those that are not available from enzyme digests of natural lactoferrins, the method of making polypeptides by use and expression of partial cDNA sequences, and the polypeptide products produced by the methods of this invention. The desired partial sequences can be produced by restriction enzyme cleavage, as for example at the cleavage sites indicated in FIGS. 13, 14, and 15. FIGS. 13 through 15 shown restriction enzyme cleavage sites for the human, bovine and porcine LF cDNA sequence, respectively. The partial sequences may also be synthesized, obtained by PCR amplification, by a combination of cleavage, ligation and synthesis, or by other methods known to those skilled in the art.

The cDNA sequence for porcine lactoferrin (Lydon, J. P., et al., *Biochem. Biophys. ACTA*, 1132:97–99 (1992); Alexander, L. J., et al., *Animal Genetics*, 23:251–256 (1992)) and for bovine lactoferrin (Mead, P. E., et al., *Nucleic Acids Research*, 18:7167 (1990); Pierce, A., et al., *Eur. J. Biochem.*, 196:177–184 (1991)) have since been determined and reported in the literature. The references containing the cDNA sequences for bovine and porcine lactoferrin are herein incorporated into this patent application by reference.

Fragments of polypeptides derived from lactoferrin are also known to be biologically active and they may be produced by the method of the present invention. An N-terminal human lactoferrin fragment, including a bactericidal domain of hLF, was isolated from a pepsin digest of intact hLF. Bellamy, W. M., et al., *Biochem. Biophys. ACTA*, 1121:130–136 (1992). Synthetic 23 and 25 amino acid polypeptides were synthesized and found to have activities similar to the fragment derived by pepsin digestion. The synthesis details, yields and purity of the synthetic peptide were not reported. Bellamy et al. do not provide a practical route to large scale production of the bovine or human lactoferrin polypeptides free of the contaminants resulting from isolation from natural products. These polypeptides fragments may be produced by the method of the present invention, and form a preferred embodiment thereof.

The amino acid sequences and corresponding cDNA sequences for the following disclosures are incorporated herein by reference:

(a) Powell, et al., Nucleic Acids Research, 18(13): 4013 (1990; mammary);

(b) Rey, et al., Nucleic Acids Research, 18(17): 5288 (1990; mammary);

(c) Rado, et al., Blood, 70(4): 989–993 (1987; neutrophil);

(d) Stowell, et al., Biochem. J., 276:349–355 (1991);

(e) Panella, et al., *Cancer Research*, 51: 3037–3043 (1991; mammary); and (f) Johnston, et al., Blood, 79(11): 2998–3006 (1992; leukemic).

Any of these sequences, or modified forms of these sequences may be used in the method of the present invention, the preferred sequence is one having the polypeptide sequence reported to GenBank by the present inventors, and having Accession No. A31000, all of which are incorporated herein by reference.

BRIEF DESCRIPTION OF THE DRAWINGS

So that the manner in which the above recited features, advantages, and objects of the invention, as well as others which will become clear, are obtained and can be understood in detail, more particular descriptions of the invention briefly summarized above may be had by reference to certain embodiments thereof which are illustrated in the appended drawings. These drawings form a part of this specification.

It is to be noted, however, that the appended drawings illustrate preferred embodiments of the invention and therefore not to be considered limiting of its scope. The invention may admit to other equally effective equivalent embodiments.

FIG. 4 presents the results from N-terminal sequencing of the first 10 amino acids of recombinantly produced hLF in *A. awamori*.

FIG. 13 shows restriction enzyme cleavage sites for the human LF cDNA sequence.

FIG. 14 shows restriction enzyme cleavage sites for the bovine LF cDNA sequence.

FIG. 15 shows restriction enzyme cleavage sites for the porcine LF cDNA sequence.

FIG. 16C represents N-terminal amino acid sequence of recombinant hLF produced in *A. oryzae*.

DETAILED DESCRIPTION OF THE INVENTION

Definitions

Figure 1A:
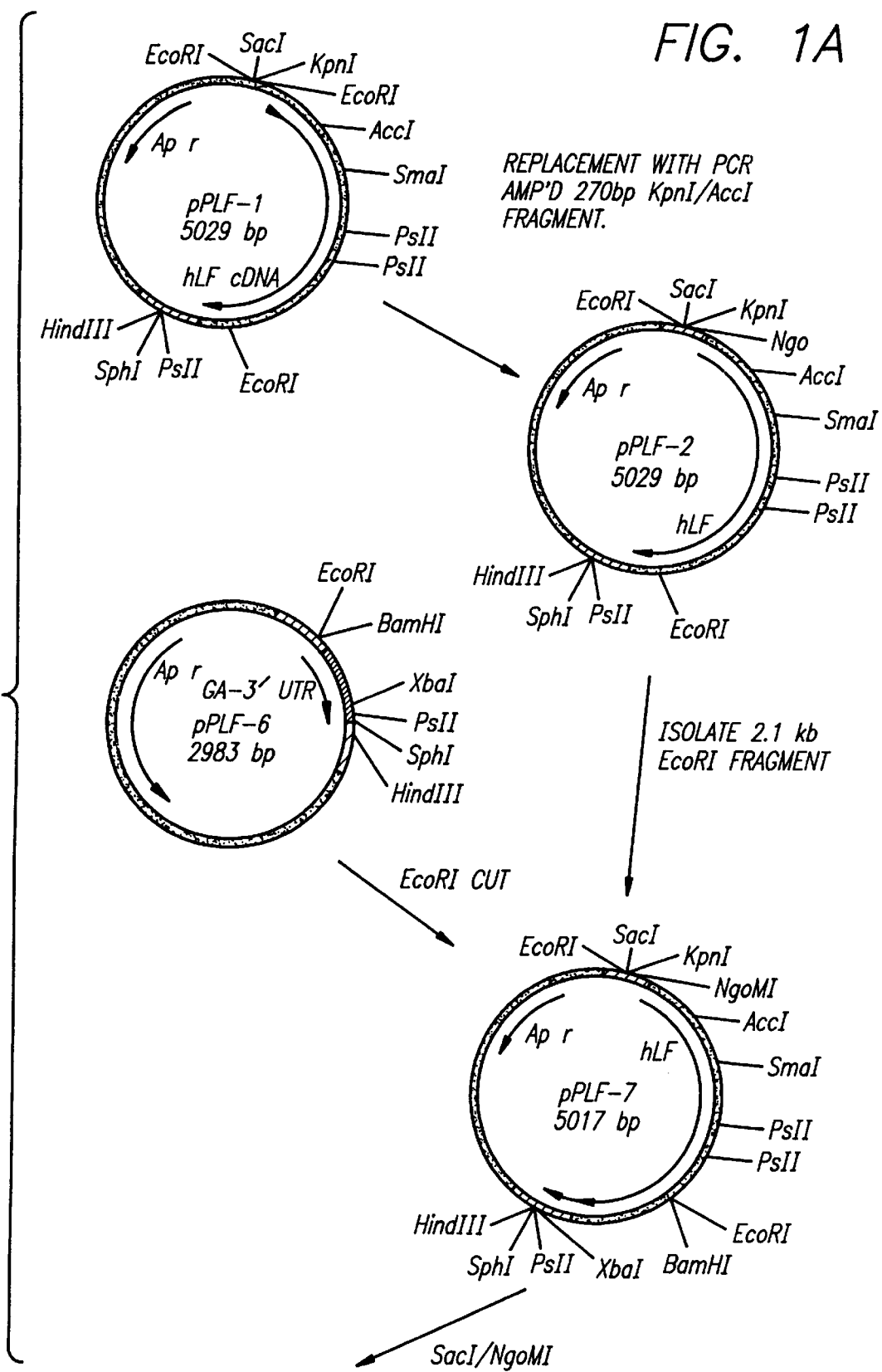
FIG. 1 shows the construction of the plasmid vector containing the hLF cDNA for expression in *Aspergillus awamori* designated "pPLF-19." Abbreviations used in this figure are as follows: Apr: ampicillin resistance; hLF: human lactoferrin; GA: glucoamylase; pGA: promoter from glucoamylase; GA 3'UTR: glucoamylase 3' untranslated region; s.s.: signal sequence; phleo r: phleomycin gene resistance. Example 4 details the construction of this vector.
Figure 1B:
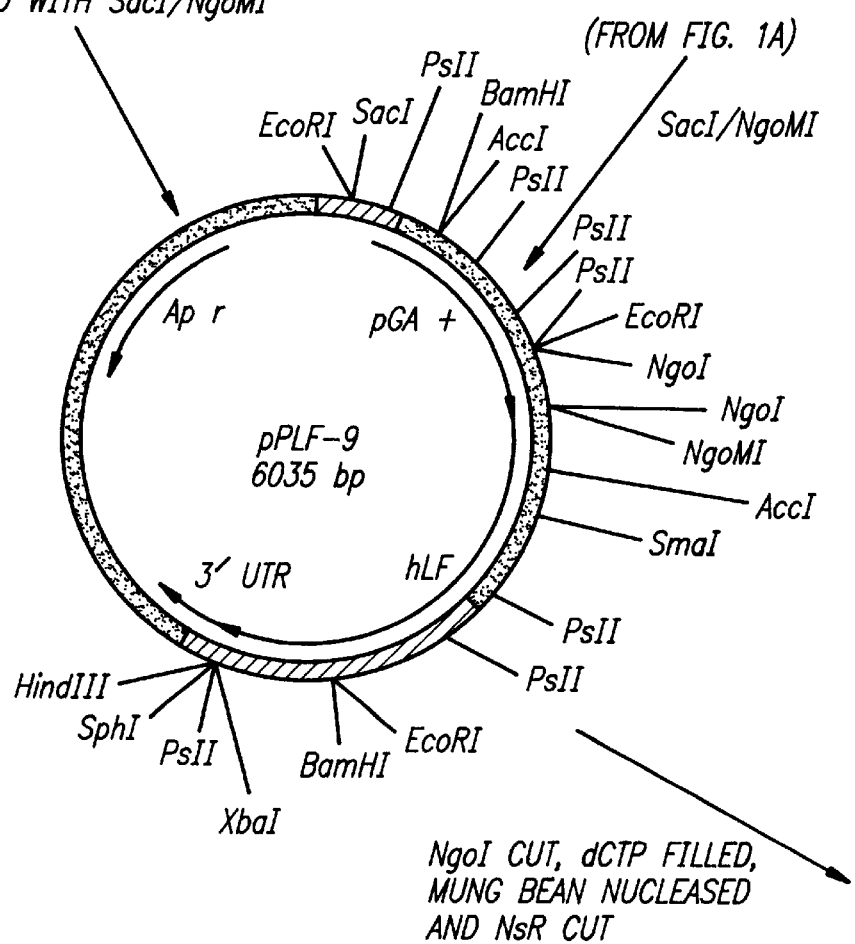
Figure 1C:
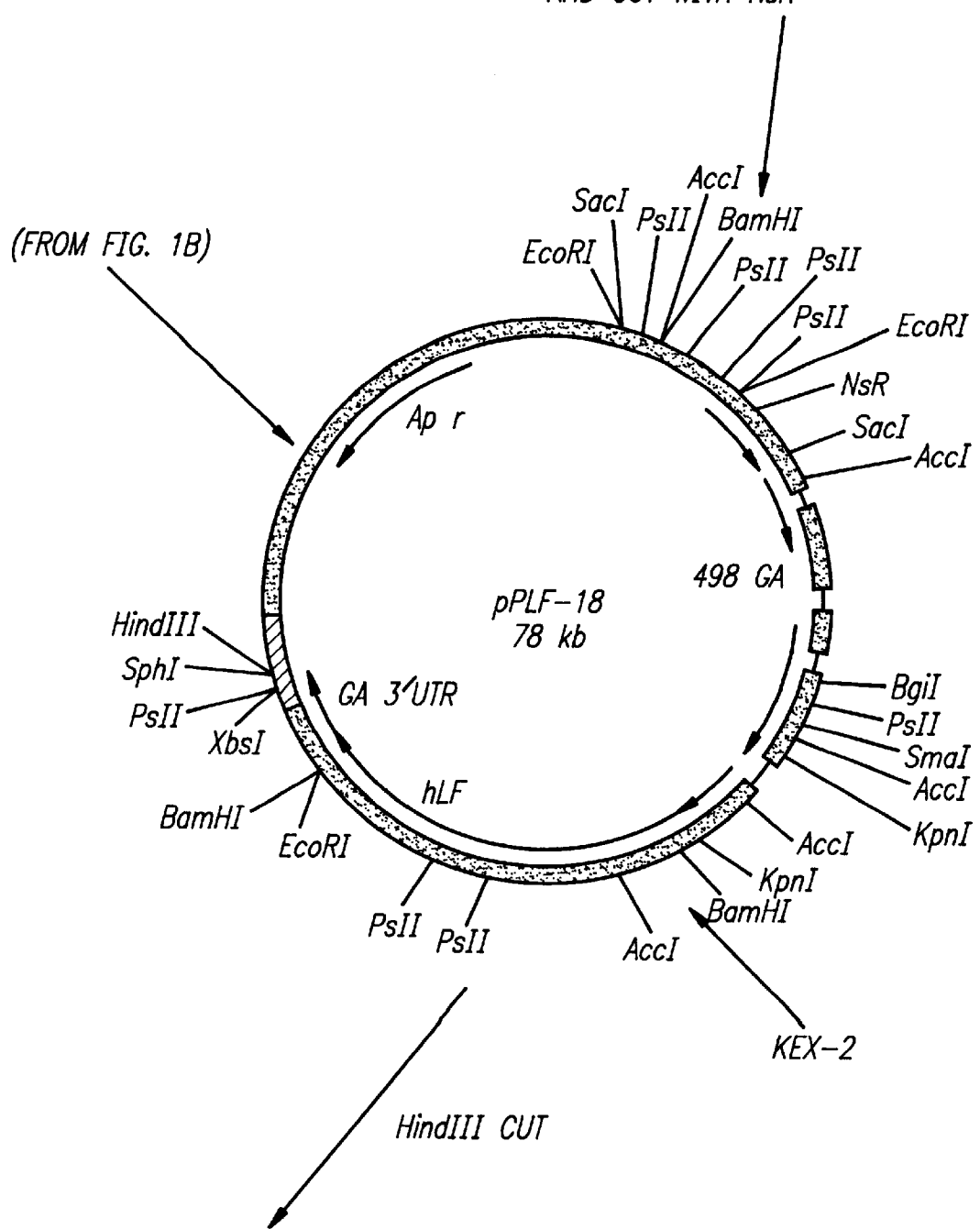
Figure 1D:
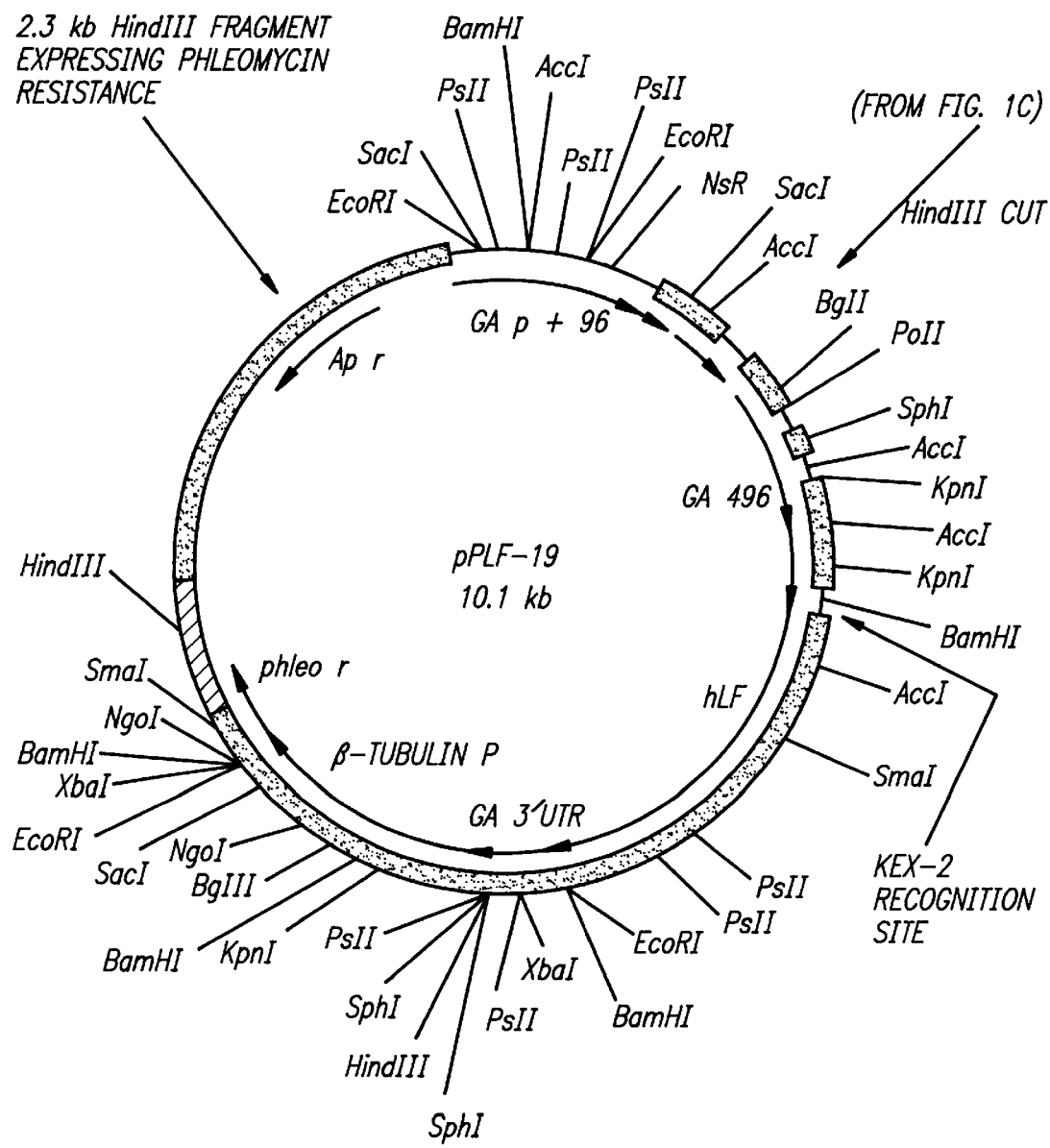

For the purpose of the subject application, the following terms are defined for a better understanding of the invention.

The term "transferrin family" means a family of iron binding proteins including serum transferrin, ovotransferrin and lactoferrin. These proteins are all structurally related.

The term "lactoferrin" means a member of the transferrin family which is found in milk and other secretions. Lactoferrin is an 78 KD iron binding protein.

Additionally, the term "domain" is used to define a functional fragment of the lactoferrin protein or lactoferrin polypeptide which includes all or part of the molecular elements which effect a specified function such as iron binding, bactericidal properties, receptor binding, immune stimulation, etc.

The term "polypeptide" or "polypeptides" means several amino acids attached together to form a small peptide or polypeptide.

The term "substitution analog" or "allelic variation" or "allelic variant" all refer to a DNA sequence which one or more codons specifying one or more amino acids of lactoferrin or a lactoferrin polypeptide are replaced by alternate codons that specify the same amino acid sequence with a different DNA sequence. Where "substitution analog" or "allelic variant" refers to a protein or polypeptide it means the substitution of a small number, generally five or less amino acids as are known to occur in allelic variation in human and other mammalian proteins wherein the biological activity of the protein is maintained. Amino acid substitutions have been reported in the sequences of several published hLF cDNAs which are most likely due to allelic variations. See FIG. 16, and discussion related to this Figure.

The term "vector(s)" means plasmid, cosmid, phage or any other vehicle to allow insertion, propagation and expression of lactoferrin cDNA.

The term "host(s)" means any cell that will allow lactoferrin expression.

The term "promoter(s)" means regulatory DNA sequences that control transcription of the lactoferrin cDNA.

The term "multiple cloning cassette" means a DNA fragment containing unique restriction enzyme cleavage sites for a variety of enzymes allowing insertion of a variety of cDNAs.

The term "transformation" means incorporation permitting expression of heterologous DNA sequences by a cell.

The term "iron binding capacity" means ability to bind Fe. Fully functional human lactoferrin can bind two atoms of iron per molecule of LF.

The term "biological activity or biologically active" means functional activity of lactoferrin as measured by its ability to bind iron, or kill microorganisms, or retard the growth of microorganisms, or to function as an iron transfer protein, or bind to specific receptors, stimulate immune response or regulate myelopoiesis.

The promoter useful in the present invention may be any that allows regulation of the transcription of the lactoferrin cDNA. Preferably, the promoter is selected from the group of alcohol dehydrogenase, α-amylase and glucoamylase genes. Thus, many different promoters are known to those skilled in this art but the inventors prefer to use the glucoamylase promoter isolated from *A. awamori*.

Many different signal sequence and sources of these signal sequences are known to those skilled in this art but the inventors prefer to use the glucoamylase signal sequence plus the 5' portion of the glucoamylase gene derived from *A. awamori*.

The signal sequence useful in the present method may be any that contains a translation initiation codon and secretory signal together with part of a coding region for any highly expressed endogenous gene.

The linker sequence useful in the present method contains a recognition sequence for any proteolytic enzyme, preferably the Kex2 peptidase recognition sequence.

The transcription termination sequence useful in the present method may be any that allows stabilization and correct termination of the lactoferrin mRNA transcripts. Preferably, the transcription termination sequence is derived from the α-amylase, glucoamylase, alcohol dehydrogenase or bena genes. Thus, many different transcription termination sequences are known to those skilled in this art but the inventors prefer using the 3' untranslated region from the glucoamylase gene from *A. niger*.

The selectable marker gene useful in the method of the present invention may be any that permits isolation of cells transformed with a lactoferrin cDNA plasmid. Preferably, the selectable marker gene is selected from pyr4, pyrG, argB, trpC, amdS, or phleomycin resistance genes. Thus, many different selectable markers are known to those skilled in this art but the inventors prefer to use the phleomycin resistance gene.

Additionally, recombinant production of lactoferrin protein has been described above in its preferred embodiments. LF can be produced in a number of sources: cell sources such as Aspergillus; *Saccharomyces cerevisiae, Kluyveromyces lactis*, or *Pichia pastoris*; insect cells such as SF9; and mammalian cells such as Cos cells.

The cells, preferably eukaryotic cells, useful in the present invention are any that allow for integration of a vector, preferably a plasmid comprising the lactoferrin cDNA and expression of the lactoferrin cDNA. Preferably, the eukaryotic cells are filamentous fungal cells or insect cells. Insect cells such as SF9 are useful in the method of the present invention. More preferably, the cells are fungal Aspergillus cells. Most preferably, the eukaryotic cells useful in the present invention are Aspergillus strains, such as *A. oryzae, A. niger, A. nidulans* and *A. awamori*.

The confirmation of the cDNA sequence encoding hLF and the deduced amino acid have been proven by multiple confirmation procedures.

These are:
1. Multiple sequence analyses.
2. Transcription and translation of hLF protein from the cDNA with positive identification using an anti-hLF antibody.

The DNA sequence encoding hLF can be used to prepare recombinant human lactoferrin, thus making available a source of the human lactoferrin for therapeutic and nutritional application. The confirmed cDNA sequence can be used in an appropriate cloning vehicle to replicate the cDNA sequence. Also, the cDNA can be incorporated into a vector system for human lactoferrin production. Other lactoferrin DNA sequences can be substituted for the human lactoferrin cDNA sequence to provide bovine, porcine, equine or other lactoferrins. Partial cDNA sequences can also be employed to give desired lactoferrin derived polypeptides. The expression systems of the invention can be used to provide lactoferrin derived polypeptides that are not available by enzymatic digestion of naturally occurring lactoferrin. The subject invention further provides an expression system for producing lactoferrin and lactoferrin related polypeptides in Aspergillus cells. The invention allows for the production of lactoferrin free of lactoperoxidase, lysozyme, or other proteins that are contaminants of lactoferrin isolated from milk or other natural sources. This invention is not limited to any particular uses of the human cDNA sequence or production of lactoferrin of other species from the appropriate DNA sequences.

The recombinant LF being a protein derived by recombinant techniques can be used in a variety of applications. The human gene can be transferred to mammalian systems such as cows and other agriculturally important animals and expressed in milk. The incorporation of a lactoferrin gene and expression in the milk of animals can combat an iron deficiency typical in piglets. The inclusion of a lactoferrin gene with expression should improve an animal's disease resistance to bacterial and viral infection. The tissue specific expression of human lactoferrin in mammary glands, for instance, would impart the bacteriocidal and virucidal benefit of the expressed gene to young feeding on the milk and would provide a production means for the secreted protein for therapeutic use.

The LF produced by recombinant methods of the subject invention can be used in a variety of products including human or animal foods, as therapeutic additives to enhance iron transport and delivery, and for the virucidal and bacteriocidal qualities, as additives for eyedrops, contact lens and other eye care solutions, topical skin care products, eardrops, mouthwashes, chewing gum and toothpaste. The recombinant LF would provide a safe, naturally occurring product which can be topically applied as well as ingested safely. The bactericidal lactoferrin polypeptides are useful as preservatives in the above listed products, and as therapeutic anti-infection agents. The iron binding polypeptides are useful as iron or other metal ion carrier proteins for nutritional and therapeutic uses, and as bacteriostats and bactericides, especially in products of the types listed above. Each protein may also be used as a nutrition supplement and as a source of amino acids and metals.

Different components of plasmid expression vectors as used to produce recombinant human lactoferrin are presented below and are not meant to be limitations of the present invention in any form. Many different promoters are known to those skilled in this art but the inventors prefer to use the glucoamylase promoter isolated from *A. awamori*. Many different signal sequence and sources of these signal sequences are known to those skilled in this art but the inventors prefer to use the glucoamylase signal sequence plus the 5' portion of the glucoamylase gene derived from *A. awamori*. Many different linker sequences are known to those skilled in this art but the inventors prefer to use a synthetic linker which codes for the Kex2 peptidase cleavage site. Many different transcription termination sequences are known to those skilled in this art but the inventors prefer using the 3' untranslated region from the glucoamylase gene from *A. niger*. Many different selectable markers are known to those skilled in this art but the inventors prefer to use the phleomycin resistance gene.

One of ordinary skill in this art understands and appreciates that a variety of different parameters can be modified while not affecting the quantity or quality of lactoferrin produced by the claimed invention. The following is a list of such parameters that can be altered and yet still not affect the amount and quality of lactoferrin produced: temperature; pH; nutrients required; scale-up considerations; type of equipment used; ratio of oxygen/air used; use of stirred vs. static systems; harvest times, etc.

Different growth and production conditions can be used for the expression of recombinant human lactoferrin in *Aspergillus awamori*. The following descriptions are presented for the purposes of illustrating various conditions which can be used for the expression of hLF in *Aspergillus awamori* and are not meant to be limitations of the present invention in any form. Presented below is a general outline of the fermentation production process and the process used to recover the produced lactoferrin. One of ordinary skill in this art understands that the protocol may be changed or modified in minor ways in order to enhance the production of the desired lactoferrin or lactoferrin polypeptide.

The following examples are given for the purposes of illustrating various embodiments of the present invention and are not meant to be limitations of the present invention in any form.

EXAMPLE 1

CONSTRUCTION OF EXPRESSION VECTOR pPLF-19 FOR THE EXPRESSION OF RECOMBINANT HUMAN LACTOFERRIN IN ASPERGILLUS AWAMORI

This example demonstrates the construction of an expression vector which is used to express recombinant human lactoferrin in *Aspergillus awamori*.

I. STRAINS, PLASMIDS, ENZYMES AND MEDIA

A. Bacterial and fungal strains

*Aspergillus awamori* strain ATCC 22342 was used as the host strain for the heterologous expression of human lactoferrin. *E. coli* strain DH5α was used in the construction of the human lactoferrin expression vector, pPLF-19.

B. Plasmids

The plasmids pUC19 and pGEM4 (Promega, Madison, Wis.) were used in various cloning steps leading to the final construction of the human lactoferrin expression plasmid pPLF-19.

The phleomycin resistance vector, pLO-3, which contains the phleomycin resistance gene (a phleomycin binding protein gene from *Streptoalloteichus hindustanus*) coupled to a yeast cytochrome C1 terminator was derived from the plasmid pUT713 (CAYLA, Toulouse-Cedex, FR). It is expressed in fungus by the β-tubulin promoter from *A. niger*.

C. Enzymes

Restriction enzymes were obtained from New England Biolabs (Beverly, Mass.). T4 Ligase, T4 Polymerase, T4 Kinase, and the Klenow fragment from *E. coli* DNA Polymerase I were purchased from Bethesda Research Laboratories (BRL, Gaithersburg, Md.). Mung Bean Nuclease was obtained from Stratagene (La Jolla, Calif.). Taq Polymerase was obtained from Promega Corporation (Madison, Wis.). DNA sequencing of plasmid constructs was accomplished using the Sequenase Version 2.0 T7 DNA Polymerase enzyme and kit (United Stated Biochemicals, Cleveland, Ohio). Novozym 234, a spheroplasting enzyme was urchased from Novo BioLabs (Bagsvaerd, Denmark).

D. General Growth Media

*E. coli* strains were grown in L-broth (Difco, Detroit, Mich.). Bacterial transformants were grown on L-broth plates containing 1.5% agar and 125 ug/ml ampicillin. Complete Media (CM) for growth of *A. awamori* in liquid is composed of: 50 ml of 20X Clutterbuck's salts (120 g $Na_2NO_3$, 10.4 g KCl, 10.4 g $MgSO_4$ $7H_2O$, 30.4 g $KH_2PO_4$), 2.0 ml Vogel's Trace Elements (0.3M citric acid, 0.2M $ZnSO_4$, 25 mM $Fe[NH4]_2[SO_4]_2$ $6H_2O$, 10 mM $CuSO_4$, 3 mM $SO_4^{-2}$, 8 mM boric acid, 2 mM $Na_2MoO_4.2H_2O$), 5.0 g tryptone, 5.0 g yeast extract, 10 g glucose in one liter of distilled water). 1.5 k agar was added for CM slants. PDA slants contained 39.0 g/L Potato Dextrose Agar in water (Difco, Detroit, Mich.), 10.0 g/L glucose, 10.0 g/L agar, 0.1 g/L $MgSO4.7H_2O$, 0.12 g/L $KH_2PO_4$, 0.25 g/L $(NH4)_2HPO_4$.

*A. awamori* lactoferrin-producing transformants were grown in kt-4 media: 150 g/L maltose, 60 g/L soyfine soymilk LF, 79.8 g/L $C_6H_5O_7Na_3.2H_2O$, 15 g/L, $[NH4]_2SO_4$, 1.0 g/L $NaH_2PO_4$; 2.05 g/L $MgSO_4.7H_2O$, 1.0 ml/L Tween 80, 2.0 ml/L antifoam 204; Dunn-Coleman et al., 1991, Bio/technology 9: 976–981.

E. ATCC Cell Deposit

The following transformed strain was deposited with the American Type Culture Collection pursuant to the provisions of the Budapest Treaty for the International Recognition of the Deposit of Microorganisms for the Purposes of Patent Procedure (American Type Culture Collection, 12301 Parklawn Drive, Rockville, Md. 20852) by the Applicants on Jul. 8, 1994: "Awa LF 24-1" is *Aspergillus awamori* transformed with the expression plasmid pPLF-19 containing the cDNA encoding human lactoferrin. This deposit was given ATCC Accession Number 74290. Applicants further agree to make this deposit available, without restriction to responsible third parties upon the granting of a patent from this application in the United States and comply with existing laws and regulations pertaining thereto, without limitation, except as to third parties adherence to applicants rights as prescribed by the claims of a patent issuing from this application.

II. METHODS

A. Construction of Human Lactoferrin Expression Plasmids

The following plasmids were constructed as progenitors to the final expression plasmid, pPLF-19. A diagram of the pPLF-19 construct is shown in FIG. 1. Abbreviations used in this figure are as follows: Apr: ampicillin resistance; hLF: human lactoferrin; GA: glucoamylase; pGA: promoter from glucoamylase; GA 3'UTR: glucoamylase 3' untranslated region; s.s.: signal sequence; phleo r: phleomycin resistance vector.

pPLF-1

The hLF cDNA was removed from pGEM4hLFc as a 2.3 kb SacI/HindIII fragment and subcloned into vector pUC-19. This subcloning was made in order to remove the cDNA from the pGEM4 backbone which contains an unwanted NgoMI site.

pPLF-2

The 5' end of hLF was modified to introduce a unique NgoMI site which can be used for a seamless addition of the glucoamylase (GA) promoter and signal sequence. Modification was made through PCR amplification of a 270 bp fragment spanning the 5' end of the mature lactoferrin coding sequence to a unique AccI site. The primers are listed below and are shown in SEQ. ID. No. 1 and 2, respectively.

```
              KpnI         NgoMI
5hLFFW  5' -G GGG TAC CGC  GCC GGC CGT AGG AGA AGG AGT G
                                   Gly Arg Arg Arg Arg Ser (Mature hLF N-term)

AccI
5hLFRV       5' - TTCGGTCCCGTAGACTTCCGCCGCT
```

The 270 bp fragment was amplified using Promega's Taq Polymerase with the following conditions: 1.25 to 5 mM MgCl2; 0.5 μM each primer (5hLFFW and 5hLFRV); 10 ng pGEM4hLFc as template. Cycled in Perkin Elmer 9600 Thermocycler: 1@2 min, 96° C.; 30@20 sec, 96° C./20 sec, 55° C./20 sec 72° C.; 1@5 min, 72° C.

Fragments were isolated from agarose, enzymatically blunted and phosphorylated and subcloned into pUC 19 cut with SmaI to give plasmid pPUC270. Sequence of the amplified product was confirmed using M13 universal forward and reverse primers. The fragment was then removed from pPUC270 as a KpnIAccI fragment and used to replace the Kpn/AccI fragment of pPLF-1. The resulting plasmid was designated pPLF-2.

pPLF-6

A 280 bp EcoRI/PstI fragment carrying the last 17 bp of hLF and 160 bp of GA 3' untranslated region (UTR) was subcloned from vector pAhLFG(+1) into EcoRI/PstI cut pUC19.

pPLF-7

The modified hLF gene of pPLF-2 was subcloned as an EcoRI fragment into vector pPLF-6. Correctly oriented plasmid (pPLF-7) contains full length mature hLF sequence with a unique NgoMI site immediately upstream and 160 bp of GA 3' UTR immediately downstream. GA promoter and signal sequences (see below) will be added to this vector.

The GA promoter and signal sequence was obtained by PCR amplification from genomic DNA isolated from A. awamori strain ATCC 22342. The forward primer spans a SacI site approximately 1.1 kb upstream of the GA signal sequence. Sequence of this primer was designed from published sequence for ATCC 10864 (GenBank Accession number X56442) and are shown in SEQ. ID. No. 3 and 4, respectively.

```
         GAFW:  5' -TATGCAGAGGAGCTCTCCCCTGAC
                                SacI
```

The reverse primer incorporates an NgoMI site for attachment to hLF.

```
               NgoMI
GARV: 5' -GAT TCC
GCC GGC CAA CCC TGT GCA GAC GAG GC
          ←   Ala Leu Gly Thr Cys Val Leu  ←
              ↑         (Processing point)
```

Correct sized fragments (1.1 kb) were amplified from ATCC 22342 genomic DNA using the following conditions: 2.5 mM MgCl$_2$,: 0.5 μM each primers (GAFW and GARV) and 100 ng genomic DNA. Cycling parameters were set at 1@2 min, 95° C.; 30@30 sec, 95° C./30 sec 60° C./45 sec, 72° C.; and 1@5 min 72° C.

Amplified products were blunted, phosphorylated and subcloned into pUC-19 cut with SmaI. DNA sequence was generated from the 3' end of the amplified fragment to check for fidelity of amplification spanning the GA signal sequence region. Clones with verified sequence were used as the stock source of GA promoter and s.s. fragments.

pPLF-9

The PCR amplified GA promoter and signal sequences was ligated to vector pPLF-7 as a SacI/NgoMI fragment to give vector pPLF-9. Sequence generated through the junctions in one direction verified a clean ligation.

pPLF-18

The final GA expression plasmid contains the GA promoter, signal sequence, and sequence encoding 498 aa of pro-glucoamylase fused to hLF. The pro-hexapeptide of glucoamylase which ends in the dibasic KEX-2 recognition sequence Lys-Arg is engineered between the GA and hLF sequences. Presumably, the chimeric protein will be better recognized by the endogenous GA secretory pathway resulting in higher secretion titers of hLF. The KEX-2 linker should allow for accurate processing of hLF away from GA.

pPLF9 was cut first with NgoMI. The ends were filled with dCTP using Klenow fragment. Mung bean nuclease was then used to remove the remaining 5' overhangs to give a blunt end ready for an in-frame protein fusion. The vector was then cut with NsiI in order to accept the GA sequence which was PCR amplified as described below.

A fragment encoding the desired GA fragment was PCR amplified from strain ATCC 22342 with the following set of primers as shown in SEQ. ID. No. 5, 6, and 7, respectively.

GA-1:5'-GAATTCAAGCTAGATGCT

This forward primer spans bases 1–18 of published ATCC 22342 (NRRL 3112) GA upstream sequence (Nunberg et al. Mol Cell Bio 1984, p 2306–2315). This sequence lies approximately 50 bp upstream of a unique NstI site which was used in the construction.

```
             Ser Val Thr Ser Thr Ser Lys Asn Val Ile Ser

5' - AGC GTG ACC TCG ACC AGC AAG AAT GTG ATT TCC
            AAG CGC
            Lys Arg

KX2GA: 3' - TCG CAC TGG AGC TGG TCG TTC TTA CAC TAA AGG
            TTC GCG-5'
```

This reverse primer sequence is complementary to the inserted pro-hexapeptide (underlined) encoding sequence and followed by the complement of pro-GA sequence encoding as 492–498.

The 2.0 kb fragment was PCR amplified using Taq polymerase. 2.5 mM $MgCl_2$ was empirically determined to give the best amplification. The fragment was enzymatically blunted with Klenow in order to clean up potentially ragged ends leftover from the amplification. The blunted fragment was then cut with NsiI and then subcloned into manipulated vector pPLF-9 (see above) as an NsiI/blunt fragment to give plasmid pPLF-18. Sequence was verified through the GA/KEX-2/hLF junction through di-deoxy sequencing.

pPLF-19

A phleomycin resistance marker derived from CAYLA vector pUT713 (*Streptoalloteichus hindustanus ble* gene) and expressed from the *A. niger* tubulin promoter (pPLO-3) was added to pPLF-18 as a 2.3 kb HindIII fragment to give the final expression plasmid pPLF-19.

B. DNA Transformation of *Aspergillus awamori* Strain ATCC 22342.

*Aspergillus awamori* strain ATCC 22342 was spheroplasted and transformed by a procedural modification of Tilburn et al, 1983, Gene 26: 205–221. Conidating cultures of *A. awamori* ATCC 22342 grown on Complete Media (CM) slants for four to seven days at 30° C. were scraped with 2 mls of NP40 water (0.005% Nonidet-40) to obtain a spore suspension. One ml of the spore suspension (approximately $1 \times 10^8$ spores) was added to 50 mls of CM and grown for 22 hours at 30° C., 200 rpm. Mycelia was collected by filtration through a double layer of cheesecloth and added to 50 mls of KCM buffer (Cantoral, et al., 1987, Biotechnology 5: 494–497; KCM: 0.7M KCl, 10 mM MOPS, pH 5.8) with 5 mg/ml of Novozym 234 (Novo Biolabs, Bagsvaerd, Denmark) and incubated at 30° C., 90 rpm overnight for spheroplast generation.

The spheroplasts were harvested by filtration through a funnel packed with miracloth (Calbiochem; La Jolla, Ga.) and covered with cheesecloth into four 15 ml conical centrifuge tubes, then spun at 1800 rpm for ten minutes in a bench-top centrifuge. The pellets were gently resuspended in a total of 15 mls of KCM buffer and re-centrifuged. The pellet was again washed in 15 mls of KCM buffer, then resuspended in KCMC (KCM+50 mM $CaCl_2$) buffer to a final density of $5 \times 10^7$ cells/ml.

Five µgs of pPLfF19 plasmid DNA in 20 ul TE buffer (10 mM Tris-HCl, 1 mM EDTA, pH 8.0) was added to 200 ul of spheroplasts, and 50 µl of PCM (Cantoral et al; PCM: 40% PEG 8000, 10 mM MOPS, pH 5.8, 50 mM $CaCl_2$ [$CaCl_2$ added prior to use]) was gently pipetted into the DNA-spheroplast mixture and incubated on ice for thirty minutes.

One ml of freshly prepared PCM was added to the transformation mix, the mix was pipetted into 50 mls of Regeneration Agar (CM+1.3M Mannitol, 3% agar) cooled to 50° C. that was then divided into five petri plates. Spheroplasts were allowed to regenerate 3 to 5 hours at 30° C. before overlaying with an equal amount of OL+120 ug/ml phleomycin(OL: 1% peptone, 1% agar; phleomycin [CAYLA; Toulouse, FR]). Putative transformants were transferred to PDA slants containing 125–150 ug/ml phleomycin.

C. Fermentation Conditions for Human Lactoferrin Expression in *Asperqillus awamori*

Spores from putative HLF-producing transformants were transferred from selective PDA slants to CM slants and grown for four days at 30° C. Conidia was harvested by scraping the slant with 1.5 ml of NP40 Water, and aliquot of $1 \times 10^8$ spores was added to 30 ml of KT-4 media in a 250 ml flask. Cultures were fermented for six days at 30° C. 200 rpm. Lactoferrin samples were collected by centrifuging one ml of fermentation broth at 3000 rpm for 15 minutes and assaying the retained supernatant.

D. Human Lactoferrin Assay

Lactoferrin was quantified by a modification of a Non-Competitive Avidin-Biotin Immunoassay developed by Vilja et al, 1985, J. of Imm. Methods 76: 73–83. A ninety-six well microtiter plate (U-Bottom Microtest III; Baxter, Chicago, Ill.) was coated with 100 ul of 0.1 ug/ml rabbit antihuman lactoferrin antibody (Sigma, St. Louis, Mo.) in Coating Buffer (0.1M Sodium Carbonate/Bicarbonate, pH 9.6), and was shaken overnight at 4° C.

The next day, the coating solution was removed, and the plates were washed three times with Washing Buffer (1× PBS pH 7.4, 0.5% Tween 20) prior to blocking with 250 ul of Diluent Buffer (1× PBS pH 7.4, 1% BSA [Fraction V, RIA grade, United States Biochemicals, Cleveland, Ohio], 0.05% Tween 20) for at least one hour at room temperature. The Diluent Buffer was discarded and 100 ul of diluted fermentation samples and known lactoferrin standards were added to the plate, which was then incubated for one hour at 37° C. The collected supernatant from the fermentation samples was diluted 1:1000 with Diluent Buffer prior to its addition to the microtiter plate. Lactoferrin standards consisted of human lactoferrin (Sigma, St. Louis, Mo.) diluted 1 to 1000 ng/ml in Diluent Buffer.

After reaction at 37° C. the samples were discarded and the plate was washed three times with Wash Buffer. One hundred ul of biotinylated anti-HLF antibody (Biotin-SP-Rabbit anti-hLF IgG, Jackson Immuno-Research Labs) diluted 1:7500 in Diluent Buffer from a 1 mg/ml stock was added to each well and incubated for one hour at 37° C.

The solution was discarded and the plate was washed three times with Wash Buffer before adding 100 ul of ABC reagent (Vectastain ABC Kit, Vector Labs, Burlingame, Ga.) and incubating the plate at 37° C. for one hour. Vectastain Reagent A was diluted 1:200 and Reagent B was diluted 1:400 in Diluent Buffer prior to combining both solutions and allowing them to preincubate one hour at room temperature before use.

The ABC solution was discarded and the plate was washed five times with Wash Buffer. One hundred ul of OPD Substrate Solution (10 ml Substrate Buffer (25 mM citric acid, 50 mM $Na_2HPO_4 7H_2O$, pH 5.0), 8 mg o-Phenylenediamine [Bethesda Research Labs, Gaithersburg, Md.], 100 ul 30% $H_2O_2$ [Sigma, St. Louis, Mo.]) was added and the plate was incubated in the dark for twenty minutes with gentle agitation at room temperature. After color development, 100 ul of 2M $H_2SO_4$ was added to stop the reaction. The plate was then read at 490 nm, and lactoferrin concentrations were determined by comparison to the known standards.

EXAMPLE 2

EXPRESSION AND PROCESSING OF hLF (pPLF-19) IN ASPERGILLUS AWAMORI

When the human lactoferrin expression cassette pPLF-19 is transformed into A. awamori 22342, secreted lactoferrin is detected in the media by both the ELISA assay and by Western blot analysis. One transformant, #19-254, produces approximately 250 mg/l of human lactoferrin (hLF). A more preferred transformant, Awa LF 24-1 (ATCC Accession No. 74290; #19-24.1) produces approximately 500 mg/l of human lactoferrin. Experiments improving yield and strain development are ongoing in order to increase the production of recombinant hLF in A.awamori. To date, the inventors have obtained titers >900 mg/l hLF produced in A.awamori transformants containing strain Awa LF 24-1. The results are shown in the comparative Production Table below.

Since the pPLF-19 expression product is a chimeric protein made up of 498 amino acids of glucoamylase and the complete coding region of hLF separated by a KEX-2 cleavage site, SDS-PAGE, and silver staining, Western blot analysis and N-terminal sequencing were conducted to determine whether the protein was correctly processed.

A. Silver stained SDS-Polyacrylamide Gel Analysis of Recombinant Human Lactoferrin Purified from Asperqillus awamori Transformants.

Figure 2:
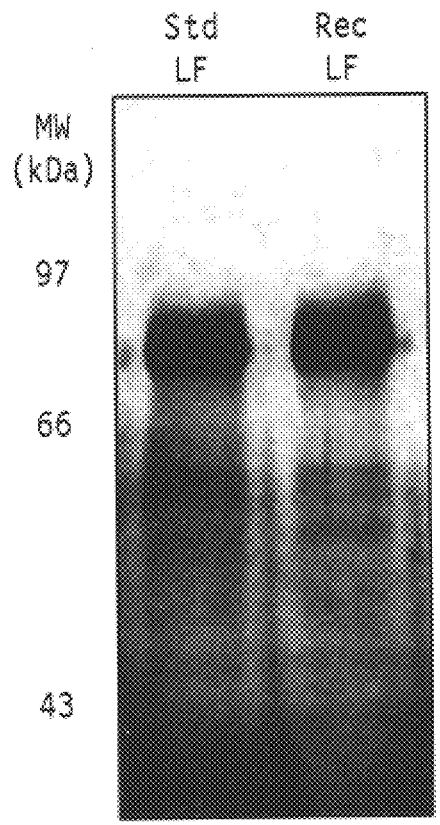
FIG. 2 is an SDS-PAGE of recombinant hLF (500 ng) purified from the growth medium of *Aspergillus awamori* transformants containing pPLF-19.

Recombinant human lactoferrin was purified from the growth medium of Aspergillus awamori transformants by ion-exchange chromatography using CM-Sephadex C50 (Stowell, K. M. et al., Biochem J., 276:349–355). Standard human breast milk LF (Std hLF) and purified recombinant hLF (Rec hLF) were resolved on a 7.5% SDS-Polyacrylamide gel and silver-stained. The results of this analysis are shown in FIG. 2. The recombinant hLF protein migrates at the expected size for processed hLF (lane 2) and is identical as in size to the standard hLF (lane 1). The position of the molecular weight markers are indicated on the left.

B. Western Blot Analysis of Glycosylated and Deglycosylated Recombinant Human Lactoferrin Purified from Asperqillus awamori Transformants.

Figure 3:
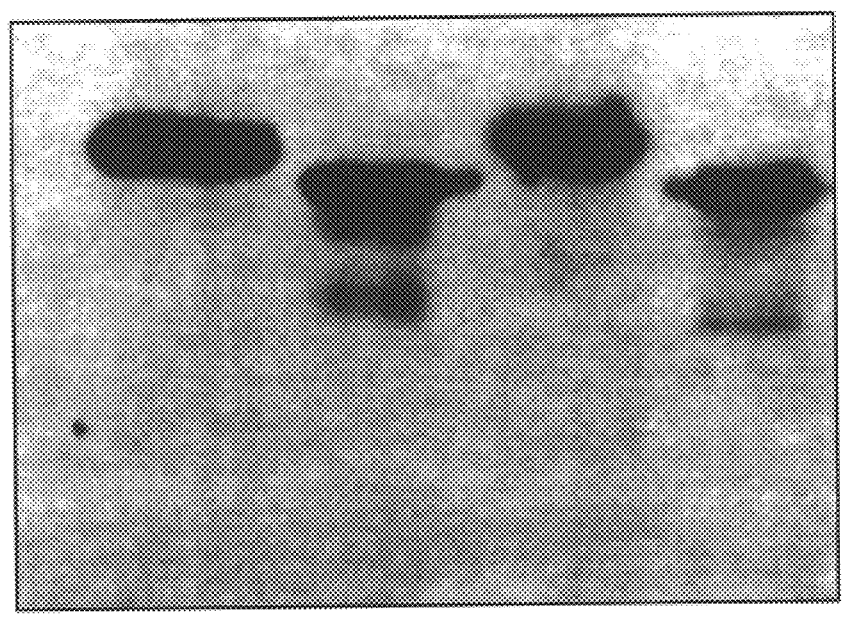
FIG. 3 is a Western blot of glycosylated (1 $\mu$g) and deglycosylated recombinant hLF (1 $\mu$g) purified from the growth medium of *Aspergillus awamori* transformants containing pPLF-19.

Recombinant human lactoferrin purified from the growth medium of Aspergillus awamori transformants, untreated and treated with N-glycosidase F, were resolved by SDS-polyacrylamide electrophoresis, transferred to nitrocellulose and probed using a specific IgG directed against human lactoferrin (Sigma). The results of this analysis are shown in FIG. 3. Comparison of untreated recombinant hLF with untreated standard breast milk hLF illustrate that both of these proteins co-migrate (FIG. 3 lanes 3 and 1, respectively). N-glycosidase F is an enzyme which hydrolyses the glycosylamine linkage generating a carbohydrate free peptide of smaller molecular weight. Comparison of recombinant hLF with standard hLF after treatment with N-glycosidase F illustrates that both proteins migrate identically suggesting that both proteins are similarly N-linked to carbohydrate (FIG. 3, lanes 4 and 2, respectively).

EXAMPLE 3

N-TERMINAL SEQUENCE ANALYSIS CONFIRMS THAT RECOMBINANT HUMAN LACTOFERRIN IS CORRECTLY PROCESSED IN ASPERGILLUS AWAMORI

In order to confirm that the recombinant hLF produced in A. awamori is correctly processed, the N-terminal portion of the recombinantly produced hLF was sequenced. First, recombinant hLF was expressed in A. awamori as a fusion protein to the catalytic domain of the A. niger glucoamylase gene (498 AA) which is separated by a synthetic linker which codes for KEX-2 proteolytic cleavage site. Next, the recombinant hLF was purified from the growth medium using CM-sephadex C50 (previously described by Stowell et al., Biochem J. 276; 349–59 (1991)). To determine if recombinant hLF was correctly processed at its N-terminus, the first 10 N-terminal amino acids of the purified protein were sequenced using the automated Edman degradation procedure (5 ug). The results of this analysis are outlined in FIG. 4. The sequence of the recombinant protein is identical to the corresponding amino acids in human breast milk lactoferrin. Hence, recombinant hLF has been correctly processed at the KEX-2 proteolytic cleavage site in A.awamori.

EXAMPLE 4

FUNCTIONAL ANALYSIS OF HUMAN LACTOFERRIN PRODUCED IN ASPERGILLUS AWAMORI

A. Iron Binding and Saturation of Standard and Recombinant hLF

Figure 5:
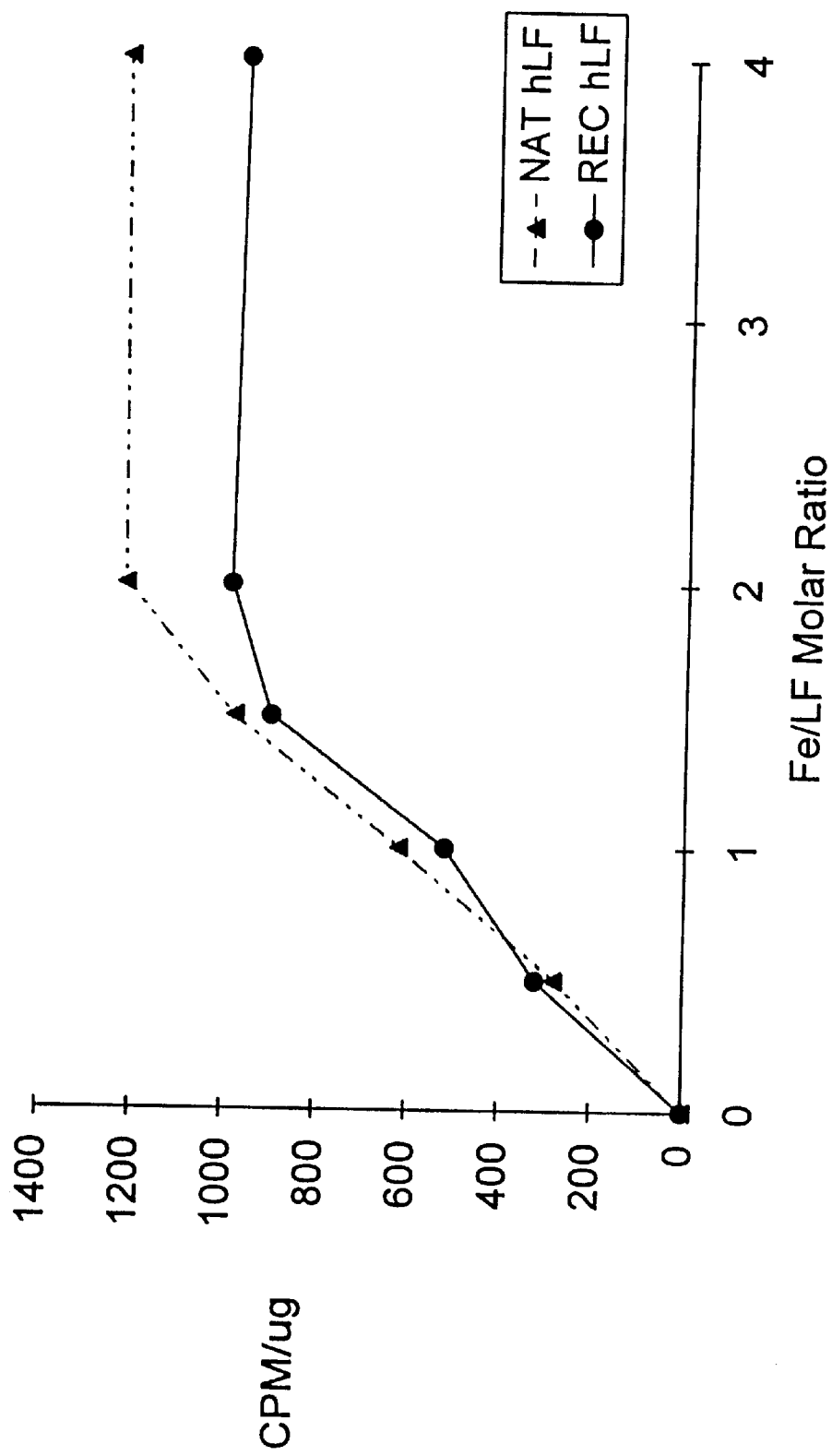
FIG. 5 presents the results of an iron binding and saturation of standard and recombinant hLF study.

Lactoferrin is an iron-building glycoprotein having the capacity to bind two moles of iron per mole of LF. To determine if the binding of iron by recombinant lactoferrin was saturable, an iron-binding assay was performed. To generate apo-lactoferrin, purified Rec hLF and human breast milk were dialyzed against 0.1M citric acid, pH 2.0 followed by extensive dialysis against $H_2O$. The pH of the solution was slowly raised to pH 7.6 using 5 mM sodium phosphate. Increasing concentrations (0.5 to 4.0 molar excess) of $FeCl_3$:$^{59}FeCl_3$:NTA(400:1:8) were added to hLF (500 ug) in 1 ml binding buffer (0.025M Tris, pH 7.8; 0.01M Sodium bicarbonate; 0.1M NaCl). Samples were incubated at room temperature for 30 minutes. Iron-bound hLF was separated from unbound iron and NTA by passage over a NAP-10 column which had been equilibrated with 15 ml of binding buffer. The amount of iron bound to LF was quantified using liquid scintillation counting. The results of this analysis are outlined in FIG. 5. Recombinant and standard hLF bind iron in a similar manner. This binding of iron is dose dependent. Furthermore, binding of iron by both standard and recombinant hLF is saturable at a 2:1 molar ratio of iron to lactoferrin. Typically, saturation levels are reached at 92.5% of maximal binding. This is indicative of initial 7.5% iron still bound to the lactoferrin after dialysis. For the purpose of this invention, "standard hLF" or "natural hLF" is human lactoferrin isolated from human breast milk and purchased from Sigma.

B. pH Stability of Iron-Binding to Standard and Recombinant hLF

Figure 6:
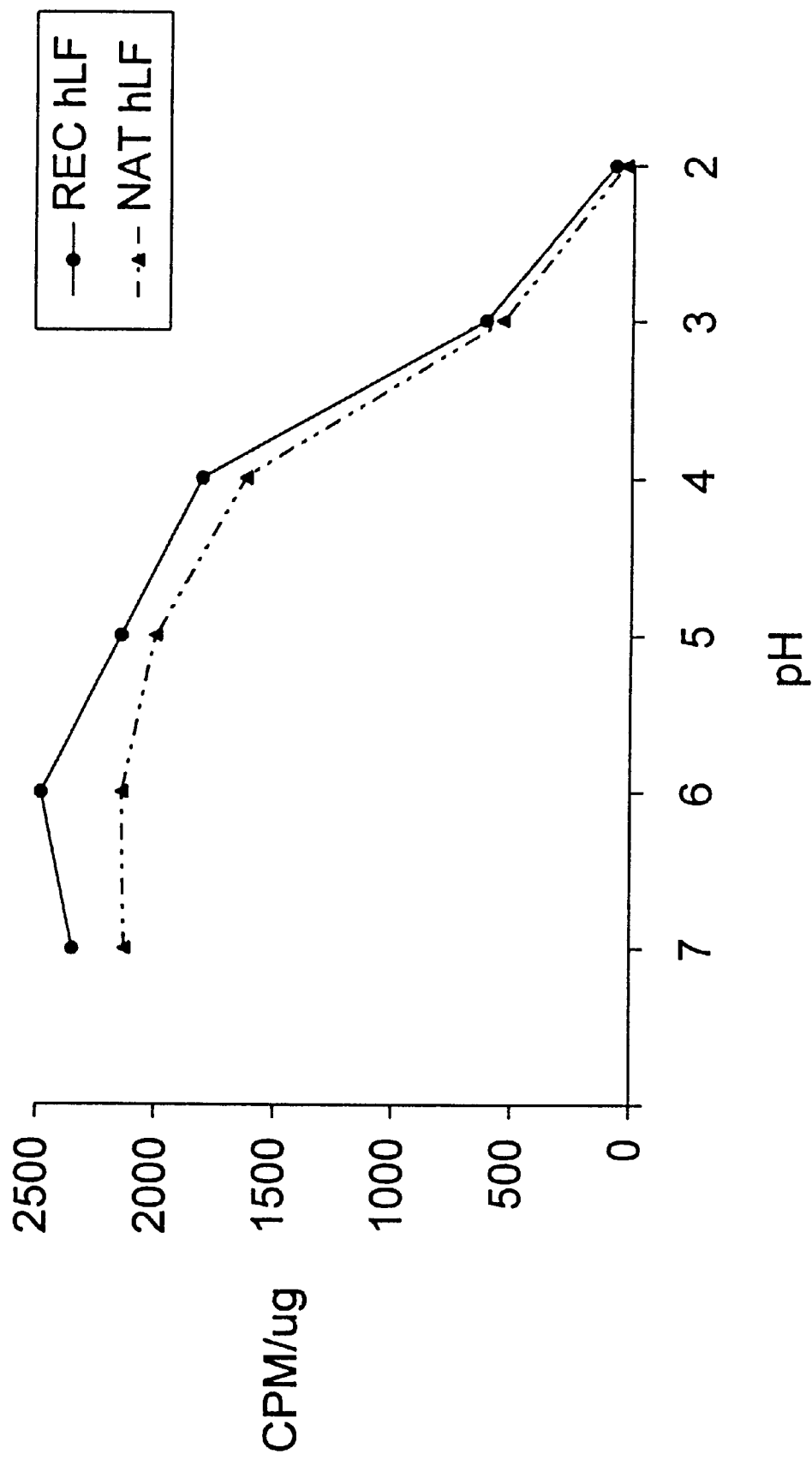
FIG. 6 presents the results from comparing the pH stability of iron-binding to standard and recombinant hLF.

To determine the pH stability of iron-binding to standard and recombinant hLF, $^{59}$Fe-saturated standard and recombinant hLF (500 ug) were dialyzed against buffers ranging from pH 7.0 to pH 2.0 for 48 hours at 4° C. to remove unbound iron (Stowell et al; Biochem J, 276; 349–59 (1991). Iron bound to the hLF samples after dialysis was quantified using liquid scintillation counting. The results of this analysis are shown in FIG. 6. The pH-dependent release of iron from both standard and recombinant hLF is identical. Both standard and recombinant hLF retain most of the iron over a pH range of 7–4 and are essentially iron-free at pH 2.0.

C. Antimicrobial Action of Natural and Recombinant hLF against E.coli 0111

Figure 7:
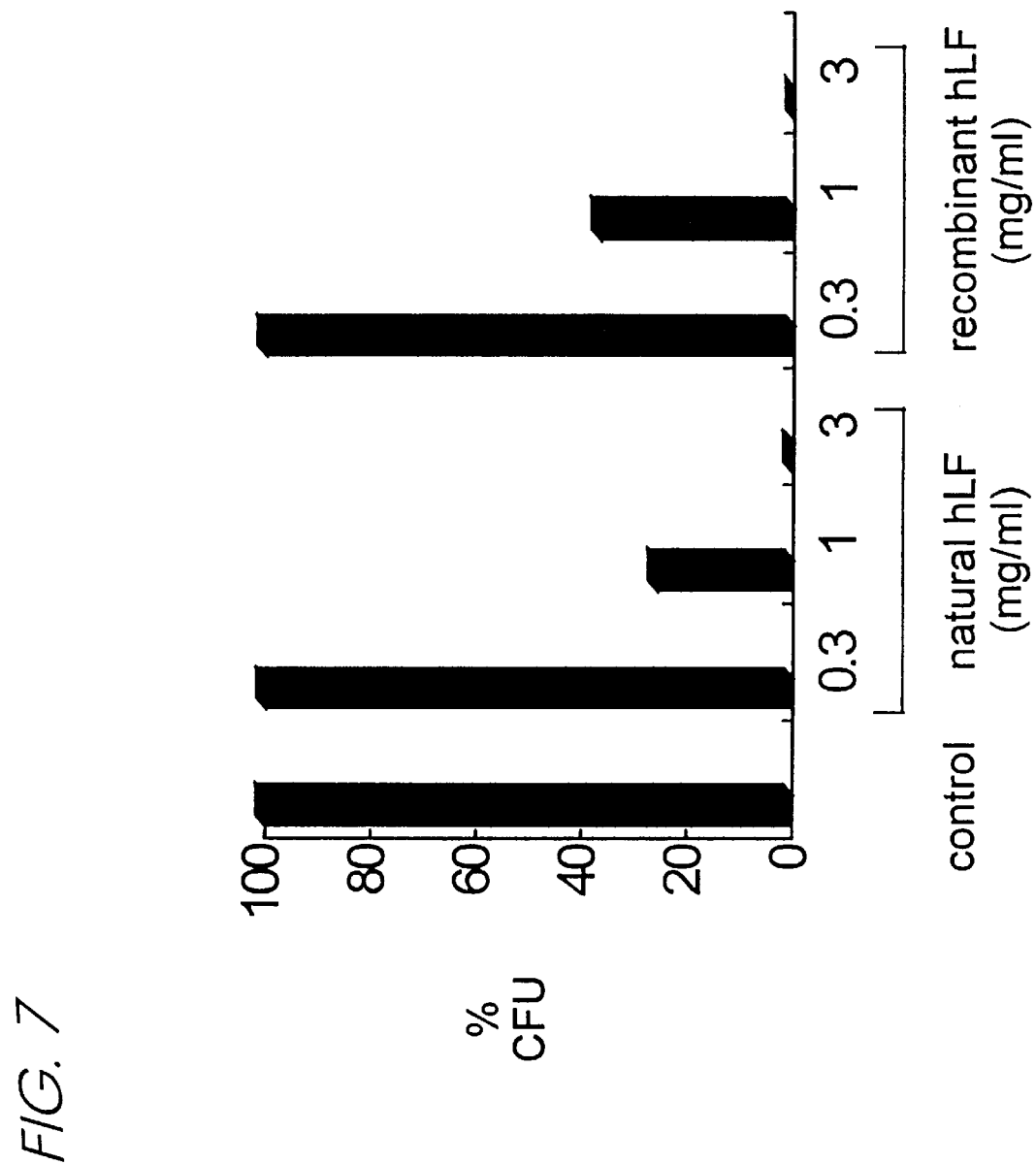
FIG. 7 presents the antimicrobial action of natural and recombinant hLF against *E.coli* 0111.

The antimicrobial activity of both natural (standard) and recombinant hLF against *E.coli* 0111 was determined using an in vitro microtitre plate assay (Nonnecker and Smith., J. Dairy Sci, 67; 606–613 (1984). Briefly, a standard inoculum of logarithmic-phase cells ($1 \times 10^6$ CFU/ml) were incubated in the presence or absence of increasing concentrations of Apo-Std or Apo-Rec hLF in 1% Basal Bactopeptone medium (100 ul). The samples were cultured at 37° C./200 RPM for 4 hours. Aliquots were removed, serially diluted and plated overnight on MacConkey agar plates for enumeration. The results of this analysis are shown in FIG. 7. Natural and recombinant hLF exert similar dose dependent antimicrobial action against *E.coli* 0111 at all concentrations tested.

D. Antimicrobial Action of Natural and Recombinant hLF Against *Shigella flexneri*.

Figure 8:
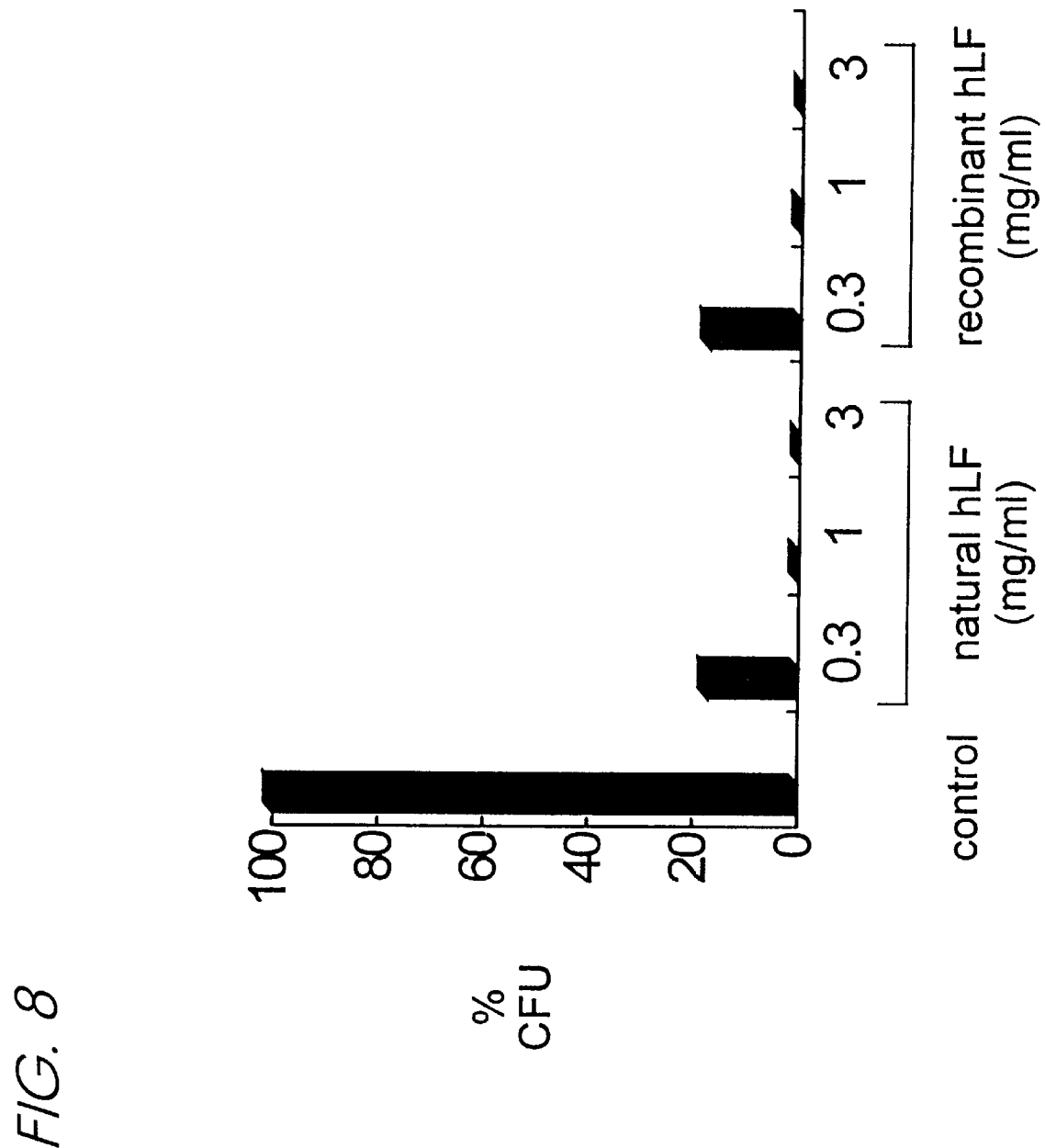
FIG. 8 presents the results obtained from studies on antimicrobial action of natural and recombinant hLF against *Shigella flexneri*.

The antimicrobial action of both natural (standard) and recombinant hLF against *S.flexneri* was determined as described in Example 4(C). The results of this analysis are shown in FIG. 8. Both natural and recombinant hLF exert similar dose dependent inhibition of *S.flexneri* at all concentrations tested.

E. Antimicrobial Action of Natural and Recombinant hLF Against *Shigella flexneri* (Time Kill Study).

Figure 9:
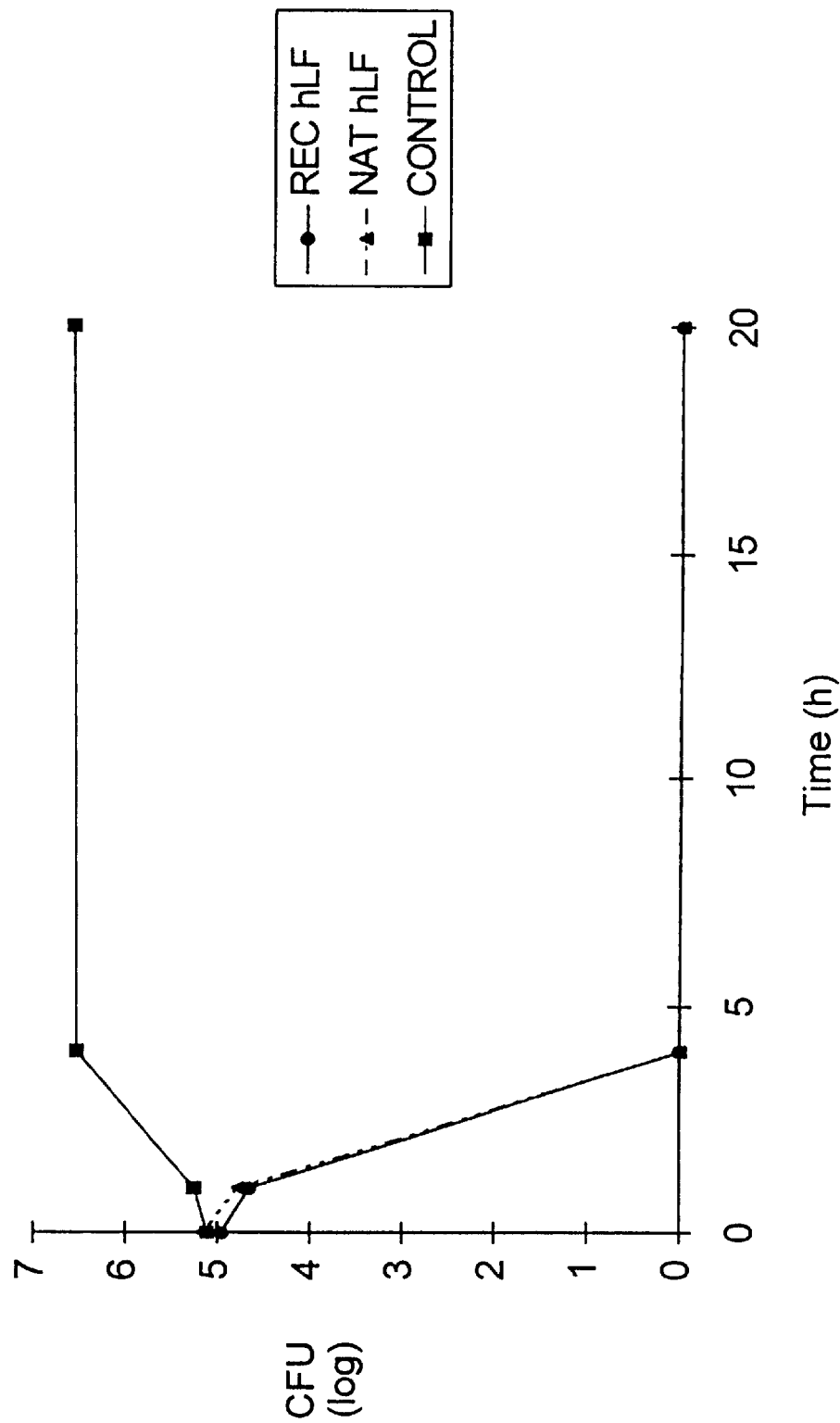
FIG. 9 presents the results of antimicrobial action of natural and recombinant hLF against *Shigella flexneri* in a time kill study.

A time course of the antimicrobial activity of natural and recombinant hLF was carried out. Briefly, a standard inoculum of logarithmic-phase *S. flexneri* cells ($1 \times 10^6$ CFU/ml) were incubated in the presence or absence of Apo-Std or Apo-Rec hLF (300 ug) in 1% Basal Bactopeptone medium (100 ul). The samples were cultured at 37° C./200 RPM. Aliquots were removed at various time intervals (0, 1, 4 and 20 hours), serially diluted and plated overnight on MacConkey agar plates for enumeration. The results of this analysis are shown in FIG. 9. Recombinant natural and recombinant hLF exert similar antimicrobial action against *S.flexneri* in a time dependent manner with no detectable *S. flexneri* CFUs remaining after 4 hours.

EXAMPLE 5

CONSTRUCTION OF A UNIVERSAL SHUTTLE VECTOR pPLF-26 TO ALLOW IN FRAME SUBCLONING OF ANY cDNA

This Example describes the design and construction of human lactoferrin shuttle vectors capable of expressing mutant forms of hLF in Aspergillus species. Unique NotI and EcoRI sites were created in order to facilitate the cloning of altered forms of lactoferrin into the vector. Protein is expressed under the direction of the glucoamylase promoter and signal sequence as a glucoamylase: hLF chimera, which is process in vivo through the recognition of a KEX-2 cleavage site. Both vectors also contain the glucoamylase 3' untranslated region for enhanced mRNA stability and phleomycin resistance gene for selection in Aspergillus.

I. HUMAN LACTOFERRIN EXPRESSION VECTOR CONSTRUCTIONS

A. Construction of pPLF-26

In order to create an expression vector capable of accepting mutuant forms of lactoferrin, several restriction sites were altered to allow for unique cloning sites. To substitute mutant forms of lactoferrin into the plasmid, the addition of a NOTI site at the 5' end of the hLF gene was designed. An EcoRI site was selected as a unique cloning site at the 3' end of the hLF gene; and, other existing EcoRI sites needed to be eliminated in order to make this site unique.

Figure 10A:
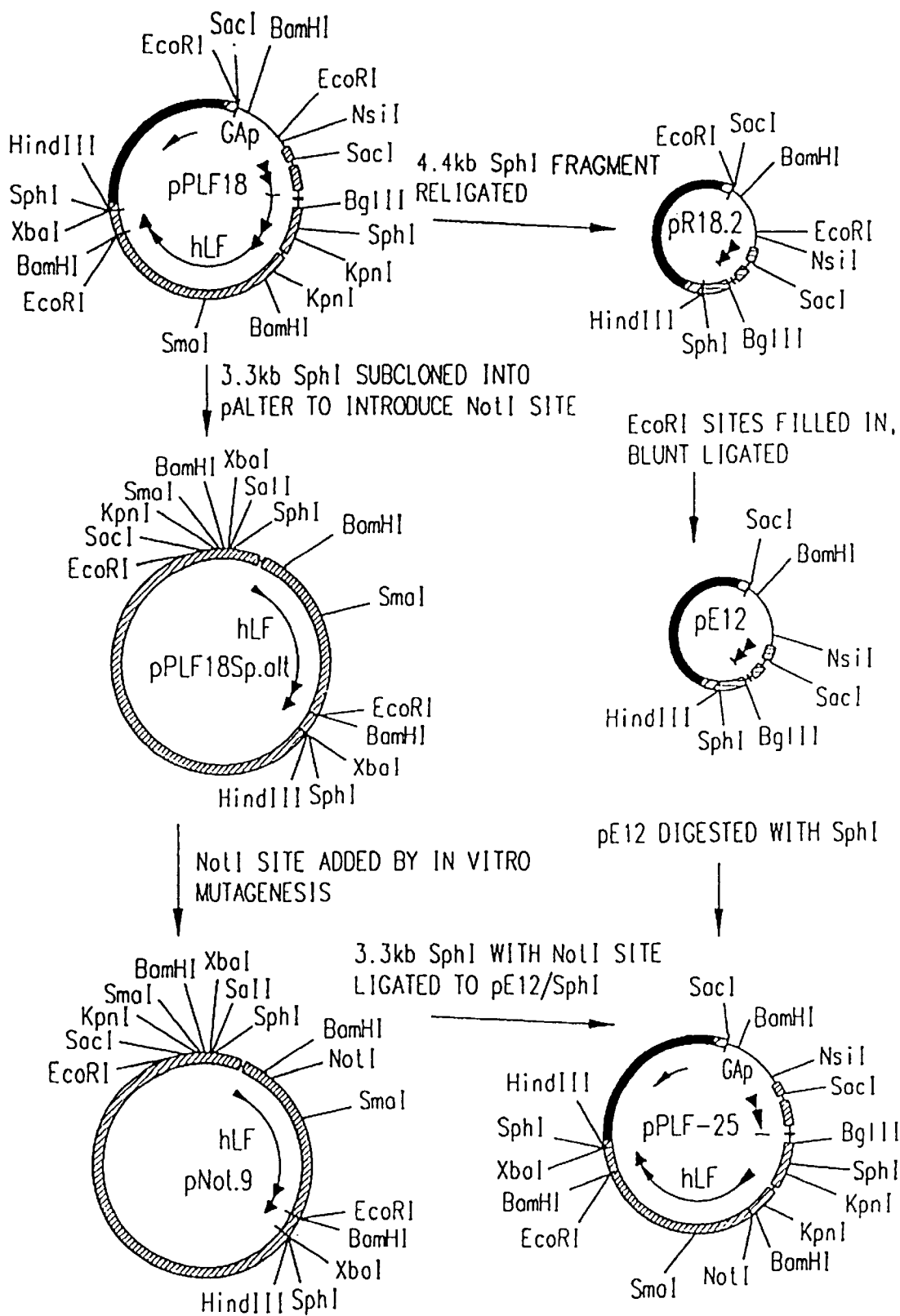
FIGS. 10-A through 10-C outline the design, intermediates, and construction of universal *Aspergillus awamori* expression shuttle vector pPLF-26. Note that not all restriction sites are shown in these figures.

In addition to the unique cloning sites, pPLF-26 contains the *Aspergillus awamori* glucoamylase (GA) promoter, signal sequence, and 498 amino acids of the glucoamylase protein which is separated from hLF by a KEX-2 recognition site. The vector also contains the *Aspergillus niger* GA 3' untranslated region (UTR), and the phleomycin resistance gene from *Streptoallotetchus hindustanus* (CAYLA vector pUT713) expressed by the *A. niger* beta-tubulin promoter. For selection and replication in *E. coli*, the plasmid contains the ColEI origin of replication and the ampicillin resistance gene. The construction of hLF expression vector pPLF-26 is outlined in FIG. 10-A and FIG. 10-B, and a description of construction intermediates is listed below.

pPLF18SP.Alt

Plasmid pPLF-18, which contains the promoter, signal sequence and partial protein sequence of glucoamylase separated from hLF by a KEX-2 recognition site, was selected as the starting plasmid for the desired site modifications. pPLF-18 was digested with SphI to isolate two fragments; the 3.3 kb fragment containing hLF was subcloned into the in vitro mutagenesis vector pALTER in the correct orientation to give pPLF18Sp.Alt.

pR18.2

The 4.4 kb Sph fragment from pPLF-18 was relegated to give pR18.2.

pNot.9

NotI restriction site spanning the KEX-2 cleavage site and hLF start site was created by in vitro mutagenesis of the vector pPLF18Sp.Alt. The NotI site, which is the result of a changing a "T" nucleotide to a "C" nucleotide, is inframe, and does not change any amino acids. The following 21-mer oligonucleotide (as shown in SEQ. ID. No. 8) was used for the mutagenesis, where the small case letter denotes a base change:

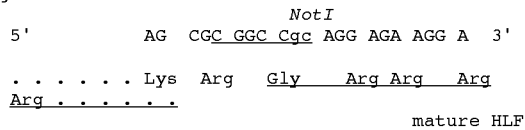

```
Oligo HLF NotI:
                          NotI
    5'       AG  CGC GGC Cgc AGG AGA AGG A  3'

. . . . . . Lys  Arg    Gly    Arg Arg   Arg
    Arg . . . . . . .
                                        mature HLF
```

The mutagenic oligo HLF NotI was used in conjunction with the ampicillin repair oligo (Promega) to anneal to 0single-stranded pPLF18Sp.Alt DNA, which was then filled in using T4 DNA Polymerase and T4 DNA ligase. After transformation of the repair minus strain BMH 71-18 mutS and JM109, 50% of the selected transformants contained in the new NotI site, one of which was designated pNot.9.

pΔE12

Plasmid pR18.2 was digested with EcoRI and the two fragments were isolated by gel electrophoresis. Both fragments were filled in separately with Klenow, and the larger 3.6 kb fragment was dephosphorylated with calf intestinal phosphatase (CIP) at 50° C. for one hour. After phenol extractions and ethanol precipitation, both filled in fragments were blunt ligated to each other. Prior to transformation, the ligation mix was digested with EcoRI to linearize any vector still containing an EcoRI site. Three clones of sixteen had both EcoRI to linearize any vector still containing an EcoRI site. Three clones of sixteen had both EcoRI sites filled in, and were in the correct orientation. One of these was designated pΔE12.

pLF-25 pΔE12 was digested with SphI and dephosphorylated with CIP. A 3.3 kb SphI fragment containing the new NotI site was isolated from pNot.9 and ligated to pΔE12/Sph. A clone with the correctly oriented SphI fragment was designated pPLF-25, which contained both unique EcoRI and NotI sites, and hLF fused to glucoamylase sequence expressed by the GA promoter.

pLO3ΔRI

In order to make pPLF-25 useful for selection in Aspergillus, a phleomycin resistance cassette was added. The cassette in the plasmid pLO3 contained two EcoRI sites which needed to be eliminated before the cassette could be added. Plasmid pLO3 was digested with EcoRI, both 4.3 and 0.9 kb fragments were isolated, and separately filled in with Klenow. After the fill-in reaction, the 4.3 kb fragment was treated with CIP, then purified and precipitated. Both filled-in fragments were ligated to each other overnight. Selected colonies after bacterial transformation revealed that five of twenty-four had both EcoRI sites filled in and were in the correct orientation, giving pLO3ΔRI.

pPLF-26

A 2.3 kb HindIII fragment from pLO3ΔRI, containing the phleomycin resistance gene transcribed by the B-tubulin promoter, was ligated to pPLF-25 digested with HindIII and dephosphorylated with CIP. Nine out of sixteen clones had the HindIII fragment in both orientations. The plasmid designated "pPLF-26" has the phleomycin resistance gene being transcribed in the same direction as the hLF gene.

Figure 11:
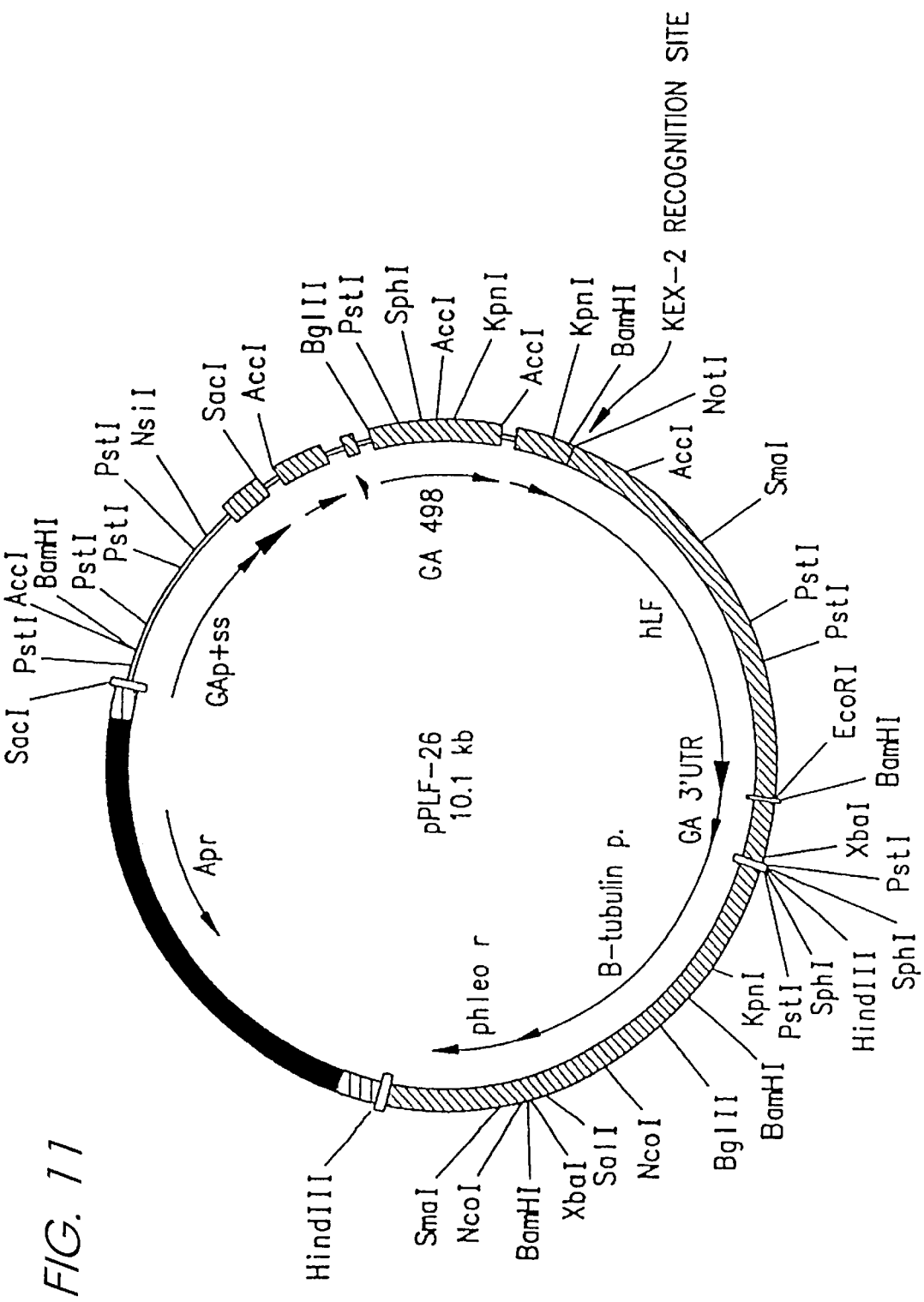
FIG. 11 presents a detailed description of a universal shuttle vector pPLF-26 which contains unique Not1 and EcoRI sites for cloning.

FIG. 11 presents a detailed description of a universal shuttle vector pPLF-26 which contains unique NotI and EcoRI sites for cloning. A pre-existing EcoRI site in the glucoamylase (GA) promoter region was removed by fill-in. The vector also contains the GA untranslated region, a Kex-2 cleavage site, and phleomycin resistance for selection in A. awamori. Note that all known restriction sites are shown in this figure.

Figure 12:
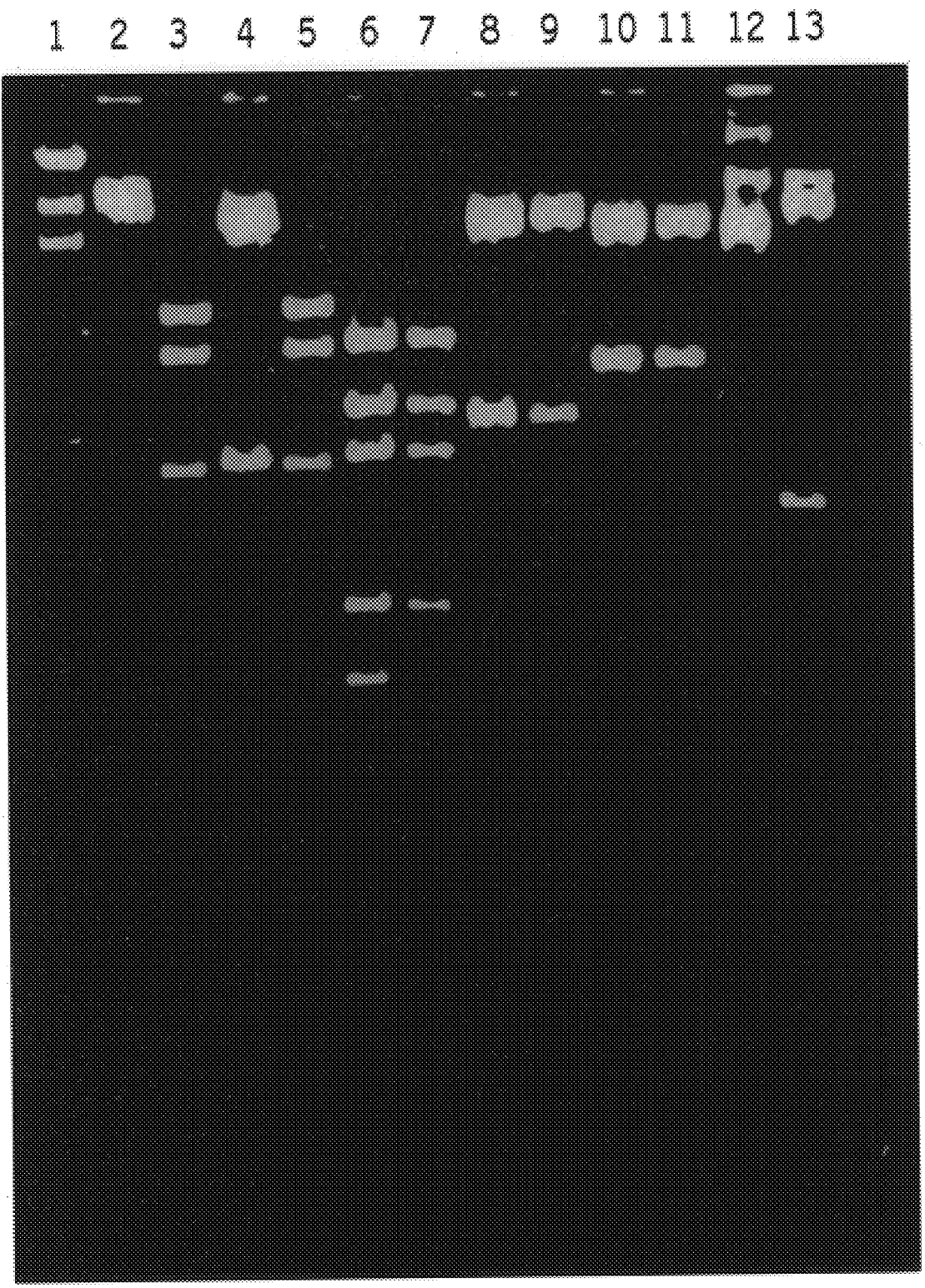
FIG. 12 presents the results from digesting pPLF-26 and pPLF-19 with various restriction enzymes to confirm the presence of the unique NotI and EcoRI sites, and the orientation of the plasmid.

FIG. 12 presents the results from digesting pPLF-26 and pPLF-19 with various restriction enzymes to confirm the presence of the unique NotI and EcoRI sites, and the orientation of the plasmid. One μg of either pPLF-26 or pPLF-19 DNA was digested in a 20 ul volume for one hour at 37° C., with the indicated restriction enzymes. Lane 1. One μg Lambda HindIII standard. Lane 2. pPLF-26 digested with EcoRI. Lane 3. pPLF-19/EcoRI. Lane 4. pPLF-26/EcoRI and NotI. Lane 5. pPLF-19/EcoRI and NotI. Lane 6. pPLF-26/BamHI. Lane 7. pPLF-19/BamHI. Lane 8. pPLF-26/HindIII. Lane 9. pPLF-19/HindIII. Lane 10. pPLF-26/SphI. Lane 11. pPLF-19/SphI. Lane 12. pPLF-26/Xba (note: incomplete digest) Lane 13. pPLF-19/Xba.

This universal vector can readily be adapted to express a variety of different desired proteins. For example, the sequences of published hLF's can be inserted into this vector and expressed and isolated therefrom.

EXAMPLE 6

EXPRESSION OF BOVINE AND PORCINE LACTOFERRIN IN *ASPERGILLUS AWAMORI*

The universal A. awamori expression vector constructed in Example 5 can be used to allow in frame subcloning of any cDNA of interest. This vector, pPLF-26, is similar to pPLF-19 utilized for the expression of human lactoferrin in A.awamori. 5' and 3' oligonucleotide primers can be designed to contain Not1 and EcoR1 ends respectively and used to obtain the full length cDNA sequence encoding for mature porcine and bovine lactoferrin using polymerase chain reaction (PCR) amplification of their known DNA sequence. The PCR fragments can be digested with Not1, repaired using Mung Bean Nuclease (Stratagene) and all digested with EcoR1 which will allow in-frame subcloning to the Not1, repaired, EcoR1 digested pPLF-26. The plasmids can then be transformed into A. awamori to obtain expression and secretion from these cDNAs as previously described for human lactoferrin.

EXAMPLE 7

EXPRESSION OF HUMAN LACTOFERRIN IN DIFFERENT ASPERGILLUS STRAINS: A COMPARATIVE STUDY

This example compares the different levels of hLF expression in different strains of Aspergillus, specifically in A. oryzae and A. nidulans, obtained with different vector constructs. These data are to be compared with the data presented above for the expression of hLF in A. awamori.

A. Expression of Human Lactoferrin in *Aspergillus oryzae*

Expression plasmid, pAhLFG, was designed to contain the complete cDNA sequence encoding human lactoferrin and to be used for expression of the same in A. oryzae. The details of the design, construction, and schematic representation of pAhLFG was presented in co-pending patent application, U.S. Ser. No. 08/250,308, filed May 27, 1994, which is a continuation-in-part of application Ser. No. 07/873,304 filed Apr. 24, 1992, now abandoned. The disclosure of co-pending patent application U.S. Ser. No. 08/250,308 is herein incorporated by reference.

Expression plasmid pAhLFG contains 681 bp of 5'-flanking sequence of the A. oryzae AMY II gene that encodes the α-amylase promoter, secretory signal sequence and first codon of mature α-amylase. The cDNA coding for mature human lactoferrin is subcloned in frame downstream from these sequences allowing recombinant protein production by the addition of starch to the growth medium. The *Aspergillus niger* glucoamylase 3' untranslated region provides the transcription terminator and polyadenylation signals. The plasmid also contains the *Neurospora crassa* pyr4 selectable marker and an ampicillin resistance gene.

Southern blot analyses were performed on transformed *Aspergillus oryzae* strains and the data was previously presented in co-pending patent application, U.S. Ser. No. 08/250,308, filed May 27, 1994, which is a continuation-in-part of application Ser. No. 07/873,304 filed Apr. 24, 1992, now abandoned. Briefly, genomic DNA from individual transformants and control AO7 were hybridized with a radiolabelled hLF cDNA probe (2.1 kb). The results demonstrated a radiolabelled fragment (2.8 kb) generated upon EcoR I digestion of the expression plasmid which is present in all the transformants (#1–9) but is absent in control untransformed AO7.

Northern analyses were performed to determine if lactoferrin mRNA was transcribed correctly and efficiently in A. oryzae under the regulatory control elements of the expression plasmid. This data was previously presented in co-pending patent application, U.S. Ser. No. 08/250,308, filed May 27, 1994, which is a continuation-in-part of application Ser. No. 07/873,304 filed Apr. 24, 1992, now abandoned. Briefly, the results demonstrated that human lactoferrin mRNA was detected using $^{32}$P labelled human LF cDNA (2.0 kb) probe. Hybridization with human LF radiolabelled cDNA probe detected a specific radiolabelled band at the correct size for lactoferrin mRNA (2.3 kb) in the transformant but not in the control untransformed strain. Quantitation of MRNA levels by dot assay showed comparable levels of expression of endogenous α-amylase mRNA between the control AO7 and the transformant tested (#1).

In order to examine the levels of recombinant LF expressed and secreted from A. oryzae, a transformant (#1) was grown in the presence of 3% starch at 30° C. for 72 hours. The growth medium was harvested and the mycelia washed at pH 10 to release any protein loosely associated with the cell wall (Huge-Jensen, et al., *Lipids,* 24:781–785 (1989)). The results are shown in FIG. 16. Western immunoblot analysis using a specific IgG directed against human lactoferrin detected a 78 kD protein corresponding to the size of lactoferrin in the transformant which was absent in control AO7. (FIG. 16A, lanes 2 and 3).

Figure 16A:
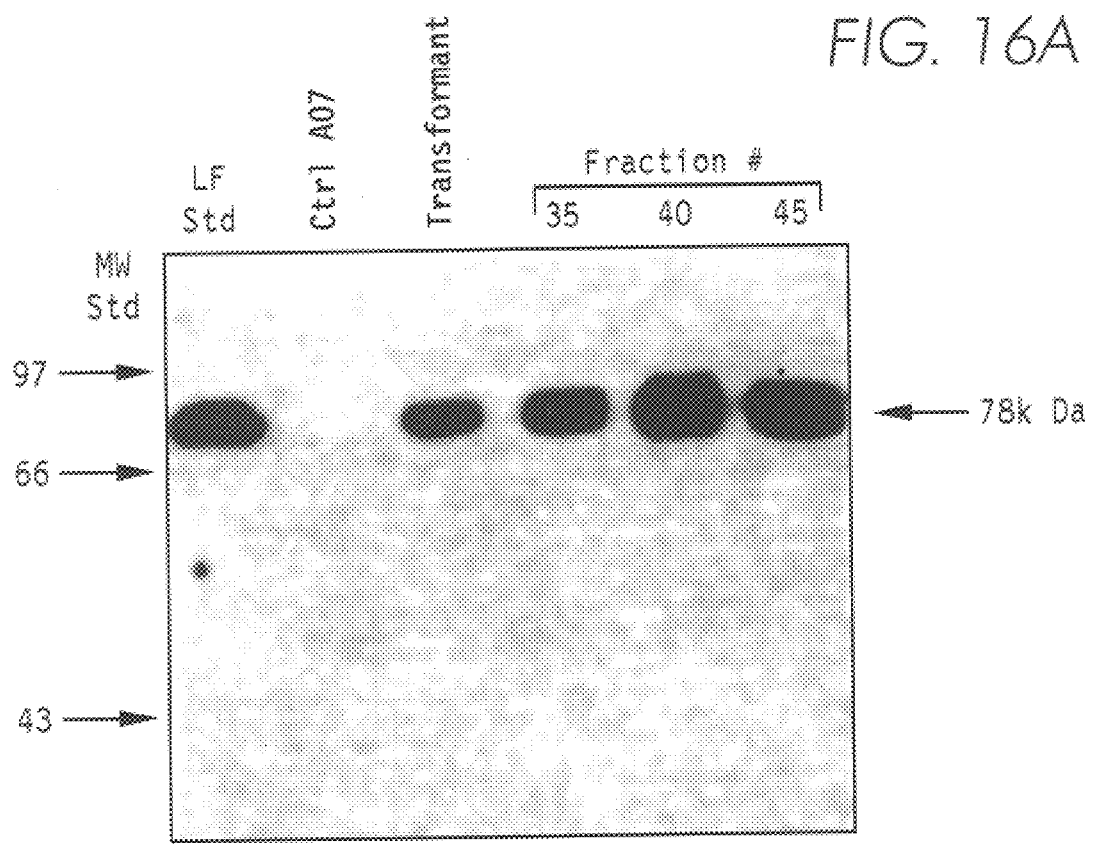
FIG. 16A represents Western immunoblot analysis of recombinant hLF produced in *A. oryzae*.

FIG. 16A: Lane 1 contains breast milk hLF standard (500 ng); Lanes 2 and 3 contain samples of the growth medium (40 ug protein) from induced control AO7 and transformant #1 respectively; Lanes 4–6 contain 25 ul aliquots of eluted fractions (#35, 40, and 45 respectively) collected from the CM-sephadex purification of recombinant hLF from the growth medium.

Figure 16B:
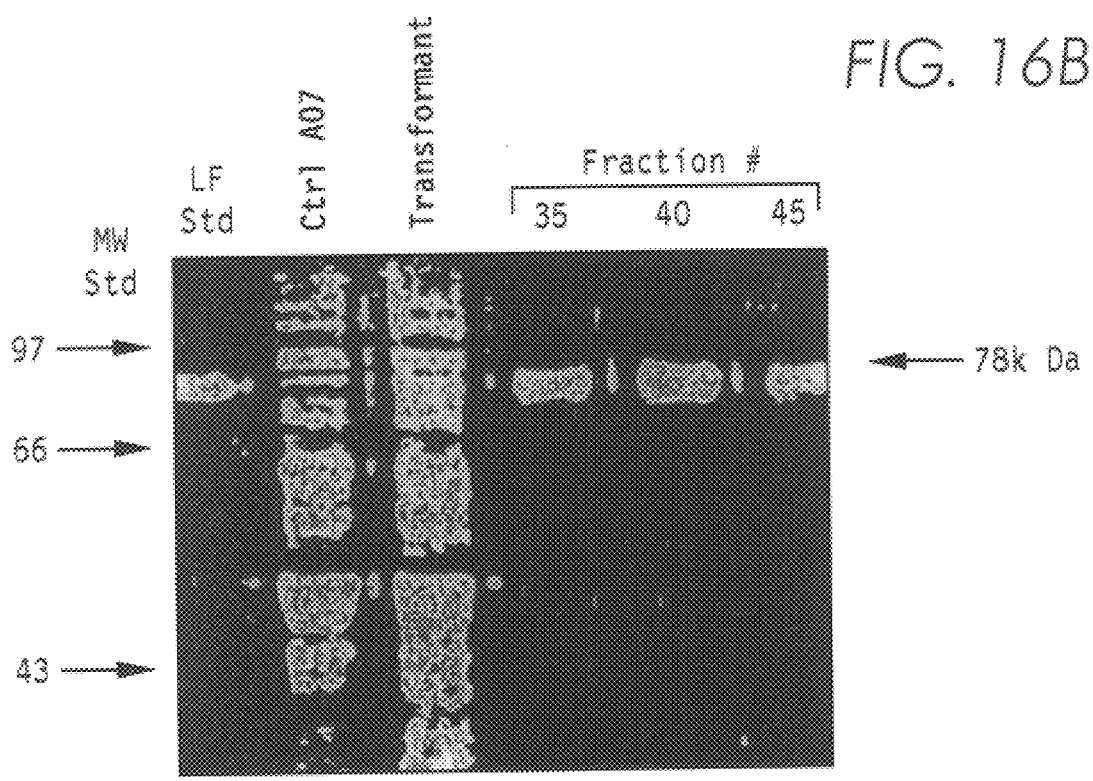
FIG. 16B represents silver-stained SDS-polyacrylamide gel analysis of duplicate samples as in Panel 16A.

Analysis of a duplicate silver stained SDS-PAGE gel also showed the presence of a 78 kD protein in the transformant which was absent in AO7 control (FIG. 16B, lanes 2 and 3). ELISA analysis using a specific biotinylated IgG directed against hLF (Vilja, et al. *J. Immunol. Methods* 76:73–83 (1985)) indicates that the recombinant hLF is secreted at levels of 5–25 mg/l and represents approximately 5% of the total growth medium protein from induced cultures. There was no correlation between copy number integrated and level of recombinant protein secretion. See Table below for vector design and production levels.

Recombinant lactoferrin was purified from the growth medium of transformant #1 by ion-exchange chromatography using CM-Sephadex C5026 (Stowell, et al. *Biochem. J.* 276:349–355 (1991)). Human lactoferrin was eluted from the column using a linear salt gradient. An immunoreactive band corresponding to the size of hLF was detected in fractions 35–45 by Western immunoblotting using a specific IgG directed against hLF (FIG. 16A, lanes 4–6). Analysis of duplicate samples by silver stain SDS-PAGE showed that this immunoreactive hLF corresponds to the major protein band in these fractions (FIG. 16B, lanes 4–6). These results indicate that this single ion exchange chromatography step led to approximately a 95% purification of the recombinant hLF. FIG. 16B: Silver-stained SDS-polyacryamide gel analysis of duplicate samples as described in FIG. 16A.

To determine if hLF was correctly processed at its N-terminus, the recombinant protein was sequenced from the N-terminus through 10 residues using the automated Edman degradation procedure. The bulk of this material was identical to the corresponding amino acids in native human milk LF (Metz-Boutigue, et al. *Eur J. Biochem.* 145:659–676 (1984)) with the exception of the additional alanine residue at the N-terminus (FIG. 16C) which was introduced into our plasmid construction to exactly mimic the linkage of the signal peptide to mature α-amylase. A small proportion had lost the N-terminal Ala-Gly-Arg tripeptide or the Ala-Gly-Arg-Arg tetrapeptide. Previous analysis of native hLF suggests that this processing pattern may be intrinsic to the hLF protein itself (Hutchens, et al. *Proc. Natl. Acad. Sci. U.S.A.* 88:2994–2998 (1991)) or may be due to heterogeneity in the N-terminal processing capabilities of the *A. oryzae* signal peptidases (Christensen, et al. *Bio/Technology* 6:1419–1422 (1988); Huge-Jensen et al. *Lipids* 24:781–783 (1989)).

A. Expression of Human Lactoferrin in *Aspergillus nidulans*

A plasmid was designed and constructed for the expression of hLF cDNA in *A. nidulans*. The details on this vector design and construction (including all intermediate vectors) were was previously described in co-pending patent application having U.S. Ser. No. 08/145,681, filed Oct. 28, 1993.

Briefly, the *A. nidulans* expression plasmid, pAL3hLFT, contains 300 bp of 5'-flanking sequence of the *A. nidulans* alcA gene containing all the regulatory elements necessary for controlled gene expression. This vector contains the alcohol dehydrogenase promoter from *A. nidulans*, the natural hLF signal sequence, cDNA encoding hLF, Ben A 3' untranslated sequences from *A. nidulans* and the *Neurospora crassa* pyr4 selectable marker.

Southern blot analyses were performed on transformed *Aspergillus nidulans* strains and the data was previously described in co-pending patent application having U.S. Ser. No. 08/145,681, filed Oct. 28, 1993, incorporated herein by reference. Briefly, Southern blot analyses were performed to confirm that transformants contained integrated plasmid with hLF cDNA. A hLF-specific radiolabelled band was detected at the expected size (2.3 kb) in lanes 1–10 but not in DNA from control spores. These results demonstrated that hLF cDNA was integrated into the genome of all *A. nidulans* transformants tested and varied randomly from one copy to 20 copies per cell. The site of integration of the plasmid into the *A. nidulans* genome is random due to the absence of homologous sequences to target the vector into a particular site.

The specific details for the production of hLF in *A. nidulans* was previously described in co-pending patent application having U.S. Ser. No. 08/145,681, filed Oct. 28, 1993. Briefly, conidia ($1 \times 10^6$/ml) were cultured in minimal media with Na acetate as carbon source with or without addition of 1.2% ethanol to induce transcription of the hLF cDNA. Media and mycelia were harvested and separated using Miracloth (Calbiochem, San Diego, Calif.). Mycelia (200 mg) were freeze-dried and lyophilized overnight. Total cellular extracts were prepared by homogenization in a glass teflon homogenizer using phosphate-buffered saline in the presence of phenylmethylsulfonylfluoride. The homogenate was centrifuged and the supernatant containing the soluble fraction was recovered. The growth medium was concentrated by freeze drying and lyophilization and resuspended in PBS. Protein concentration was determined using the Bradford reagent according to manufacturer's instructions (BioRad, Richmond, Calif.). Concentrated media samples containing 40 μg protein and soluble extracts (50 μg protein) were subjected to SDS-PAGE. Purified lactoferrin was used as standard (hLF std). The resolved proteins were transferred to nitrocellulose filters electrophoretically using the Western blot procedure. The filters were blocked with Tris-buffered saline containing 2% dried milk and then incubated in the same buffer with the addition of a 1 μg/ml of a specific polyclonal IgG directed against hLF (Sigma, St. Louis, Mo.). The filter were washed in TBS/0.05% Nonidet P-40 followed by incubation with [$^{125}$I] protein A. The filter was then washed, dried and exposed overnight to Kodak XAR5 film at −70° C. The film was then developed by autoradiography. The autoradiographs demonstrate production of hLF.

Western analysis was performed to determine if the hLF cDNA was expressed in the *A. nidulans* transformants under the control of the alcA promoter. Conidia ($1 \times 10^6$/ml) from one transformant (No. 5), which contained the highest number of copies of integrated hLF cDNAs. The cultures were harvested, washed and reinoculated into minimal medium supplemented with ethanol and grown for an additional 12 or 24 h before harvesting the cultures. Cell extracts and samples of the growth medium were resolved by SDS-PAGE, transferred to nitrocellulose and immunoblotted using a specific polyclonal IgG directed against hLF. An immunoreactive band indistinguishable from native hLF was evident in the cells and growth medium from transformant No. 5 after 12 and 24 h growth only after ethanol induction. These results demonstrate that hLF is expressed in transformed A. nidulans under the control of the alcA promoter.

Western analysis revealed hLF in the cells in all of the remaining transformants (data not shown). In general, there was a correlation between the plasmid copy number and the expression levels obtained. In the medium, hLF was detected only with transformants containing multiple copies of integrated expressed plasmids (Nos. 1, 5, 7 and 10).

The pilot fermentation of transformant No. 5 was carried to determine the approximate amount of hLF produced ELISA analysis, using a specific biotinylated IgG directed against hLF, demonstrated that the total level of recombinant hLF produced was 5 mg/l with approx. 30% (1.5–2.0 μg/ml) of this material secreted into the medium. See Table below for vector design and productions levels.

Thus, this Example demonstrates that the Applicants have improved and enhanced the expression of human lactoferrin by modifying the design of the expression vector plasmid constructs and by changing the host cells used. As noted in the table below, several different vector constructs have been used to produce human lactoferrin in at least four different Aspergillus strains. The amount of human lactoferrin produced is shown in milligrams hLF per liter.

For convenience, each vector component is listed in the order that it appears in the vector construct directionally positioned from left to right. The components included in the expression plasmid vector include: a promoter and the source of the promoter, a signal sequence and the source of the signal sequence, a linker sequence, DNA encoding for human lactoferrin, a transcription termination sequence, and a selectable marker.

may employ DNA sequences encoding polypeptide fragments of lactoferrin which maintain characteristics of lactoferrin. One of ordinary skill in this art will understand and know that the scope of this invention also includes the production of the different published and obvious therefrom allelic variants of human, porcine or bovine lactoferrin. Some allelic variations have been reported in the literature and they are intended to be included as the types of lactoferrins that may be produced by the process of the subject invention.

EXAMPLE 9

FERMENTATION PROTOCOLS

Different growth and production conditions can be used for the expression of recombinant human lactoferrin in *Aspergillus awamori*. The following descriptions are presented for the purposes of illustrating various conditions which can be used for the expression of hLF in *Aspergillus awamori* and are not meant to be limitations of the present invention in any form. Presented below is a general outline of the fermentation production process and the process used to recover the produced lactoferrin. One of ordinary skill in this art understands that the protocol may be changed or modified in minor ways in order to enhance the production of the desired lactoferrin or lactoferrin polypeptide.

The following is a brief outline for producing lactoferrin by using a fermentation process.

I. FERMENTATION PROCESS

A. MEDIUM COMPONENTS

TABLE 1

Human Lactoferrin Production Levels in Different Aspergillus Strains Using Different Vectors

| Vector | Host Cells | Promoter (Source) | Signal Sequence (Source) | Linker Sequence | cDNA | Transcription Termination Sequence | Selectable Marker | mg/liter HuLF Produced |
|---|---|---|---|---|---|---|---|---|
| A(92) | A. oryzae | α-amylase (A. oryzae) | α-amylase (A. oryzae) | — | hLF | 3' untranslated from glucoamylase (A. niger) | pyr4 (Neurospora crassa) | 5–25 |
| B(1093) | A. nidulans | alcohol dehydrogenase (alc - A) (A. nidulans) | natural huLF signal sequence | — | hLF | 3' untranslated from Ben A (A. nidulans) | pyr4 (Neurospora crassa) | 5 |
| C(0594) | A. awamori | glucoamylase (A. awamori) | glucoamylase (A. awamori) plus 5' ½ end of glucoamylase gene (A. awamori) | Synthetic Linker which codes for Kex2 peptidase cleavage site | hLF | 3' untranslated from glucoamylase (A. niger) | phleomycin | 500 |
| D(0894) | A. awamori | glucoamylase (A. awamori) | glucoamylase (A. awamori) plus 5' ½ end of glucoamylase gene (A. awamori) | Synthetic Linker which codes for Kex2 peptidase cleavage site | hLF | 3' untranslated from glucoamylase (A. niger) | phleomycin | 900 |

EXAMPLE 8

PRODUCTION OF LACTOFERRIN USING PUBLISHED DNA SEQUENCES WHICH CONTAIN ALLELIC VARIATIONS

One may employ any one of several known DNA sequences encoding for lactoferrins as identified in the published literature and patent applications referenced above, incorporated herein by reference. Additionally, one 1) Seed medium

| | |
|---|---|
| Roquette Corn Steep Powder | 100 g/L |
| Glucose | 10 g/L |
| $MgSO_4$-$7H_2O$ | 1 g/L |
| $NaH_2PO_4$-$2H_2O$ | 1 g/L | pH to 5.8 before autoclaving and autoclave for 15 minutes.

2) Production medium (concentrations are post-inoculation)

| | |
|---|---|
| Amaizo Lodex-5 partially hydrolyzed corn starch | 175 g/L |
| Roquette Corn Steep Powder (Solulys ® A ST) | 60 g/L |
| Trisodium Citrate | 80 g/L |
| $MgSO_4$-$7H_2O$ | 2 g/L |
| $NaH_2PO_4$-$2H_2O$ | 1.3 g/L |
| Ammonium sulfate | 15 g/L |
| Antifoam 204 | 2 ml/L | pH to 6.2 before autoclaving and autoclave for 15 minutes.

The inventors have found that enhanced lactoferrin production can be achieved when partially hydrolyzed starches are used in the fermentation process. However, combinations of unmodified corn starch and dextrose have yielded reasonable production of lactoferrin. One may employ less amounts of starch products or substitute more expensive starch products to optimize production of the lactoferrin by routine experimentation.

B. FERMENTATION PROCESS

To date, the fermentation is run as a batch process. Maximum product concentration is reached at 5–6 days.

1) Seed stage 1
   a) 450 mls of seed medium in a 2L Erlenmeyer flask
   b) Inoculate with $1 \times 10^6$ spores per ml of seed medium.
   c) Incubate for 24 hours at 33° C., 70% relative humidity at 240 rpm (50 mm throw shaker).

2) Seed stage 2
   a) 20L seed medium in a NBS Micros 30 fermenter with two 12 cm six-blade rushton impellers.
   b) 30 minute sterilization.

| Inoculate with 2% of stage 1 seed | |
|---|---|
| Agitation | 500 rpm |
| Airflow | 0.75 VVM |
| Pressure | 300 mbar |
| pH | not controlled |
| DO | not controlled |

3) Production

The pilot vessel is a B. Braun Biotech UD100 with a 3:1 aspect ratio. Two 16 cm six-blade Rushton impellers are used for agitation. The fermentation is run at 80L post-inoculation.

| | | |
|---|---|---|
| Agitation | 450 rpm | Power input has not yet been examined. |
| Temperature | 33° C. | |
| Aeration | 0.75 VVM | This variable has not yet been examined. |
| Pressure | 300 mbar | |
| pH | not controlled | |
| DO | not controlled | This variable has not yet been examined. |
| Antifoam | not required | |

Vessel conditions are as described above. Vessel is charged with 80L of Medium Components and brought to a volume of 72L with deionized water. It is sterilized for 30 minutes. Eight liters (10% CV) of Stage 2 seed is transferred at 36–48 hours growth. Optimized seed processes are currently being developed.

Lactoferrin production is seen by 24 hours with maximum product accumulation at 5–6 days.

II. DOWNSTREAM PROCESSING

A. FILTRATION

The fermentation reaches a 30–40% packed cell volume with a non-pelleted morphology. If filtration is used to clarify the broth, a filter aid is required. Because of the low process volumes, straight vacuum filtration over a 3,000 $cm^2$ support may be used. A polypropylene filter mat is used as a base.

Initial tests used diatomaceous earth as the filter aid. However, straight-calcined or flux-calcined diatomaceous earth cannot be used as a filter aid as they bind lactoferrin. Only acid-washed diatomaceous earth will not bind lactoferrin. Acid-washed diatomaceous earth (DE) can be purchased at 40–50 times the cost of the untreated product. Another option is to acid wash the DE at the production site. Preliminary tests determined that it can be slurried with 3N HCl, mixed for 45 minutes and then washed with deionized water until the wash water is pH 4.0. Lactoferrin did not bind to this treated material. The treated DE was used at a 1:5 W/V ratio with whole broth. The DE was slurried with deionized water prior to mixing with the broth. It was found that a 1:10 ratio did not allow filtration.

An alternative product is cellulose fiber. The inventors have found that Solkafloc 10IND (Protein Technologies International in Urbana, Ill.; 1-800-258-0351) works well with no binding of lactoferrin. The inventors use Solkafloc as a filler to aid filtration. For 100L of fermentation broth, 20 kg of Solkafloc is slurried with 100L of deionized water. The broth is mixed into the slurry. The mixture is then filtered easily. The clarity achieved at this step enables further downstream processing (ultrafiltration and column chromatography) to proceed without additional filtration requirements. The ratio of Solkafloc to broth and deionized water for a single batch filtration is in the process of being optimized. Recovery of lactoferrin should almost be quantitative if the filter cake is washed. With continuous filtration process equipment, the methods for using Solkafloc as a filter aid will change.

One may use existing strains or develop strains with improved rheology and filtration characteristics. For example, mutants that pellet in stirred tank fermentation will allow thicker filter cakes during processing and will not require filter aid except as a filter precoat.

B. ULTRAFILTRATION

The clarified broth is concentrated using Sultrafiltration. Two Amicon S10Y30 (0.93 $m^2$ each) spiral cartridges with 30,000 MW membranes are used with an Amicon DC-30 system. The membranes are a low protein-binding cellulose-based material. Flux rates are 1–1.8 rpm depending on the stage of the process. Once a minimum operational process volume has been reached, the concentrated solution is continuously dialyzed with five volumes of a buffer containing 0.1M NaCl, 1 mM EDTA, and 25 mM TRIS pH 7.5. The buffer is then cooled to 4° C. and the dialyzed solution is concentrated to the minimum volume possible and recovered. Yields have been near 100% with this process.

The final ultrafiltration (UF) concentrate is 5–8 mg/ml total protein with lactoferrin at 10% of total protein. The recovery rate will be optimized as new strains are developed. For an 80L fermentation batch, concentration and dialysis with this system takes approximately 2 hours.

C. CHROMATOGRAPHIC SEPARATION

Pharmacia CM Sepharose Fast Flow gel is used. The binding capacity of this resin for lactoferrin in clarified broth is approximately 20 mg/ml.

UF concentrate is applied to the column. The loaded column is washed first with 0.1M NaCl/25 mM TRIS pH 7.5, and then with a 0.2M NaCl 25 mM TRIS pH 7.5. No lactoferrin will be released unless the column is overloaded. The lactoferrin is eluted with 0.5M NaCl/25 mM TRIS pH 7.5. The volume of the elution fractions containing lactoferrin is usually twice the volume of the resin bed.

D. CONVERSION TO APOLACTOFERRIN

The 0.5M NaCl fractions containing lactoferrin are combined. 1M ammonium citrate is added to bring the final concentration to 0.1M ammonium citrate. The pH is slowly adjusted to 2.0 with 10N HCl. The solution is transferred to an appropriately sized ultrafiltration unit using 30,000 MW membranes where it is concentrated to an appropriate volume and then continuously dialyzed with five volumes of 0.5M NaCl/0.1M Ammonium citrate pH 2.0. After release and dialysis of iron is completed, the pH is adjusted to neutral to prevent precipitation in the next process. If there is residual iron present, it will rebind to the lactoferrin at the neutral pH. The dialysis buffer is changed to 50 mM ammonium bicarbonate (pH 7.8) and the solution is continuously dialyzed with five volumes of buffer. The solution is then concentrated to a minimum volume, recovered, and lyophilized.

The procedure is currently being optimized. Specific factors are considered on a case by case basis depending on the strain used. Some of the factors include (1) pH limits, (2) pre-treatment of equipment to eliminate iron, and (3) pre-treatment of buffers with Chelex resins to remove trace amounts of iron. It may be necessary to go through an intermediate buffer such as 0.2M NaCl 50 mM Ammonium bicarbonate to avoid precipitation of lactoferrin and rebinding of residual iron.

EXAMPLE 10

PRODUCTION OF LACTOFERRIN OR LACTOFERRIN POLYPEPTIDE FRAGMENTS AS A FUSION PRODUCT IN *ASPERGILLUS ORYZAE* OR *ASPERGILLUS NIGER* CELLS

A. Expression of Lactoferrin or Lactoferrin Polypeptide Fragments in *Aspergillus Oryzae*

A similar expression vector as that which has been previously described can be constructed to allow for the expression of lactoferrin or lactoferrin polypeptide fragments as a fusion protein product in *Aspergillus oryzae*. The *A. oryzae* expression vector would contain the following components operably linked from 5' to 3':

(a) a promoter from *Aspergillus oryzae* α-amylase gene;

(b) signal sequence from the *A. oryzae* α-amylase gene;

(c) 5' portion of the *A. oryzae* α-amylase gene;

(d) linker sequence encoding Kex2 peptidase cleavage site whereby there is an endogenous proteolytic enzyme specific for said linker sequence;

(e) transcription termination sequence from the *A. niger* glucoamylase gene; and (f) phleomycin resistance selectable marker gene;

wherein said vector is capable of producing lactoferrin or a lactoferrin polypeptide fragment as a fusion protein and expressing the same as a processed protein.

The vector would then be used to transform *A. oryzae* cells; the product of this novel plasmid vector construct is a fusion protein comprised of half of the highly expressed *A. oryzae* α-amylase gene fused to the lactoferrin or lactoferrin polypeptide fragment corresponding to the nucleotide sequence of step (e) above. The lactoferrin or lactoferrin polypeptide fragment fusion product would then be processed by an endogenous *A. oryzae* proteolytic enzyme which is specific for the Kex2 peptidase site.

B. Expression of Lactoferrin or Lactoferrin Polypeptide Fragments in *Aspergillus Niger*

A similar expression vector as that which has been previously described can be constructed to allow for the expression of lactoferrin or lactoferrin polypeptide fragments as a fusion protein product in *Aspergillus niger*. The *A. niger* expression vector would contain the following components operably linked from 5' to 3':

(a) promoter from *Aspergillus niger* glucoamylase gene;

(b) signal sequence from the *A. niger* glucoamylase gene;

(c) 5' portion of the *A. niger* glucoamylase gene;

(d) linker sequence encoding Kex2 peptidase cleavage site whereby there is an endogenous proteolytic enzyme specific for said linker sequence;

(e) transcription termination sequence from the *A. niger* glucoamylase gene; and (f) phleomycin resistance selectable marker gene;

wherein said vector is capable of producing lactoferrin or a lactoferrin polypeptide fragment as a fusion protein and expressing the same as a processed protein.

The vector would then be used to transform *A. niger* cells; the product of this novel plasmid vector construct is a fusion protein comprised of half of the highly expressed *A. niger* glycoamylase gene fused to the lactoferrin or lactoferrin polypeptide fragment corresponding to the nucleotide sequence of step (e) above. The lactoferrin or lactoferrin polypeptide fragment fusion product would then be processed by an endogenous *A. niger* proteolytic enzyme which is specific for the Kex2 peptidase site.

In conclusion, it is seen that the present invention and the embodiments disclosed herein are well adapted to carry out the objectives and obtain the end set forth in this application. Certain changes can be made in the method and apparatus without parting from the spirit and scopes of this invention. It is realized that changes are possible and that it is further intended that each element or step presided in any of the filing claims is to be understood as to referring to all equivalent elements or steps for accomplishing the essentially the same results in substantially the same or equivalent manner. It is intended to cover the invention broadly in whatever form its principles may be utilized. The present invention, therefore, is well adapted to carry out the objects and obtain the ends and advantages mentioned, as well as others inherent therein.

We claim:

1. A recombinant expression plasmid vector comprising the following components operably linked 5' to 3':
   (a) a promoter;
   (b) a nucleotide sequence encoding a signal peptide;
   (c) a nucleotide sequence encoding an amino-terminal portion of an endogenous secreted Aspergillus polypeptide;
   (d) a nucleotide sequence encoding a peptide linker, said peptide linker comprising a fungal peptidase cleavage site; and
   (e) a nucleotide sequence encoding a lactoferrin or lactoferrin polypeptide fragment;

wherein said vector permits the expression of a lactoferrin or a lactoferrin polypeptide fragment as a fusion protein and the subsequent production of same as a processed protein.

2. The vector of claim 1, wherein said promoter is selected from genes of the group consisting of alcohol dehydrogenase, α-amylase, glucoamylase, and benA.

3. The vector of claim 2, wherein said promoter is from the glucoamylase gene.

4. The vector of claim 3, wherein the glucoamylase gene is from *A. awamori* or *A. niger*.

5. The vector of claim 2, wherein said promoter is from the α-amylase gene.

6. The vector of claim 5, wherein the α-amylase gene is from *A. oxyzae*.

7. The vector of claim 1, wherein said signal sequence is selected from the genes of the group consisting of glucoamylase and α-amylase.

8. The vector of claim 7, wherein said signal sequence is from the *A. awamori* or *A. niger* glucoamylase gene.

9. The vector of claim 7, wherein said signal sequence is from the *A. oryzae* α-amylase gene.

10. The vector of claim 1, wherein said highly expressed endogenous gene is selected from the group consisting of α-amylase gene and glucoamylase gene.

11. The vector of claim 10, wherein said highly expressed endogenous gene is the *A. oryzae* α-amylase gene.

12. The vector of claim 10, wherein said highly expressed endogenouse gene is the *A. awamori* or *A. niger* glucoamylase gene.

13. The vector of claim 1, wherein said linker sequence is a peptidase cleavage site.

14. The vector of claim 13, wherein said linker sequence encodes the Kex2 peptidase cleavage site.

15. The vector of claim 1, wherein said lactoferrin or lactoferrin polypeptide fragment is human, bovine or porcine.

16. The vector of claim 1, further comprising a transcription termination sequence and a selectable marker.

17. The vector of claim 16, wherein said transcription termination sequence is selected from the genes of the group consisting of α-amylase, glucoamylase, alcohol dehydrogenase and benA.

18. The vector of claim 17, wherein said transcription termination sequence is from the *A. niger* glucoamylase gene.

19. The vector of claim 16, wherein said selectable marker gene is selected from the genes of the group consisting of pyr4, pyrG, amdS, argB, trpC, and phleomycin resistance.

20. The vector of claim 19, wherein said selectable marker is the phleomycin resistance gene.

21. A recombinant expression plasmid vector comprising the following components operably linked from 5' to 3':

(a) a promoter from the *A. awamori* glucoamylase gene;

(b) a a nucleotide sequence encoding a signal peptide from the *A. awamori* glucoamylase gene;

(c) a nucleotide sequence encoding an amino-terminal portion of the *A. awamori* glucoamylase gene;

(d) a nucleotide sequence encoding a Kex2 peptidase cleavage site whereby there is an endogenous proteolytic enzyme specific for said nucleotide sequence;

(e) a nucleotide sequence encoding lactoferrin or a lactoferrin polypeptide fragment;

(f) a transcription termination sequence from the *A. niger* glucoamylase gene; and (g) a phleomycin resistance selectable marker gene; wherein said vector permits the expression of a lactoferrin or a lactoferrin polypeptide fragment as a fusion protein and the subsequent production of the same as a processed protein.

22. A recombinant expression plasmid vector comprising the following components operably linked from 5' to 3':

(a) a promoter from the *A. niger* glucoamylase gene;

(b) a nucleotide sequence encoding a signal peptide from the *A. niger* glucoamylase gene;

(c) a nucleotide sequence encoding an amino-terminal portion of the *A. niger* glucoamylase gene;

(d) a nucleotide sequence encoding Kex2 peptidase cleavage site whereby there is an endogenous proteolytic enzyme specific for said nucleotide sequence;

(e) a nucleotide sequence encoding a lactoferrin or a lactoferrin polypeptide fragment;

(f) a transcription termination sequence from the *A. niger* glucoamylase gene; and (g) a phleomycin resistance selectable marker gene; wherein said vector permits the expression of a lactoferrin or a lactoferrin polypeptide fragment as a fusion protein and the subsequent production of the same as a processed protein after transformation of said vector into *A. niger* cells.

23. A recombinant expression plasmid vector comprising the following components operably linked from 5' to 3':

(a) a promoter from the *A. oryzae* α-amylase gene;

(b) a nucleotide sequence encoding a signal peptide from the *A. oryzae* α-amylase gene;

(c) a nucleotide sequence encoding an amino-terminal portion of the *A. oryzae* α-amylase gene; (d) a nucleotide sequence encoding Kex2 peptidase cleavage site whereby there is an endogenous proteolytic enzyme specific for said nucleotide sequence;

(e) a nucleotide sequence encoding a lactoferrin or a lactoferrin polypeptide fragment;

(f) a transcription termination sequence from the *A. niger* glucoamylase gene; and (g) α-phleomycin resistance selectable marker gene; wherein said vector permits the expression of a lactoferrin or a lactoferrin polypeptide fragment as a fusion protein and the subsequent production of the same as a processed protein.

24. An expression plasmid vector comprising the following components operably linked from 5' to 3':

(a) a promoter from the *A. awamori* glucoamylase gene;

(b) a nucleotide sequence encoding a signal peptide from the *A. awamori* glucoarnylase gene;

(c) a nucleotide sequence encoding an amino-terminal portion of the *A. awamori* glucoamylase gene;

(d) a nucleotide sequence encoding Kex2 peptidase cleavage site whereby there is an endogenous proteolytic enzyme specific for said nucleotide sequence;

(e) a nucleotide sequence encoding a human lactoferrin or a human lactoferrin polypeptide fragment;

(f) a transcription termination sequence from the *A. niger* glucoamylase gene; and (g) a phleomycin resistance selectable marker gene; wherein said plasmid is used for expressing human lactoferrin or a human lactoferrin polypeptide fragment in Aspergillus fungal cells.

25. The plasmid of claim 24, further defined as having ATCC Accession No. 74290 and designated Awa LF 24-1.

26. *Aspergillus awamori* fungal cells containing the plasmid of claim 24.

27. A process for producing lactoferrin which comprises culturing a transformed Aspergillus fungal cell comprising a recombinant plasmid, wherein said plasmid comprises the following components operably linked from 5' to 3':

(a) a promoter;

(b) a nucleotide sequence encoding a signal peptide; (c) a nucleotide sequence encoding an amino-terminal portion of an endogenous secreted Aspergillus polypeptide;

(d) a nucleotide sequence encoding a peptide linker, said peptide linker comprising a fungal peptidase cleavage site; and (e) a nucleotide sequence encoding a lactoferrin or a lactoferrin polypeptide fragment;

wherein said transformed Aspergillus fungal cells are cultured in a suitable nutrient medium until lactoferrin protein or lactoferrin polypeptide fragment is produced as a fusion product and then processed via an endogenous proteolytic enzyme specific for said linker sequence, wherein said processed lactoferrin or lactoferrin polypeptide fragment is secreted into the nutrient medium and isolated therefrom.

28. The process of claim 27, wherein said promoter is selected from genes of the group consisting of alcohol dehydrogenase, α-amylase, glucoamylase, and benA.

29. The process of claim 28, wherein said promoter is from the glucoamylase gene.

30. The process of claim 29, wherein the glucoamylase gene is from *A. awamori* or *A. niger*.

31. The process of claim 28, wherein said promoter is from the α-amylase gene.

32. The process of claim 31, wherein the α-amylase gene is from *A. oryzae*.

33. The process of claim 27, wherein said signal sequence is selected from the genes of the group consisting of glucoamylase and α-amylase.

34. The process of claim 33, wherein said signal sequence is from the *A. awamori* glucoamylase gene.

35. The process of claim 33, wherein said signal sequence is from the *A. oryzae* α-amylase gene.

36. The process of claim 27, wherein said highly expressed endogenous gene is selected from the group consisting of α-amylase gene and glucoamylase gene.

37. The process of claim 36, wherein said highly expressed endogenous gene is the *A. oryzae* α-amylase gene.

38. The process of claim 36, wherein said highly expressed endogenouse gene is the *A. awamori* glucoamylase gene.

39. The process of claim 27, wherein said linker sequence is a peptidase cleavage site.

40. The process of claim 38, wherein said linker sequence encodes the Kex2 peptidase cleavage site.

41. The process of claim 27, wherein said plasmid further comprises a transcription termination sequence and a selectable marker gene.

42. The process of claim 41, wherein said transcription termination sequence is selected from the genes of the group consisting of α-amylase, glucoamylase, alcohol dehydrogenase and benA.

43. The process of claim 42, wherein said transcription termination sequence is from the *A. niger* glucoamylase gene.

44. The process of claim 28, wherein said selectable marker gene is selected from the genes of the group consisting of pyr4, pyrG, amdS, argB, trpC, and phleomycin resistance.

45. The process of claim 44, wherein said selectable marker is the phleomycin resistance gene.

46. A process for producing lactoferrin which comprises culturing a transformed *Aspergillus awamori* fungal cell comprising a recombinant plasmid, wherein said plasmid comprises the following components operably linked from 5' to 3':

(a) a promoter from the *A. awamori* glucoamylase gene;

(b) a nucleotide sequence encoding a signal peptide from the *A. awamori* glucoamylase gene;

(c) a nucleotide sequence encoding an amnino-terminal portion of the *A. awamori* glucoamylase gene;

(d) a nucleotide sequence encoding Kex2 peptidase cleavage site whereby there is an endogenous proteolytic enzyme specific for said nucleotide sequence;

(e) a nucleotide sequence encoding a human lactoferrin or a human lactoferrin polypeptide fragment;

(f) a transcription termination sequence from the *A. niger* glucoamylase gene; and (g) a phleomycin resistance selectable marker gene;

wherein said transformed *Aspergillus awamori* fungal cell is cultured in a suitable nutrient medium until lactoferrin or lactoferrin polypeptide fragment is produced as a fusion product and then processed via an endogenous proteolytic enzyme specific for said linker sequence, wherein said processed lactoferrin or lactoferrin polypeptide fragment is secreted into the nutrient medium and isolated therefrom.

47. A process for producing lactoferrin which comprises culturing a transformed *Aspergillus oryzae* fungal cell comprising a recombinant plasmid, wherein said plasmid comprises the following components operably linked from 5' to 3':

(a) a promoter from the *A. oryzae* α-amylase gene;

(b) a nucleotide sequence encoding a signal peptide from the *A. oryzae* α-amylase gene;

(c) a nucleotide sequence encoding an amino-terminal portion of the *A. oryzae* α-amylase gene;

(d) a nucleotide sequence encoding Kex2 peptidase cleavage site whereby there is an endogenous proteolytic enzyme specific for said nucleotide sequencer;

(e) a nucleotide sequence encoding a lactoferrin or a lactoferrin polypeptide fragment;

(f) a transcription termination sequence from the *A. niger* glucoamylase gene; and (g) α-phleomycin resistance selectable marker gene;

wherein said transformed *Aspergillus oryzae* fungal cell is cultured in a suitable nutrient medium until lactoferrin or a lactoferrin polypeptide fragment is produced as a fusion product and then processed via an endogenous proteolytic enzyme specific for said nucleotide sequence, wherein said processed lactoferrin or lactoferrin polypeptide fragment is secreted into the nutrient medium and isolated therefrom.

48. A process for producing lactoferrin which comprises culturing a transformed *Aspergillus niger* fungal cell comprising a recombinant plasmid, wherein said plasmid comprises the following components operably linked from 5' to 3':

(a) a promoter from the *A. niger* glucoamylase gene;

(b) a nucleotide sequence encoding a signal peppide from the *A. niger* glucoamylase gene;

(c) a nucleotide sequence encoding an amino-terminal portion of the *A. awamori* glucoamylase gene;

(d) a nucleotide sequence encoding Kex2 peptidase cleavage site whereby there is an endogenous proteolytic enzyme specific for said nucleotide sequence;

(e) a nucleotide sequence encoding lactoferrin or lactoferrin polypeptide fragment;

(f) a transcription termination sequence from the *A. niger* glucoamnylase gene; and (g) a phleomycin resistance selectable marker gene;

wherein said transformed *Aspergillus niger* fungal cell is cultured in a suitable nutrient medium until lactoferrin or lactoferrin polypeptide fragment is produced as a fusion product and then processed via an endogenous proteolytic enzyme specific for said linker sequence, wherein said processed lactoferrin or lactoferrin polypeptide fragment is secreted into the nutrient medium and isolated therefrom.

49. A method of isolating lactoferrin polypeptide fragment from fungal nutrient medium comprising culturing a transformed *Aspergillus awamori* fungal cell comprising a recombinant plasmid vector, wherein said plasmid vector comprises a promoter from *A. awamori* glucoamylase gene, a signal sequence from the *A. awamori* glucoamylase gene, a 5' portion of the *A. awamori* glucoamylase gene, a linker sequence encoding Kex2 peptidase cleavage site whereby there is an endogenous proteolytic enzyme is specific for said linker sequence, a nucleotide sequence encoding a lactoferrin or lactoferrin polypeptide fragment, a transcription termination sequence from the *A. niger* glucoamylase gene, and a phleomycin resistance selectable marker gene and wherein said transformed *Aspergillus awamori* fungal cells are cultured in a suitable nutrient medium until lactoferrin or lactoferrin polypeptide fragment is produced as a fusion product and then processed via an endogenous proteolytic enzyme specific for said linker sequence, wherein said processed lactoferrin or lactoferrin polypeptide fragment is secreted into the nutrient medium and isolated therefrom.

50. Lactoferrin or lactoferrin polypeptide fragment produced when the vector of claim 1 is used to transform Aspergillus fungal cells.

51. Lactoferrin or lactoferrin polypeptide fragment produced and processed when the vector of claim 22 is used to transform *Aspergillus awamori* fungal cells.

52. Lactoferrin or lactoferrin polypeptide fragment produced and processed when the vector of claim 23 is used to transform *A. oryzae* fungal cells.

53. Lactoferrin protein or lactoferrin polypeptide fragment produced by the process of claim 27.

54. The lactoferrin protein of claim 53, wherein the lactoferrin or lactoferrin polypeptide fragment is the human, the porcine or the bovine lactoferrin.

55. A lactoferrin protein or a lactoferrin polypeptide fragment as produced by a process for producing lactoferrin which comprises culturing a transformed *Aspergillus awamori* fungal cell comprising a recombinant plasmid, wherein said plasmid comprises the following components operably linked from 5' to 3':

(a) a promoter from the *A. awamori* glucoamylase gene;

(b) a nucleotide sequence encoding a signal peptide from the *A. awamori* glucoamylase gene;

(c) a nucleotide sequence encoding an amino-terminal portion of the *A. awamori* glucoamylase gene;

(d) a nucleotide sequence encoding Kex2 peptidase cleavage site whereby there is an endogenous proteolytic enzyme specific for said nucleotide sequence;

(e) a nucleotide sequence encoding lactoferrin or lactoferrin polypeptide fragment;

(f) a transcription termination sequence from the *A. niger* glucoamylase gene; and (g) a phleomycin resistance selectable marker gene;

wherein said transformed *Aspergillus awamori* fungal cell is cultured in a suitable nutrient medium until lactoferrin or lactoferrin polypeptide fragment is produced as a fusion product and then processed via an endogenous proteolytic enzyme specific for said linker sequence, wherein said processed lactoferrin or lactoferrin polypeptide fragment is secreted into the nutrient medium and isolated therefrom.

\* \* \* \* \*

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (iii) HYPOTHETICAL: NO (iv) ANTI-SENSE: NO (xi) SEQUENCE DESCRIPTION: SEQ ID NO:1:

GGGGTACCGC GCCGGCCGTA GGAGAAGGAG TG                                    32

(2) INFORMATION FOR SEQ ID NO:2:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (iii) HYPOTHETICAL: NO (iv) ANTI-SENSE: NO (xi) SEQUENCE DESCRIPTION: SEQ ID NO:2:

TTCGGTCCCG TAGACTTCCG CCGCT                                            25

(2) INFORMATION FOR SEQ ID NO:3:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (iii) HYPOTHETICAL: NO (iv) ANTI-SENSE: NO (xi) SEQUENCE DESCRIPTION: SEQ ID NO:3:

TATGCAGAGG AGCTCTCCCC TGAC                                             24

(2) INFORMATION FOR SEQ ID NO:4:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (iii) HYPOTHETICAL: NO (iv) ANTI-SENSE: NO (xi) SEQUENCE DESCRIPTION: SEQ ID NO:4:

GATTCCGCCG GCCAACCCTG TGCAGACGAG GC                                    32

(2) INFORMATION FOR SEQ ID NO:5:

(i) SEQUENCE CHARACTERISTICS:
          (A) LENGTH: 19 base pairs (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:5:

GAATTTCAAG CTAGATGCT                                                                19

(2) INFORMATION FOR SEQ ID NO:6:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:6:

AGCGTGACCT CGACCAGCAA GAATGTGATT TCCAAGCGC                                          39

(2) INFORMATION FOR SEQ ID NO:7:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:7:

TCGCACTGGA GCTGGTCGTT CTTACACTAA AGGTTCGCG                                          39

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:8:

AGCGCGGCCG CAGGAGAAGG A                                                             21